(12) United States Patent
Uytingco et al.

(10) Patent No.: US 11,624,086 B2
(45) Date of Patent: Apr. 11, 2023

(54) SIMULTANEOUS SPATIO-TEMPORAL MEASUREMENT OF GENE EXPRESSION AND CELLULAR ACTIVITY

(71) Applicant: 10x Genomics, Inc., Pleasanton, CA (US)

(72) Inventors: Cedric Uytingco, Pleasanton, CA (US); Layla Katiraee, Pleasanton, CA (US); Kristen Pham, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/541,818

(22) Filed: Dec. 3, 2021

(65) Prior Publication Data

US 2022/0090175 A1 Mar. 24, 2022

Related U.S. Application Data

(63) Continuation of application No. PCT/US2021/033405, filed on May 20, 2021.

(60) Provisional application No. 63/044,028, filed on Jun. 25, 2020, provisional application No. 63/029,121, filed on May 22, 2020.

(51) Int. Cl.
| | |
|---|---|
| *C12Q 1/6818* | (2018.01) |
| *C12N 5/00* | (2006.01) |
| *C12Q 1/6804* | (2018.01) |
| *C12Q 1/6837* | (2018.01) |
| *C12Q 1/6841* | (2018.01) |
| *C12Q 1/6876* | (2018.01) |
| *G01N 33/50* | (2006.01) |
| *G01N 33/543* | (2006.01) |

(52) U.S. Cl.
CPC ......... *C12Q 1/6818* (2013.01); *C12N 5/0062* (2013.01); *C12Q 1/6804* (2013.01); *C12Q 1/6837* (2013.01); *C12Q 1/6841* (2013.01); *C12Q 1/6876* (2013.01); *G01N 33/5023* (2013.01); *G01N 33/5088* (2013.01); *G01N 33/54306* (2013.01); *C12Q 2600/158* (2013.01); *G01N 2458/10* (2013.01)

(58) Field of Classification Search
CPC .................................................. C12Q 1/6818
See application file for complete search history.

(56) References Cited

U.S. PATENT DOCUMENTS

| | | |
|---|---|---|
| 4,574,729 A | 3/1986 | Wells |
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |
| 5,130,238 A | 7/1992 | Malek |
| 5,183,053 A | 2/1993 | Yeh et al. |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,559,032 A | 9/1996 | Pomeroy |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,716,825 A | 2/1998 | Hancock et al. |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,958,775 A | 9/1999 | Wickstrrom |
| 5,965,443 A | 10/1999 | Reznikoff et al. |
| 6,013,440 A | 1/2000 | Lipshutz |
| 6,027,889 A | 2/2000 | Barany et al. |
| 6,060,240 A | 5/2000 | Kamb et al. |
| 6,083,761 A | 7/2000 | Kedar et al. |
| 6,130,073 A | 10/2000 | Eggerding |
| 6,136,592 A | 10/2000 | Leighton |

(Continued)

FOREIGN PATENT DOCUMENTS

| | | |
|---|---|---|
| CN | 1680604 | 10/2005 |
| CN | 1981188 | 6/2007 |

(Continued)

OTHER PUBLICATIONS

Lahiani et al. (2018, J. Pathology Informatics, vol. 9(1), pp. 1-8). (Year: 2018).*
Al-Ani et al. (2018, PLOS One, vol. 13(10), pp. 1-13). (Year: 2018).*
Asp et al., "Spatially Resolved Transcriptomes—Next Generation Tools for Tissue Exploration," Bioessays, Oct. 2020, 42(10):e1900221, 16 pages.
Balakrishnan et al., "Flap endonuclease 1," Annu Rev Biochem., Jun. 2013, 82:119-138.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.

(Continued)

*Primary Examiner* — Anoop K Singh
*Assistant Examiner* — David A Montanari
(74) *Attorney, Agent, or Firm* — Fish & Richardson P.C.

(57) ABSTRACT

Provided herein are methods for simultaneous spatio-temporal measurement of gene expression and cellular activity.

28 Claims, 42 Drawing Sheets

(56) References Cited

U.S. PATENT DOCUMENTS

| | | | |
|---|---|---|---|
| 6,143,496 A | 11/2000 | Brown | |
| 6,153,389 A | 11/2000 | Haarer | |
| 6,159,736 A | 12/2000 | Reznikoff et al. | |
| 6,165,714 A | 12/2000 | Lane et al. | |
| 6,210,891 B1 | 4/2001 | Nyren | |
| 6,210,894 B1 | 4/2001 | Brennan | |
| 6,214,587 B1 | 4/2001 | Dattagupta | |
| 6,251,639 B1 | 6/2001 | Kurn | |
| 6,258,568 B1 | 7/2001 | Nyren | |
| 6,266,459 B1 | 7/2001 | Walt | |
| 6,268,148 B1 | 7/2001 | Barany et al. | |
| 6,274,320 B1 | 8/2001 | Rothberg | |
| 6,291,180 B1 | 9/2001 | Chu | |
| 6,300,063 B1 | 10/2001 | Lipshutz et al. | |
| 6,309,824 B1 | 10/2001 | Drmanac | |
| 6,337,472 B1 | 1/2002 | Garner et al. | |
| 6,344,316 B1 | 2/2002 | Lockhart | |
| 6,355,431 B1 | 3/2002 | Chee | |
| 6,368,801 B1 | 4/2002 | Faruqi | |
| 6,401,267 B1 | 6/2002 | Drmanac | |
| 6,404,907 B1 | 6/2002 | Gilchrist | |
| 6,432,360 B1 | 8/2002 | Church et al. | |
| 6,485,982 B1 | 11/2002 | Charlton | |
| 6,503,713 B1 | 1/2003 | Rana | |
| 6,506,561 B1 | 1/2003 | Cheval et al. | |
| 6,544,732 B1 | 4/2003 | Chee | |
| 6,565,727 B1 | 5/2003 | Shenderov | |
| 6,573,043 B1 | 6/2003 | Cohen et al. | |
| 6,579,695 B1 | 6/2003 | Lambalot | |
| 6,620,584 B1 | 9/2003 | Chee | |
| 6,632,641 B1 | 10/2003 | Brennan | |
| 6,673,620 B1 | 1/2004 | Loeffler | |
| 6,737,236 B1 | 5/2004 | Pieken et al. | |
| 6,770,441 B2 | 8/2004 | Dickinson | |
| 6,773,566 B2 | 8/2004 | Shenderov | |
| 6,773,886 B2 | 8/2004 | Kaufman | |
| 6,787,308 B2 | 9/2004 | Balasubramanian | |
| 6,797,470 B2 | 9/2004 | Barany et al. | |
| 6,800,453 B2 | 10/2004 | Labaer | |
| 6,812,005 B2 | 11/2004 | Fan et al. | |
| 6,828,100 B1 | 12/2004 | Ronaghi | |
| 6,833,246 B2 | 12/2004 | Balasubramanian | |
| 6,852,487 B1 | 2/2005 | Barany et al. | |
| 6,859,570 B2 | 2/2005 | Walt | |
| 6,864,052 B1 | 3/2005 | Drmanac | |
| 6,867,028 B2 | 3/2005 | Janulaitis | |
| 6,872,816 B1 | 3/2005 | Hall et al. | |
| 6,875,572 B2 | 4/2005 | Prudent et al. | |
| 6,890,741 B2 | 5/2005 | Fan et al. | |
| 6,897,023 B2 | 5/2005 | Fu | |
| 6,911,132 B2 | 6/2005 | Pamula | |
| 6,911,345 B2 | 6/2005 | Quake | |
| 6,913,881 B1 | 7/2005 | Aizenstein et al. | |
| 6,913,921 B2 | 7/2005 | Fischer | |
| 6,942,968 B1 | 9/2005 | Dickinson et al. | |
| 6,969,488 B2 | 11/2005 | Bridgham | |
| 6,977,033 B2 | 12/2005 | Becker | |
| 7,001,792 B2 | 2/2006 | Sauer et al. | |
| 7,011,944 B2 | 3/2006 | Prudent et al. | |
| 7,052,244 B2 | 5/2006 | Fouillet | |
| 7,057,026 B2 | 6/2006 | Barnes | |
| 7,083,980 B2 | 8/2006 | Reznikoff et al. | |
| 7,098,041 B2 | 8/2006 | Kaylor et al. | |
| 7,115,400 B1 | 10/2006 | Adessi | |
| 7,118,883 B2 | 10/2006 | Inoue | |
| 7,163,612 B2 | 1/2007 | Sterling | |
| 7,166,431 B2 | 1/2007 | Chee et al. | |
| 7,192,735 B2 | 3/2007 | Lambalot | |
| 7,211,414 B2 | 5/2007 | Hardin | |
| 7,223,371 B2 | 5/2007 | Hayenga et al. | |
| 7,244,559 B2 | 7/2007 | Rothberg | |
| 7,255,994 B2 | 8/2007 | Lao | |
| 7,258,976 B2 | 8/2007 | Mitsuhashi | |
| 7,264,929 B2 | 9/2007 | Rothberg | |
| 7,282,328 B2 | 10/2007 | Kong et al. | |
| 7,297,518 B2 | 11/2007 | Quake | |
| 7,328,979 B2 | 2/2008 | Decre | |
| 7,329,492 B2 | 2/2008 | Hardin | |
| 7,358,047 B2 | 4/2008 | Hafner et al. | |
| 7,361,488 B2 | 4/2008 | Fan et al. | |
| 7,378,242 B2 | 5/2008 | Hurt | |
| 7,393,665 B2 | 7/2008 | Brenner | |
| 7,405,281 B2 | 7/2008 | Xu | |
| 7,407,757 B2 | 8/2008 | Brenner | |
| 7,462,449 B2 | 12/2008 | Quake | |
| 7,499,806 B2 | 3/2009 | Kermani et al. | |
| 7,501,245 B2 | 3/2009 | Quake | |
| 7,537,897 B2 | 5/2009 | Brenner | |
| 7,547,380 B2 | 6/2009 | Velev | |
| 7,563,576 B2 | 7/2009 | Chee | |
| 7,579,153 B2 | 8/2009 | Brenner | |
| 7,582,420 B2 | 9/2009 | Oliphant et al. | |
| 7,595,883 B1 | 9/2009 | El Gamal | |
| 7,601,492 B2 | 10/2009 | Fu et al. | |
| 7,601,498 B2 | 10/2009 | Mao | |
| 7,608,434 B2 | 10/2009 | Reznikoff et al. | |
| 7,611,869 B2 | 11/2009 | Fan | |
| 7,635,566 B2 | 12/2009 | Brenner | |
| 7,641,779 B2 | 1/2010 | Becker | |
| 7,666,612 B2 | 2/2010 | Johnsson | |
| 7,674,752 B2 | 3/2010 | He | |
| 7,709,198 B2 | 5/2010 | Luo et al. | |
| 7,776,547 B2 | 8/2010 | Roth | |
| 7,776,567 B2 | 8/2010 | Mao | |
| 7,785,869 B2 | 8/2010 | Belgrader et al. | |
| 7,803,943 B2 | 9/2010 | Mao | |
| 7,858,321 B2 | 12/2010 | Glezer | |
| 7,888,009 B2 | 2/2011 | Barany et al. | |
| 7,892,747 B2 | 2/2011 | Barany et al. | |
| 7,914,981 B2 | 3/2011 | Barany et al. | |
| 7,955,794 B2 | 6/2011 | Shen et al. | |
| 7,960,119 B2 | 6/2011 | Chee | |
| 8,003,354 B2 | 8/2011 | Shen et al. | |
| 8,076,063 B2 | 12/2011 | Fan | |
| 8,092,784 B2 | 1/2012 | Mao | |
| 8,148,068 B2 | 4/2012 | Brenner | |
| 8,206,917 B2 | 6/2012 | Chee | |
| 8,278,034 B2 | 10/2012 | Muraca | |
| 8,288,103 B2 | 10/2012 | Oliphant | |
| 8,337,851 B2 | 12/2012 | Aukerman | |
| 8,343,500 B2 | 1/2013 | Wraith | |
| 8,383,338 B2 | 2/2013 | Kitzman | |
| 8,460,865 B2 | 6/2013 | Chee | |
| 8,481,257 B2 | 7/2013 | Van Eijk | |
| 8,481,292 B2 | 7/2013 | Casbon | |
| 8,481,698 B2 | 7/2013 | Lieberman et al. | |
| 8,507,204 B2 | 8/2013 | Pierce et al. | |
| 8,551,710 B2 | 10/2013 | Bernitz et al. | |
| 8,568,979 B2 | 10/2013 | Stuelpnagel et al. | |
| 8,586,310 B2 | 11/2013 | Mitra | |
| 8,597,891 B2 | 12/2013 | Barany et al. | |
| 8,603,743 B2 | 12/2013 | Liu et al. | |
| 8,604,182 B2 | 12/2013 | Luo et al. | |
| 8,614,073 B2 | 12/2013 | Van Eijk | |
| 8,624,016 B2 | 1/2014 | Barany et al. | |
| 8,637,242 B2 | 1/2014 | Shen | |
| 8,685,889 B2 | 4/2014 | Van Eijk | |
| 8,741,564 B2 | 6/2014 | Seligmann | |
| 8,741,606 B2 | 6/2014 | Casbon | |
| 8,778,849 B2 | 7/2014 | Bowen | |
| 8,785,353 B2 | 7/2014 | Van Eijk | |
| 8,790,873 B2 | 7/2014 | Namsaraev et al. | |
| 8,809,238 B2 | 8/2014 | Livak et al. | |
| 8,815,512 B2 | 8/2014 | Van Eijk | |
| 8,835,358 B2 | 9/2014 | Fodor | |
| 8,865,410 B2 | 10/2014 | Shendure | |
| 8,906,626 B2 | 12/2014 | Oliphant et al. | |
| 8,911,945 B2 | 12/2014 | Van Eijk | |
| 8,936,912 B2 | 1/2015 | Mitra | |
| 8,951,726 B2 | 2/2015 | Luo et al. | |
| 8,951,728 B2 | 2/2015 | Rasmussen | |
| 8,951,781 B2 | 2/2015 | Reed | |
| 9,005,891 B2 | 4/2015 | Sinicropi et al. | |
| 9,005,935 B2 | 4/2015 | Belyaev | |

(56) References Cited

U.S. PATENT DOCUMENTS

| | | |
|---|---|---|
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,598 B2 | 6/2016 | Chee |
| 9,376,716 B2 | 6/2016 | Van Eijk |
| 9,376,719 B2 | 6/2016 | Van Eijk |
| 9,404,156 B2 | 8/2016 | Hicks |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,518,980 B2 | 12/2016 | Logger et al. |
| 9,557,330 B2 | 1/2017 | Siciliano et al. |
| 9,574,230 B2 | 2/2017 | Van Eijk |
| 9,582,877 B2 | 2/2017 | Fu |
| 9,593,365 B2 | 3/2017 | Frisen et al. |
| 9,598,728 B2 | 3/2017 | Barany et al. |
| 9,657,335 B2 | 5/2017 | Van Eijk |
| 9,670,542 B2 | 6/2017 | Van Eijk |
| 9,702,004 B2 | 7/2017 | Van Eijk |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,950 B2 | 2/2018 | Church et al. |
| 9,902,991 B2 | 2/2018 | Sinicropi et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,011,872 B1 | 7/2018 | Belgrader et al. |
| 10,023,907 B2 | 7/2018 | Van Eijk |
| 10,030,261 B2 | 7/2018 | Frisen et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,273,541 B2 | 4/2019 | Hindson et al. |
| 10,405,750 B2 | 9/2019 | Wang et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,550,429 B2 | 2/2020 | Harada et al. |
| 10,633,648 B2 | 4/2020 | Seelig et al. |
| 10,724,078 B2 | 7/2020 | Van Driel et al. |
| 10,774,372 B2 | 9/2020 | Chee et al. |
| 10,774,374 B2 | 9/2020 | Frisen et al. |
| 10,787,701 B2 | 9/2020 | Chee |
| 10,829,803 B2 | 11/2020 | Terbreggen et al. |
| 10,913,975 B2 | 2/2021 | So et al. |
| 10,914,730 B2 | 2/2021 | Chee et al. |
| 10,927,403 B2 | 2/2021 | Chee et al. |
| 11,008,607 B2 | 5/2021 | Chee |
| 11,046,996 B1 | 6/2021 | Chee et al. |
| 11,067,567 B2 | 7/2021 | Chee |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 2001/0055764 A1 | 12/2001 | Empendocles et al. |
| 2002/0040275 A1 | 4/2002 | Cravatt et al. |
| 2002/0045272 A1 | 4/2002 | McDevitt et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0150909 A1 | 10/2002 | Stuelpnagel |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0087232 A1 | 5/2003 | Christians |
| 2003/0113713 A1 | 6/2003 | Glezer |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0175947 A1 | 9/2003 | Liu et al. |
| 2003/0190744 A1 | 10/2003 | McGarry et al. |
| 2003/0205632 A1 | 11/2003 | Kim et al. |
| 2003/0215936 A1 | 11/2003 | Kallioniemi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2004/0033499 A1 | 2/2004 | Ilsley et al. |
| 2004/0050699 A1 | 3/2004 | Goncalves |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0112442 A1 | 6/2004 | Maerkl |
| 2004/0121456 A1 | 6/2004 | Fischer |
| 2004/0219588 A1 | 11/2004 | Furuta |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0179746 A1 | 8/2005 | Roux et al. |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239192 A1 | 10/2005 | Nasarabadi et al. |
| 2005/0260653 A1 | 11/2005 | LaBaer |
| 2005/0266417 A1 | 12/2005 | Barany et al. |
| 2006/0039823 A1 | 2/2006 | Yamakawa et al. |
| 2006/0046313 A1 | 3/2006 | Roth |
| 2006/0063160 A1 | 3/2006 | West et al. |
| 2006/0084078 A1 | 4/2006 | Zhao |
| 2006/0105352 A1 | 5/2006 | Qiao et al. |
| 2006/0134669 A1 | 6/2006 | Casasanta |
| 2006/0164490 A1 | 7/2006 | Kim et al. |
| 2006/0188901 A1 | 8/2006 | Barnes et al. |

(56) References Cited

U.S. PATENT DOCUMENTS

| | | |
|---|---|---|
| 2006/0194331 A1 | 8/2006 | Pamula et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0023292 A1 | 2/2007 | Kim et al. |
| 2007/0026430 A1 | 2/2007 | Andersen et al. |
| 2007/0036511 A1 | 2/2007 | Lundquist et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0116612 A1 | 5/2007 | Williamson |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0166725 A1 | 7/2007 | McBride et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0169089 A1 | 7/2009 | Hunt et al. |
| 2009/0170713 A1 | 7/2009 | van Eijk et al. |
| 2009/0192044 A1 | 7/2009 | Fouillet |
| 2009/0197326 A1 | 8/2009 | El Gamal et al. |
| 2009/0233802 A1 | 9/2009 | Bignell et al. |
| 2009/0239232 A1 | 9/2009 | Kurn |
| 2009/0253163 A1 | 10/2009 | Xie et al. |
| 2009/0253581 A1 | 10/2009 | van Eijk et al. |
| 2009/0253582 A1 | 10/2009 | Pena et al. |
| 2009/0283407 A1 | 11/2009 | Van Eijk |
| 2009/0289184 A1 | 11/2009 | Deininger |
| 2009/0291854 A1 | 11/2009 | Wiesinger-Mayr et al. |
| 2009/0312193 A1 | 12/2009 | Kim et al. |
| 2009/0321262 A1 | 12/2009 | Adachi et al. |
| 2010/0009871 A1 | 1/2010 | Reed et al. |
| 2010/0035249 A1 | 2/2010 | Hayashizaki et al. |
| 2010/0069263 A1 | 3/2010 | Shendure et al. |
| 2010/0096266 A1 | 4/2010 | Kim et al. |
| 2010/0105052 A1 | 4/2010 | Drmanac et al. |
| 2010/0111768 A1 | 5/2010 | Banerjee et al. |
| 2010/0120097 A1 | 5/2010 | Matz et al. |
| 2010/0120098 A1 | 5/2010 | Grunenwald et al. |
| 2010/0126862 A1 | 5/2010 | Sabin et al. |
| 2010/0129874 A1 | 5/2010 | Mitra et al. |
| 2010/0145037 A1 | 6/2010 | Brive et al. |
| 2010/0151511 A1 | 6/2010 | Gereenizer et al. |
| 2010/0173384 A1 | 7/2010 | Johnsson et al. |
| 2010/0184614 A1 | 7/2010 | Ye et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0267590 A1 | 10/2010 | Grudzien et al. |
| 2010/0273219 A1 | 10/2010 | May et al. |
| 2010/0282617 A1 | 11/2010 | Rothberg et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0048951 A1 | 3/2011 | Wu |
| 2011/0059436 A1 | 3/2011 | Hardin et al. |
| 2011/0111409 A1 | 5/2011 | Sinicropi et al. |
| 2011/0152111 A1 | 6/2011 | Illumina |
| 2011/0177518 A1 | 7/2011 | Kartalov et al. |
| 2011/0223613 A1 | 9/2011 | Gut |
| 2011/0244448 A1 | 10/2011 | Shirai et al. |
| 2011/0245101 A1 | 10/2011 | Chee et al. |
| 2011/0245111 A1 | 10/2011 | Chee |
| 2011/0287435 A1 | 11/2011 | Gruuenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0160683 A1 | 6/2012 | Ye et al. |
| 2012/0195810 A1 | 8/2012 | Cohen et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0252702 A1 | 10/2012 | Muratani et al. |
| 2012/0258871 A1 | 10/2012 | Kozlov et al. |
| 2012/0270305 A1 | 10/2012 | Reed et al. |
| 2012/0279954 A1 | 11/2012 | Ceremony et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0035239 A1 | 2/2013 | Kong et al. |
| 2013/0065768 A1 | 3/2013 | Zheng et al. |
| 2013/0065788 A1 | 3/2013 | Sigal et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0260372 A1 | 10/2013 | Buermann et al. |
| 2013/0261019 A1 | 10/2013 | Lin et al. |
| 2013/0296174 A1 | 11/2013 | Peumans |
| 2013/0302801 A1 | 11/2013 | Asbury et al. |
| 2013/0338042 A1 | 12/2013 | Shen et al. |
| 2014/0065609 A1 | 3/2014 | Hicks et al. |
| 2014/0066318 A1 | 3/2014 | Frisen et al. |
| 2014/0121118 A1 | 5/2014 | Warner |
| 2014/0155295 A1 | 6/2014 | Hindson et al. |
| 2014/0274731 A1 | 9/2014 | Raymond et al. |
| 2014/0323330 A1 | 10/2014 | Glezer et al. |
| 2014/0342921 A1 | 11/2014 | Weiner |
| 2015/0000854 A1 | 1/2015 | Gann-Fetter |
| 2016/0019337 A1 | 1/2016 | Roberts et al. |
| 2016/0024576 A1 | 1/2016 | Chee |
| 2016/0033496 A1 | 2/2016 | Chou et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0299165 A1 | 10/2016 | Zhou |
| 2016/0333403 A1 | 11/2016 | Chee |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0166962 A1 | 6/2017 | van Eijk et al. |

(56) References Cited

U.S. PATENT DOCUMENTS

| | | |
|---|---|---|
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0242020 A1 | 8/2017 | Yamauchi et al. |
| 2017/0283860 A1 | 10/2017 | Kool et al. |
| 2017/0335410 A1 | 11/2017 | Driscoll et al. |
| 2017/0343545 A1 | 11/2017 | Hadrup et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0074039 A1 | 3/2018 | Soper et al. |
| 2018/0094316 A1 | 4/2018 | Oliphant et al. |
| 2018/0095067 A1 | 4/2018 | Huff et al. |
| 2018/0104694 A1 | 4/2018 | Huff et al. |
| 2018/0104964 A1 | 4/2018 | Uemura et al. |
| 2018/0105808 A1 | 4/2018 | Mikkelsen et al. |
| 2018/0112261 A1 | 4/2018 | Van Driel et al. |
| 2018/0114316 A1 | 4/2018 | Lele et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0217094 A1 | 8/2018 | Herr et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0251825 A1 | 9/2018 | Stoeckius et al. |
| 2018/0251833 A1 | 9/2018 | Daugharthy et al. |
| 2018/0282803 A1 | 10/2018 | Belgrader et al. |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0346970 A1 | 12/2018 | Chang |
| 2019/0055594 A1 | 2/2019 | Samusik et al. |
| 2019/0085324 A1 | 3/2019 | Regev et al. |
| 2019/0085383 A1 | 3/2019 | Church et al. |
| 2019/0135774 A1 | 5/2019 | Orbai |
| 2019/0145982 A1 | 5/2019 | Chee et al. |
| 2019/0155835 A1 | 5/2019 | Daugharthy et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0194709 A1 | 6/2019 | Church et al. |
| 2019/0203275 A1* | 7/2019 | Frisén ............... C12N 15/1065 |
| 2019/0218276 A1 | 7/2019 | Regev et al. |
| 2019/0233880 A1 | 8/2019 | Mir |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0330617 A1 | 10/2019 | Church et al. |
| 2019/0352708 A1 | 11/2019 | Gaige et al. |
| 2019/0360043 A1 | 11/2019 | Pham et al. |
| 2019/0367969 A1 | 12/2019 | Belhocine et al. |
| 2020/0002764 A1 | 1/2020 | Belgrader et al. |
| 2020/0010891 A1 | 1/2020 | Beechem et al. |
| 2020/0024641 A1 | 1/2020 | Nolan et al. |
| 2020/0048690 A1 | 2/2020 | Chee |
| 2020/0063195 A1 | 2/2020 | Chee |
| 2020/0063196 A1 | 2/2020 | Chee |
| 2020/0080136 A1 | 3/2020 | Zhang et al. |
| 2020/0109443 A1 | 4/2020 | Chee |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0298241 A1 | 9/2020 | Kabaha et al. |
| 2020/0299757 A1 | 9/2020 | Chee et al. |
| 2020/0325531 A1 | 10/2020 | Chee |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0049294 A1 | 2/2022 | Uytingco et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |

(56) References Cited

U.S. PATENT DOCUMENTS

| | | | |
|---|---|---|---|
| 2022/0195422 | A1 | 6/2022 | Gallant et al. |
| 2022/0195505 | A1 | 6/2022 | Frisen et al. |
| 2022/0196644 | A1 | 6/2022 | Chee |
| 2022/0213526 | A1 | 7/2022 | Frisen et al. |
| 2022/0241780 | A1 | 8/2022 | Tentori et al. |
| 2022/0267844 | A1 | 8/2022 | Ramachandran Iyer et al. |
| 2022/0282329 | A1 | 9/2022 | Chell et al. |
| 2022/0290217 | A1 | 9/2022 | Frenz et al. |
| 2022/0290219 | A1 | 9/2022 | Chee |
| 2022/0298560 | A1 | 9/2022 | Frisen et al. |

FOREIGN PATENT DOCUMENTS

| | | |
|---|---|---|
| CN | 101221182 | 7/2008 |
| CN | 108949924 | 12/2018 |
| EP | 0961110 | 12/1999 |
| EP | 1782737 | 5/2007 |
| EP | 1878502 | 1/2008 |
| EP | 1910562 | 4/2008 |
| EP | 1923471 | 5/2008 |
| EP | 2002017 | 12/2008 |
| EP | 2292788 | 3/2011 |
| EP | 2302070 | 3/2011 |
| EP | 2881465 | 6/2015 |
| EP | 3013984 | 5/2016 |
| EP | 3511423 | 7/2019 |
| EP | 3541956 | 9/2019 |
| JP | 2007-014297 | 1/2007 |
| JP | 2007-074967 | 3/2007 |
| JP | 2009-036694 | 2/2009 |
| RU | 2270254 | 2/2006 |
| WO | WO 1989/010977 | 11/1989 |
| WO | WO 1991/006678 | 5/1991 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1999/063385 | 12/1999 |
| WO | WO 2000/17390 | 3/2000 |
| WO | WO 2000/024940 | 5/2000 |
| WO | WO 2001/06012 | 1/2001 |
| WO | WO 2001/009363 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/024952 | 3/2002 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2003/106973 | 12/2003 |
| WO | WO 2004/015080 | 2/2004 |
| WO | WO 2004/028955 | 4/2004 |
| WO | WO 2004/067759 | 8/2004 |
| WO | WO 2004/108268 | 12/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/117541 | 11/2006 |
| WO | WO 2006/124771 | 11/2006 |
| WO | WO 2007/030373 | 3/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/120241 | 10/2007 |
| WO | WO 2007/123744 | 11/2007 |
| WO | WO 2007/139766 | 12/2007 |
| WO | WO 2007/145612 | 12/2007 |
| WO | WO 2008/069906 | 6/2008 |
| WO | WO 2008/157801 | 12/2008 |
| WO | WO 2009/032167 | 3/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2011/008502 | 1/2011 |
| WO | WO 2011/062933 | 5/2011 |
| WO | WO 2011/068088 | 6/2011 |
| WO | WO 2011/094669 | 8/2011 |
| WO | WO 2011/102903 | 8/2011 |
| WO | WO 2012/048341 | 4/2012 |
| WO | WO 2012/049316 | 4/2012 |
| WO | WO 2012/058096 | 5/2012 |
| WO | WO 2012/071428 | 5/2012 |
| WO | WO 2012/083225 | 6/2012 |
| WO | WO 2012/129242 | 9/2012 |
| WO | WO 2012/159089 | 11/2012 |
| WO | WO 2012/168003 | 12/2012 |
| WO | WO 2013/123442 | 8/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/130576 | 8/2014 |
| WO | WO 2014/142841 | 9/2014 |
| WO | WO 2014/144713 | 9/2014 |
| WO | WO 2014/152397 | 9/2014 |
| WO | WO 2014/210223 | 12/2014 |
| WO | WO 2014/210225 | 12/2014 |
| WO | WO 2015/069374 | 5/2015 |
| WO | WO 2015/161173 | 10/2015 |
| WO | WO 2016/057552 | 4/2016 |
| WO | WO 2016/138496 | 9/2016 |
| WO | WO 2016/138500 | 9/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/048871 | 3/2017 |
| WO | WO 2017/075265 | 5/2017 |
| WO | WO 2017/075293 | 5/2017 |
| WO | WO 2017/112957 | 6/2017 |
| WO | WO 2017/096158 | 7/2017 |
| WO | WO 2017/124101 | 7/2017 |
| WO | WO 2017/144338 | 8/2017 |
| WO | WO 2017/147483 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/045181 | 3/2018 |
| WO | WO 2018/064640 | 4/2018 |
| WO | WO 2018/075436 | 4/2018 |
| WO | WO 2018/075693 | 4/2018 |
| WO | WO 2018/085599 | 5/2018 |
| WO | WO 2018/091676 | 5/2018 |
| WO | WO 2018/102577 | 6/2018 |
| WO | WO 2018/136856 | 7/2018 |
| WO | WO 2018/144582 | 8/2018 |
| WO | WO 2018/148471 | 8/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/104337 | 5/2019 |
| WO | WO 2019/113457 | 6/2019 |
| WO | WO 2019/113533 | 6/2019 |
| WO | WO 2019/126313 | 6/2019 |
| WO | WO-2019113457 A1 * | 6/2019 ............ B01L 3/5085 |
| WO | WO 2019/140201 | 7/2019 |
| WO | WO 2019/140334 | 7/2019 |
| WO | WO 2019/165318 | 8/2019 |

(56) References Cited

FOREIGN PATENT DOCUMENTS

| | | |
|---|---|---|
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/112604 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/176788 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/243579 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/119320 | 6/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/216708 | 10/2021 |
| WO | WO 2021/225900 | 11/2021 |
| WO | WO 2021/236625 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061152 | 3/2022 |
| WO | WO 2022/087273 | 4/2022 |
| WO | WO 2022/098810 | 5/2022 |
| WO | WO 2022/099037 | 5/2022 |
| WO | WO 2022/109181 | 5/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |

OTHER PUBLICATIONS

Blair et al., "Microarray temperature optimization using hybridization kinetics," Methods Mol Biol., 2009, 529:171-96.

Bolotin et al., "MiXCR: software for comprehensive adaptive immunity profiling," Nat Methods., May 2015, 12(5):380-1.

Chen et al., "Parallel single nucleotide polymorphism genotyping by surface invasive cleavage with universal detection," Anal Chem., Apr. 2005, 77(8):2400-5.

Chester et al., "Dimethyl sulfoxide-mediated primer Tm reduction: a method for analyzing the role of renaturation temperature in the polymerase chain reaction," Anal Biochem, Mar. 1993, 209(2):284-90.

Ciaccio et al., "Systems analysis of EGF receptor signaling dynamics with microwestern arrays," Nat Methods, Feb. 2010, 7(2):148-55.

Gerard et al., "Excess dNTPs minimize RNA hydrolysis during reverse transcription," Biotechniques, Nov. 2002, 33(5):984, 986, 988, 990.

Hessner et al., "Genotyping of factor V G1691A (Leiden) without the use of PCR by invasive cleavage of oligonucleotide probes," Clin Chem., Aug. 2000, 46(8 Pt 1):1051-6.

Hoffman et al., "Formaldehyde crosslinking: a tool for the study of chromatin complexes," J Biol Chem., Oct. 2015, 290(44):26404-11.

Hughes et al., "Microfluidic Western blotting," PNAS, Dec. 2012, 109(52):21450-21455.

Jucá et al., "Effect of dimethyl sulfoxide on reverse transcriptase activity," Braz. J. Med. Biol. Res., Mar. 1995, 28(3):285-90.

Kalantari et al., "Deparaffinization of formalin-fixed paraffin-embedded tissue blocks using hot water instead of xylene," Anal Biochem., Aug. 2016, 507:71-3.

Krzywkowski el al., "Chimeric padlock and iLock probes for increased efficiency of targeted RNA detection," RNA, Jan. 2019, 25(1):82-89.

Krzywkowski et al., "Fidelity of RNA templated end-joining by chlorella virus DNA ligase and a novel iLock assay with improved direct RNA detection accuracy," Nucleic Acids Research, Oct. 2017, 45(18):e161, 9 pages.

Lyamichev et al., "Invader assay for SNP genotyping," Methods Mol Biol., 2003, 212:229-40.

Lyamichev et al., "Polymorphism identification and quantitative detection of genomic DNA by invasive cleavage of oligonucleotide probes," Nat Biotechnol., Mar. 1999, 17(3):292-6.

Nam et al., "Somatic mutations and cell identity linked by Genotyping of Transcriptomes," Nature, Jul. 2019, 571(7765):355-360.

Nilsson et al., "RNA-templated DNA ligation for transcript analysis," Nucleic Acids Res., Jan. 2001, 29(2):578-81.

Olivier, "The Invader assay for SNP genotyping," Mutat. Res., Jun. 2005, 573(1-2):103-110.

Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.

Perocchi et al., "Antisense artifacts in transcriptome microarray experiments are resolved by actinomycin D," Nucleic Acids Res., 2007, 35(19):e128, 7 pages.

Picelli et al., "Full-length RNA-seq from single cells using Smart-seq2," Nat Protoc., Jan. 2014, 9(1):171-81.

Schouten et al., "Relative quantification of 40 nucleic acid sequences by multiplex ligation-dependent probe amplification," Nucleic Acids Res., Jun. 2002, 30(12):e57, 13 pages.

Singh et al., "High-throughput targeted long-read single cell sequencing reveals the clonal and transcriptional landscape of lymphocytes," Nat Commun., Jul. 2019, 10(1):3120, 13 pages.

Sountoulidis et al., "SCRINSHOT, a spatial method for single-cell resolution mapping of cell states in tissue sections," PLoS Biol., Nov. 2020, 18(11):e3000675, 32 pages.

Spiess et al., "A highly efficient method for long-chain cDNA synthesis using trehalose and betaine," Anal. Biochem., Feb. 2002, 301(2):168-74.

Sutherland et al., "Utility of formaldehyde cross-linking and mass spectrometry in the study of protein-protein interactions," J. Mass Spectrom., Jun. 2008, 43(6):699-715.

Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.

(56) References Cited

OTHER PUBLICATIONS

Tu et al., "TCR sequencing paired with massively parallel 3' RNA-seq reveals clonotypic T cell signatures," Nature Immunology, Dec. 2019, 20(12):1692-1699.
Valley et al., "Optoelectronic tweezers as a tool for parallel single-cell manipulation and stimulation," IEEE Trans Biomed Circuits Syst., Dec. 2009, 3(6):424-31.
Vázquez Bernat et al., "High-Quality Library Preparation for NGS-Based Immunoglobulin Germline Gene Inference and Repertoire Expression Analysis," From Immunol., Apr. 2019, 10:660, 12 pages.
Wu et al., "RollFISH achieves robust quantification of single-molecule RNA biomarkers in paraffin-embedded tumor tissue samples," Commun Biol., Nov. 2018, 1:209, 8 pages.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Morlan et al., "Selective depletion of rRNA enables whole transcriptome profiling of archival fixed tissue," PLoS One, Aug. 2012, 7(8):e42882, 8 pages.
U.S. Appl. No. 60/416,118, filed Oct. 3, 2002, Fan et al.
U.S. Appl. No. 61/267,363, filed Dec. 7, 2009, Fan el al.
U.S. Appl. No. 61/839,313, filed Jun. 25, 2013, Chee et al.
U.S. Appl. No. 61/839,320, filed Jun. 25, 2013, Chee et al.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif). GeneChip, 2000, 104 pages.
[No Author Listed], "Microarray technologies have excellent possibilities in genomics-related researches," Science Tools From Amersbam Pharmacia Biotech, 1998, 3(4): 8 pages (with English Translation).
[No Author Listed], "Proseek® Multiplex 96x96 User Manual," Olink Proteomics. Olink Bioscience, Uppsala, Sweden, 2017, 20 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/ 5UJrN0cH17rEk0UXwd19It/e54d99fb08a8f1500aba503005a04a56/ CG000238_VisiumSpatialTissue OptimizationUserGuide_RevD. pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/ 3GGIfH3RWpdlbFVhalpexR/8baa08d9007157592b65b2cdc7130990/ CG000239_VisiumSpatialGeneExpression_UserGuide_RevD.pdf, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/ 3GGIfH3RWpdlbFVhalpexR/8baa08d9007157592b65b2cdc7130990/ CG000239_VisiumSpatialGeneExpression_UserGuide_RevD. pdf>, 70 pages.
10xGenomics.com, [online],"Visium Spatial Gene Expression Reagent Kits—Tissue Optimization—User Guide," Jul. 2020, retrieved on May 25, 2021, retrieved from URL<https://assets.ctfassets.net/ an68im79xiti/5UJrN0cHI7rEk0UXwd19It/ e54d99fb08a8f1500aba503005a04a56/CG000238_ VisiumSpatialTissueOptimizationUserGuide_RevD.pdf, 42 pages.
Adamson et al., "A Multiplexed Single-Cell CRISPR Screening Platform Enables Systematic Dissection of the Unfolded Protein Response," Cell, Dec. 2016, 167(7):1867-1882.e21.
Adessi et al., "Solid phase DNA amplification: characterisation of primer attachment and amplification mechanisms," Nucl. Acids Res., 2000, 28(20):E87, 8 pages.

Adiconis et al., "Comparative analysis of RNA sequencing methods for degraded or low-input samples," Nat Methods, Jul. 2013, 10(7):623-9.
Affymetrix, "GeneChip Human Genome UI33 Set," retrieved from the Internet: on the World Wide Web at affymetrix.com/support/ technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetnx.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Altaras et al., "Production and formulation of adenovirus vectors," Adv Biochem Eng Biotechnol., Nov. 2005, 99:193-260.
Anderson et al., "Microarrayed Compound Screening to Identify Activators and Inhibitors of AMP-Activated Protein Kinase," J. of Biomolecular Screening, 2004, 9:112.
Andersson et al., "Analysis of protein expression in cell microarrays: a tool for antibody-based proteomics.," J Histochem Cytochem., 4(12): 1413-1423, 2006.
Andor.com [online], "Discover new ways of seeing," Next Generation Digital Illumination, Mosaic 3, 2020, 11 pages.
Andresen et al., "Helicase-dependent amplification: use in OnChip amplification and potential for point-of-care diagnostics," Expert Rev Mol Diagn., Oct. 2009, 9(7):645-650.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al, "2D-PCR: a method of mapping DNA in tissue sections," Lab Chip, 2009, 9(24):3526-34.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Azioune et al., "Simple and rapid process for single cell micropatterning," Lab Chip, Jun. 2009, 9(11):1640-1642.
Bains et al., "A novel method for nucleic acid sequence determination," Journal of Theoretical Biology, 1988, 135(3), 303-7.
Bajar et al., "A Guide to Fluorescent Protein FRET Pairs," Sensors (Basel), Sep. 2016, 16(9):1488, 24 pages.
Bando et al., "Comparative Evaluation of Genetically Encoded Voltage Indicators," Cell Reports, Jan. 2019, 26(3):802-813.e1-e4.
Barnes, "PCR amplification of up to 35-kb DNA with high fidelity and high yield from lambda bacteriophage templates," Proc. Natl. Acad. Sci USA, 1994, 91(6):2216-2220.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bielas et al., "Quantification of random genomic mutations," Nat. Methods, 2005, 2(4):285-290.
Biosyntagma.com, [online], "Resolving Heterogeneity One Cell at a Time," available on or before Apr. 21, 2017, via Internet Archive: Wayback Machine URL<https://web.archive.org/web/20170421212315/

(56) References Cited

OTHER PUBLICATIONS http/www.biosyntagma.com/, retrieved on Sep. 29, 2021, URL<http://www.biosyntagma.com/>, 3 pages.
Birney et al., "Identification and analysis of functional elements in 1% of the human genome by the ENCODE pilot project," Nature, 2007, 447(7146):799-816.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bootman et al., "Loading fluorescent Ca2+ indicators into living cells," Cold Spring Harb Protoc., Feb. 2013, 2013(2):122-5.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space fortranscriptomics," Nature Reviews Genetics, 2016, 17(8):436-7.
Burgess, "Finding structure in gene expression," Nature Reviews Genetics, 2018, 19(5):249, 1 page.
Burton et al., "Coverslip Mounted-Immersion Cycled in Situ RT-PCR for the Localization of mRNA in Tissue Sections," Biotechniques, 1998, 24(1):92-100.
Butler et al., "Integrating single-cell transcriptomic data across different conditions, technologies, and species," Nat Biotechnol., Jun. 2018, 36(5):411-420.
Calvert, "Materials science. Printing cells," Science, Oct. 2007, 318(5848):208-209.
Carter et al., "Stabilization of an optical microscope to 0.1 nm in three dimensions," Applied Optics, 2007, 46:421-427.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12):1878-1882.
Chen et al., "Expansion microscopy," Science, 2015, 347(6221):543-548.
Chen et al., "Geometric control of cell life and death" Science, May 1997, 276(5317):1425-1428.
Chen et al., "Nanoscale imaging of RNA with expansion microscopy," Nat Methods, Aug. 2016, 13(8):679-84.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.

Chen et al., "Spatially resolved, highly multiplexed RNA profiling in single cells," Science, 2015, 348(6233):aaa6090, 21 pages.
Chen et al., "µCB-seq: microfluidic cell barcoding and sequencing for high-resolution imaging and sequencing of single cells," Lab Chip, Nov. 2020, 20(21):3899-3913.
Chen et al., "ATAC-see reveals the accessible genome by transposase-mediated imaging and sequencing," Nature Methods, Dec. 2016, 13(12):1013-1020.
Cheng et al., "Sensitive Detection of Small Molecules by Competitive Immunomagnetic-Proximity Ligation Assay," Anal Chem, 2012, 84:2129-2132.
Chrisey et al., "Covalent attachment of synthetic DNA to self-assembled monolayer films," Nucleic Acids Res., Aug. 1996, 24(15):3031-9.
Chung et al., "Imaging single-cell signaling dynamics with a deterministic high-density single-cell trap array," Anal Chem, Sep. 2011, 83(18):7044-7052.
Chung et al., "Structural and molecular interrogation of intact biological systems," Nature, May 2013, 497:332-337.
Clevers, "Modeling Development and Disease with Organoids," Cell, Jun. 2016, 165(7):1586-1597.
Cockroft et al., "A single-molecule nanopore device detects DNA polymerase activity with single-nucleotide resolution," J Am Chem Soc., Jan. 2008, 130(3):818-20.
Collins et al., "Two-dimensional single-cell patterning with one cell per well driven by surface acoustic waves," Nature Communications, Nov. 2015, 6:8686, 11 pages.
Constantine et al., "Use of genechip high-density oligonucleotide arrays for gene expression monitoring," Life Sceience News, Amersham Life Science, 1998, pp. 11-14.
Corces et al., "An improved ATAC-seq protocol reduces background and enables interrogation of frozen tissues," Nat. Methods, 2017, 14(10):959-962.
Corces et al., "Lineage-specific and single-cell chromatin accessibility charts human hematopoiesis and leukemia evolution," Nature Genetics, Oct. 2016, 48(10):1193-1203.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cujec et al., "Selection of v-abl tyrosine kinase substrate sequences from randomized peptide and cellular proteomic libraries using mRNA display," Chemistry and Biology, 2002, 9(2):253-264.
Curtis et al., "Adhesion of cells to polystyrene surfaces," J Cell Biol., Nov. 1983, 97(5):1500-1506.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Darmanis et al., "ProteinSeq: High-Performance Proteomic Analyses by Proximity, Ligation and Next Generation Sequencing," PLos One, 2011, 6(9):e25583, 10 pages.
Datlinger et al., "Pooled CRISPR screening with single-cell transcriptome readout," Nat Methods, Mar. 2017, 14(3):297-301.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
De Clercq et al., "Approved Antiviral Drugs over the Past 50 Years," Clinical Microbiology Reviews, Jul. 2016, 29(3):695-747.
De Clercq, "A 40-year journey in search of selective antiviral chemotherapy," Annu Rev Pharmacol Toxicol., 2011, 51:1-24.
Deamer et al., "Characterization of nucleic acids by nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Deng et al., "Spatial Epigenome Sequencing at Tissue Scale and Cellular Level," BioRxiv, Mar. 2021, 40 pages.

(56) References Cited

OTHER PUBLICATIONS

Dhindsa et al., "Virtual Electrowetting Channels: Electronic Liquid Transport with Continuous Channel Functionality," Lab Chip, 2010, 10:832-836.
Digitimer.com, [online], "Perfusion Chamber," 2021, retrieved on Dec. 29, 2021, retrieved from URL<https://www.digitimer.com/?s=perfusion+chamber&dgwt-wcas-search-submit=&post_type=product&dgwt_wcas=1>, 4 pages.
Ding et al., "On-chip manipulation of single microparticles, cells, and organisms using surface acoustic waves," PNAS, Jul. 2012, 109(28):11105-11109.
Dixit et al., "Perturb-Seq: Dissecting Molecular Circuits with Scalable Single-Cell RNA Profiling of Pooled Genetic Screens," Cell, Dec. 2016, 167(7):1853-1866.e17.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Drulev et al., "Quantification of rare allelic variants from pooled genomic DNA," Nat. Methods, 2009, 6(4):263-65.
Duncan et al., "Affinity chromatograph of a sequence-specific DNA binding protein using Teflon-linked oligonucleotides," Anal. Biochem., 1988, 169(1):104-108.
Eberwine et al., "Analysis of gene expression in single live neurons," Proc. Natl. Acad. Sci., USA 89, 3010-3014, 1992.
Eberwine, "Amplification of mRN A populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Ekins et al., "Microarrays: their origins and applications," Trends in Biotechnology, Jun. 1999, 17(6):217-218.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Falconnet et al., "Surface engineering approaches to micropattern surfaces for cell-based assays," Biomaterials, Jun. 2006, 27(16):3044-3063.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fluidigm, "Hyperion Imaging System: Visualize a new path forward," Feb. 2018, retrieved from URL <https://www.fluidigm.com/binaries/content/documents/fluidigm/search/hippo%3Aresultset/hyperion-imaging-system-br-400326/fluidigm%3Afile>, 27 pages.
Fluidigm, "Immuno-Oncology Research with the Hyperion Imaging System: A high-parameter imaging solution at subcellular resolution to characterize the immune repertoire in the tumor microenvironment," Apr. 2018, retrieved from URL <https://www.fluidigm.com/binaries/content/documents/fluidigm/fsearch/hippo%3Aresultset/application-note-immuno-oncology-research-with-the-hyperion%E2%84%A2-imaging-system/fluidigm%3Afile>, 6 pages.
Fluidigm, "Immuno-Oncology Research with the Hyperion Imaging System: A high-parameter imaging solution at subcellular resolution to characterize the immune repertoire in the tumor microenvironment," Aug. 2018, retrieved from URL <https://www.fluidigm.com/binaries/content/documents/fluidigm/marketing/immuno-oncology-research-with-the-hyperion-imaging-system-appnote-400332/immuno-oncology-research-with-the-hyperion-imaging-system-appnote-400332/fluidigm%Afile>, 6 pages.
Fluidigm, "Maxpar Antibodies for Imaging Mass Cytometry," Mar. 2018, retrieved from URL <https://www.fluidigm.com/binaries/content/documents/fluidigm/search/hippo%3Aresultset/hyperion-antibodies-for-imaging-mass-cytometry-br-101-7115/fluidigm%3Afile>, 2 pages.
Fodor et al., "Light-directed, spatially addressable parallel chemical synthesis," Science, 1995, 251(4995):767-773.
Folch et al., "Microfabricated elastomeric stencils for micropatterning cell cultures," J Biomed Mater Res, Nov. 2000, 52(2):346-353.
Forcucci et al., "All-plastic miniature fluorescence microscope for point-of-care readout of bead-based bioassays.," J. Biomed Opt., 2015, 20(10):105010, 15 pages.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Counting individual DNA molecules by the stochastic attachment, of diverse labels," PNAS, 2011, 108(22):9026-9031.
Fu et al., "Repeat subtraction-mediated sequence capture from a complex genome," Plant J., Jun. 2010, 62(5):898-909.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gao et al., "Q&A: Expansion microscopy", BMC Biology, 15:50, 9 pages, 2017.
Gene@arrays[online], BeatArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Giam et al., "Scanning probe-enabled nanocombinatorics define the relationship between fibronectin feature size and stem cell fate," PNAS, Mar. 2012, 109(12):4377-4382.
Gierahn et al., "Seq-Well: portable, low-cost RNA sequencing of single cells at high throughput," ResearchSquare, 2017, 53 pages.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pages 38 pages.
Grokhovsky, "Specificity of DNA cleavage by ultrasound," Molecular Biology, 2006, 40(2):276-283.
Gross et al., "Technologies for Single-Cell Isolation," Int. J Mol. Sci., Jul. 2015, 16(8):16897-16919.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.

(56) References Cited

OTHER PUBLICATIONS

Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Habib et al., "Div-Seq: Single-nucleus RNA-Seq reveals dynamics of rare adult newborn neurons," Science, Aug. 2016, 353(6302):925-8.
Habib et al., "Massively parallel single-nucleus RNA-seq with DroNc-seq," Nat Methods, Oct. 2017, 14(10):955-958.
Hahnke et al., "Striptease on glass: validation of an improved stripping procedure for in situ microarrays," J Biotechnol., Jan. 2007, 128(1):1-13.
Hammond et al., "Profiling cellular protein complexes by proximity ligation with dual tag microarray readout," PLoS One, 2012, 7(7):e40405, 9 pages.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Heaton et al., "Souporcell: Robust clustering of single cell RNAseq by genotype and ambient RNA inference without reference genotypes," bioRxiv, Sep. 2019, 22 pages.
Hedskog et al., "Dynamics of HIV-1 Quasispecies during Antiviral Treatment Dissected using Ultra-Deep Pyrosequencinq," PLoS One, 5(7): e111345, 2010.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Hoyer et al., "Electrostatic spraying: a novel technique for preparation of polymer coatings on electrodes," Anal Chem, Nov. 1996, 68(21):3840-4.
Hu et al., "Dissecting Cell-Type Composition and Activity-Dependent Transcriptional State in Mammalian Brains by Massively Parallel Single-Nucleus RNA-Seq," Mol Cell., Dec. 2017, 68(5):1006-1015.
Hu et al., "High reproducibility using sodium hydroxide-stripped long oligonucleotide DNA microarrays," Biotechniques, Jan. 2005, 38(1):121-4.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ibidi.com, [online], "Cell Culture Under Flow," 2021, retrieved on Dec. 28, 2021, retrieved from URL<https://ibidi.com/content/category/25-cell-culture-under-flow>, 13 pages.
Ichikawa et al., "In vitro transposition of transposon Tn3," J Biol. Chem., Nov. 1990, 265(31):18829-32, Abstract.
Jabara et al., Accurate sampling and deep sequencing of the HIV-I protease gene using a Primer ID. PNAS 108(50); 20166-20171, 2011.
Jaitin et al., "Dissecting Immune Circuits by Linking CRISPR-Pooled Screens with Single-Cell RNA-Seq," Cell, Dec. 2016, 167(7):1883-1896.e15.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen, "Technical review: In situ hybridization," Anat Rec (Hoboken)., Aug. 2014, 297(8):1349-1353.
Jones et al., "Comparative lesion sequencing provides insights into tumor evolution," Proc. Natl. Acad. Sci. USA, 105(11): 4283-4288, 2008.
Kap et al., "Histological assessment of PAXgene tissue fixation and stabilization reagents," PLOS One, 2011, 6:27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Korlach et al., "Selective aluminum passivation for targeted immobilization of single DNA polymerase molecules in zero-mode waveguide nanostructures," Proc. Natl. Acad. Sci. USA 105, 1176-1181, 2008.
Korsunsky et al., "Fast, sensitive and accurate integration of single-cell data with Harmony," Nat. Methods, Dec. 2019, 16(12):289-1296.
Kozlov et al., "A highly scalable peptide-based assay system for proteomics," PLoS One, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1)95-100.
Lacar et al., "Nuclear RNA-seq of single neurons reveals molecular signatures of activation," Nat Commun., Apr. 2016, 7:11022, 12 pages.
Lage et al., "Whole genome analysis of genetic alterations in small DNA samples using hyperbranched strand displacement amplification and array-CGH," Genome Research, 2003, 13(2):294-307.
Lake et al., "Neuronal subtypes and diversity revealed by single-nucleus RNA sequencing of the human brain," Science, Jun. 2016, 352(6293):1586-90.
Lampe et al., "A purified mariner transposase is sufficient, to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.

(56) References Cited

OTHER PUBLICATIONS

Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Laurell et al., "Chip integrated strategies for acoustic separation and manipulation of cells and particles," Chem. Soc. Rev., Mar. 2007, 36(3):492-506.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Lee et al., "XYZeq: Spatially resolved single-cell RNA sequencing reveals expression heterogeneity in the tumor microenvironment," Science Advances, 2021, 7:eabg4755, 1-14.
Leriche et al., "Cleavable linkers in chemical biology," Bioorganic & Medicinal Chemistry, 2012, 20:571-582.
Levene et al., "Zero-Mode Waveguides for Single-Molecule Analysis at High Concentrations," Science 299, 682-686, 2003.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "DNA molecules and configurations in a solid-state nanopore microscope," Nat Mater., Sep. 2003, 2(9):611-5.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Liberali et al., "Single-cell and multivariate approaches in genetic perturbation screens," Nat Rev Genet., Jan. 2015, 16(1):18-32.
Lin et al., "Highly multiplexed imaging of single cells using a high-throughput cyclic immunofluorescence method," Nat Commun., Sep. 2015, 6:8390, 7 pages.
Lin et al., "Microfluidic cell trap array for controlled positioning of single cells on adhesive micropatterns," Lab Chip, Feb. 2013, 13(4):714-721.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Lizardi et al., "Mutation detection and single-molecule counting using isothermal rolling-circle amplification," Nat. Genet., 1998, 19(3):225-232.
Lovatt et al., "Transcriptome in vivo analysis (TIVA) of spatially defined single cells in live tissue," Nature Methods, 2013, 11(2):190-196.
Lu et al., "A microfluidic electroporation device for cell lysis," Lab Chip., Jan. 2005, 5(1):23-29.
Lund et al., "Assessment of methods for covalent, binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lundquist et al., "Parallel confocal detection of single molecules in real time," Opt. Lett. 33, 1026-1028, 2008.
Lyck et al., "Immunohistochemical markers for quantitative studies of neurons and glia in human neocortex," J Histochem Cytochem, 2008, 56(3):201-21.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Macosko et al., "Highly Parallel Genome-wide Expression Profiling of Individual Cells Using Nanoliter Droplets," Cell, 2015, 161:1202-1214.
Marx, "Method of the Year: spatially resolved transcriptomics," Nature Methods, 2021, 18(1):9-14.
Mauleon et al., "Precise Spatial and Temporal Control of Oxygen within In Vitro Brain Slices via Microfluidic Gas Channels," PLoS One, Aug. 2012, 7(8):e43309, 9 pages.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele el al., "Mapping cis- and trans-chromatin interaction networks using chromosome conformation capture (3C)," Methods Mol Biol., 2009, 464:105-21.
Miller et al., "Basic concepts of microarrays and potential applications in clinical microbiology," Clinical Microbiology Reviews, 2009, 22(4):611-633.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mizusawa et al., "A bacteriophage lambda vector for cloning with BamHI and Sau3A," Gene, 1982, 20(3):317-322.
Mortazavi et al., "Mapping and quantifying mammalian transcriptomes by RNA-Seq," Nature Methods, 5(7): 621-8, 2008.
Motea et al., "Terminal deoxynucleotidyl transferase: the story of a misguided DNA polymerase," Biochim Biophys Acta., May 2010, 1804(5):1151-66.
Nakamura et al., "Biocompatible inkjet printing technique for designed seeding of individual living cells," Tissue Eng, Nov. 2005, 11(11-12):1658-1666.
Nandakumar et al., "How an RNA Ligase Discriminates RNA versus DNA Damage," Molecular Cell, 2004, 16:211-221.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/, 2 pages.
Ng et al., "Gene identification signature (GIS) analysis for transcriptome characterization and genome annotation," Nature Methods, 2005, 2(2)105-111.
Nichols et al., "RNA Ligases," Curr Protoc Mol Biol., Oct. 2008, 84(1):3.15.1-3.15.4.
Nikiforov et al., "The use of 96-well polystyrene plates for DNA hybridization-based assays: an evaluation of different approaches to oligonucleotide immobilization," Anal Biochem, May 1995, 227(1):201-9.

(56) References Cited

OTHER PUBLICATIONS

Niklas et al., "Selective permeabilization for the high-throughput measurement of compartmented enzyme activities in mammalian cells," Anal Biochem, Sep. 2011, 416(2):218-27.
Nowak et al., "Entering the Postgenome Era," Science, 1995, 270(5235)368-71.
Ohtsubo et al., "Bacterial insertion sequences," Curr Top Microbiol Immunol., 1996, 204:1-26.
Ostuni et al., "Patterning Mammalian Cells Using Elastomeric Membranes," Langmuir, Aug. 2000, 16(20):7811-7819.
Pandey et al., "Inhibition of terminal deosynucleotidyl transferase by adenine dinucleotides. Unique inhibitory action of Ap5A," FEBS Lett., Mar. 1987, 213(1):204-8.
Park et al., "Cancer gene therapy using adeno-associated virus vectors," Front Biosci., Jan. 2008, 13:2653-59.
Park et al., "Single cell trapping in larger microwells capable of supporting cell spreading and proliferation," Microfluid Nanofluid, 2010, 8:263-268.
Pathak et al., "Present and Future Prospect of Small Molecule & Related Targeted Therapy Against Human Cancer," Vivechan Int J Res., 2018, 9(1):36-49.
Patil et al., "DNA-based therapeutics and DNA delivery systems: a comprehensive review," AAPS J, Apr. 2005, 7(1):E61-77.
PCT International Search Report and Written Opinion in International Appln. No. PCT/US2021/033405, dated Aug. 18, 2021, 21 pages.
PCT Invitation to Pay Additional Fees in International Appln. No. PCT/US2021/033405, dated Aug. 26, 2021, 16 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Plasterk. "The Tcl/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Primebioscience.com, [online], "Brain Slice Systems, Recording Chambers, Stage Adapters, Temperature Controller," 2017, retrieved on Dec. 28, 2021, retrieved from URL<http://primebioscience.com/pb-applications/brain-slice-systems-recording-chambers-stage-adapterstemperature-controller/>, 7 pages.
U.S. Appl. No. 61/267,363, filed Dec. 7, 2009, 33 pages.
Raab et al., "Human tRNA genes function as chromatin insulators," EMBO J., Jan. 2012, 31(2):330-50.
Ranki et al., "Sandwich hybridization as a convenient method for the detection of nucleic acids in crude samples," Gene, 1983, 21(1-2):77-85.
Razonable, "Antiviral drugs for viruses other than human immunodeficiency virus," Mayo Clinic Proceedings, Oct. 2011, 86(10):1009-26.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Rettig et al., "Large-scale single-cell trapping and imaging using microwell arrays," Anal Chem, Sep. 2005, 77(17):5628-5634.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Rosenthal et al., "Cell patterning chip for controlling the stem cell microenvironment," Biomaterials, Jul. 2007, 28(21):3208-3216.
Rountenberg et al., "Microfluidic probe: a new tool for integrating microfluidic environments and electronic wafer-orobina," Lab Chip, Oct. 2009, 10: 123-127.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Satpathv et al., "Massively parallel single-cell chromatin landscapes of human immune cell development and intratumoral T cell exhaustion," Nat Biotechnol., Aug. 2019, 37(8):925-936.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schweitzer et al., "Multiplexed protein profiling on microarrays by rolling-circle amplification," Nature Biotechnology, Apr. 2002, 20(4):359-365.
Setliff et al., High-Throughput Mapping of B Cell Receptor Sequences to Antigen Specificity, Cell, 2019, 179:1636-1646.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Shirai et al., "Novel Tools for Analyzing Gene Expressions in Single Cells," The 5th International Workshop on Approaches to Single-Cell Analysis, The University of Tokyo, Mar. 3-4, 2011, 1 page.
Simonis et al., "Nuclear organization of active and inactive chromatin domains uncovered by chromosome conformation capture-on-chip (4C)," Nat Genet., Nov. 2006, 38(11):1348-54.
Skene et al., "An efficient targeted nuclease strategy for high-resolution mapping of DNA binding sites," Elife, Jan. 2017, 6:e21856, 35 pages.
Soni and Meller, "Progress toward ultrafast DNA sequencing using solid-state nanopores," Clin Chem., 2007, 53: 1996-2001.
Spille et al., "Labelling and imaging of single endogenous messenger RNA particles in vivo," Journal of Cell Science, Oct. 2015, 128(20):3695-3706.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jun. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.

(56) References Cited

OTHER PUBLICATIONS

Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Stuart et al., "Comprehensive Integration of Single-Cell Data," Cell, Jun. 2019, 177(7):1888-1902.
Suh et al., "A simple soft lithographic route to fabrication of poly(ethylene glycol) microstructures for protein and cell patterning," Biomaterials, Feb. 2004, 25(3):557-563.
Tai et al., "Replication-competent retrovirus vectors for cancer gene therapy," Front Biosci., Jan. 2008, 13:3083-95.
Tan et al., "Parylene peel-off arrays to probe the role of cell-cell interactions in tumour angiogenesis," Integr Biol (Camb), Oct. 2009, 1(10):587-594.
Tang et al., "RNA-Seq analysis to capture the transcriptome landscape of a single cell.," Nat Protoc., 5: 516-35, 2010.
Taniguchi et al., "Quantitative analysis of gene expression in a single cell by qPCR," Nature Methods, 6, pp. 503-506, 2009.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Trejo et al., "Extraction-free whole transcriptome gene expression analysis of FFPE sections and histology-directed subareas of tissue," PLoS One, Feb. 2019, 14(2):e0212031, 22 pages.
Tseng et al., "Magnetic nanoparticle-mediated massively parallel mechanical modulation of single-cell behavior," Nat Methods, Nov. 2012, 9(11):1113-1119.
Twyman et al., "Techniques Patents for SNP Genotyping," Pharmacogenomics, Jan. 2003, 4(1):67-79.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Velculescu et al., "Serial analysis of gene expression," Science, Oct. 1995, 270(5235):484-7.
Vermesh et al., "High-density, multiplexed patterning of cells at single-cell resolution for tissue engineering and other applications," Angew Chem Int Ed Engl, Aug. 2011, 50(32):7378-7380.
Vickovic et al., "High-definition spatial transcriptomics for in situ tissue profiling," Nat Methods, Oct. 2019, 16(10):987-990.
Vickovic et al., "Massive and parallel expression profiling using microarrayed single-cell sequencing," Nature Communications, 2016, 7(13182):1-9.

Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "Imaging-based pooled CRISPR screening reveals regulators of lncRNA localization," Proc Natl Acad Sci USA, May 2019, 116(22):10842-10851.
Wang et al., "Single cell analysis: the new frontier in 'omics,'" Trends Biotechnol., 28: 281-90, 2010.
Wang et al., "High-fidelity mRNA amplification for gene profiling," Nature Biotechnology, Apr. 2000, 18(4):457-459.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization." Genes and Development, Oct. 1994, 8(19):2363-2374.
Wheeler et al., "Microfluidic device for single-cell analysis," Analytical Chemistry, Jul. 2003, 75(14):3581-3586.
Wiedmann et al., "Ligase chain reaction (LCR)—overview and applications," PCR Methods Appl., Feb. 1994, 3(4):S51-64.
Williams, "RAC reviews serious adverse event associated with AAV therapy trial," Mol Ther., Dec. 2007, 15(12):2053-54.
Wilson et al., "New transposon delivery plasmids for insertional mutagenesis in Bacillus anthracis," J Microbiol Methods, Dec. 2007, 71(3):332-5.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Wood et al., "Single cell trapping and DNA damage analysis using microwell arrays," PNAS, Jun. 2010, 107(22):10008-10013.
Worthington et al., "Cloning of random oligonucleotides to create single-insert plasmid libraries," Anal Biochem, 2001, 294(2):169-175.
Wright et al., "Reusable, reversibly sealable parylene membranes for cell and protein patterning," J Biomed Mater Res A., May 2008, 85(2):530-538.
Wu et al.. "Detection DNA Point Mutation with Rolling-Circle Amplification Chip," IEEE, 2010 4th International Conference on Bioinformatics and Biomedical Engineering, Jun. 2010, 4 pages.
Wu et al., "RNA imaging in living mice enabled by an in vivo hybridization chain reaction circuit with a tripartite DNA probe," Chemical Science, Oct. 2019, 11(1):62-69.
Xu et al., "Organoid technology and applications in cancer research," Journal of Hematology & Oncology, Sep. 2018, 11(1):116.
Xu et al., "Voltage imaging with genetically encoded indicators," Curr Opin Chem Biol., Aug. 2017, 39:1-10.
Yamauchi et al., "Subcellular western blotting of single cells," Microsyst Nanoeng., 2017, 3:16079, 9 pages.
Yeakley et al, "Profiling alternative splicing on fiber-optic arrays," Nature biotechnology, 2002, 20:353-358.
Yeakley et al., "A trichostatin A expression signature identified by TempO-Seq targeted whole transcriptome profiling," PLoS One, May 2017, 12(5):e0178302, 22 pages.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.

(56) References Cited

OTHER PUBLICATIONS

Yoda et al., "Site-specific gene expression analysis using an automated tissue micro-dissection punching system," Sci Rep., Jun. 2017, 7(1):4325, 11 pages.
Yusof et al., "Inkjet-like printing of single-cells," Lab Chip, Jul. 2011, 11(14):2447-2454.
Zhang et al., "Archaeal RNA ligase from thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Block-Cell-Printing for live single-cell printing," PNAS, Feb. 2014, 111(8):2948-2953.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a Smart approach for full-length cDNA library construction," Biotechniques, Apr. 2001, 30(4):892-897.
10xGenomics.com, [online], "Visimn Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Cruz et al., "Methylation in cell-free DNA for early cancer detection," Ann Oncol., Jun. 2018, 29(6):1351-1353.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Ke et al., "In situ sequencing for RNA analysis in preserved tissue and cells," Nat Methods., Sep. 2013, Supplementary Materials, 29 pages.
Miner et al., "Molecular barcodes detect redundancy and contamination in hairpin-bisulfite PCR," Nucleic Acids Res., Sep. 2004, 32(17):e135, 4 pages.
Wang et al., "Tagmentation-based whole-genome bisulfite sequencing," Nature Protocols, Oct. 2013, 8(10):2022-2032.
Ali et al., "Patterns of Immune Infiltration in Breast Cancer and Their Clinical Implications: A Gene-Expression-Based Retrospective Study," PLoS Med., Dec. 2016, 13(12):e1002194, 24 pages.
Bocková et al., "Advances in Surface Plasmon Resonance Imaging and Microscopy and Their Biological Applications," Annu Rev Anal Chem (Palo Alto Calif)., Jun. 2019, 12(1):151-176.
Cheng, "The Contrast Formation in Optical Microscopy," Handbook of Biological Confocal Microscopy, 2006, Chapter 8, pp. 162-206.
Colin et al., "Enzyme engineering in biomimetic compartments," Curr Opin Struct Biol., Aug. 2015, 33:42-51.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Lakhin et al., "Aptamers: problems, solutions and prospects," Acta Naturae, Oct. 2013, 5(4):34-43.
Le Reste et al., "Characterization of dark quencher chromophores as nonfluorescent acceptors for single-molecule FRET," Biophysical Journal, Jun. 2012, 102(11):2658-2668.
Marras, "Selection of fluorophore and quencher pairs for fluorescent nucleic acid hybridization probes," Methods Mol Biol., 2006, 335:3-16.
Massey et al., "Fluorescence resonance energy transfer (FRET) for DNA biosensors: FRET pairs and Förster distances for various dye-DNA conjugates," Anal Chim Acta., May 2006, 568(1-2):181-9.
Mattheyses et al., "Imaging with total internal reflection fluorescence microscopy for the cell biologist," J Cell Sci., Nov. 2010, 123(Pt 21):3621-3628.
Niedringhaus et al., "Landscape of next-generation sequencing technologies," Anal Chem., Jun. 2011, 83(12):4327-41.
Novusbio.com [online], "Lightning-Link® APC Antibody Labeling Kit," 2022, retrieved on Apr. 26, 2022, retrieved from URL<https://www.novusbio.com/products/lightning-link-r-apc-kit_705-0030>, 3 pages.
Piston et al., "Fluorescent protein FRET: the good, the bad and the ugly," Trends Biochem Sci., Sep. 2007, 32(9):407-14.
Qiu et al., "Combination probes with intercalating anchors and proximal fluorophores for DNA and RNA detection," Nucleic Acids Research, Sep. 2016, 44(17):e138, 12 pages.
San Paulo et al., "High-resolution imaging of antibodies by tapping-mode atomic force microscopy: attractive and repulsive tip-sample interaction regimes," Biophys J., Mar. 2000, 78(3):1599-1605.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Sekar et al., "Fluorescence resonance energy transfer (FRET) microscopy imaging of live cell protein localizations," J Cell Biol., Mar. 2003, 160(5):629-33.
Shrestha et al., "Understanding FRET as a research tool for cellular studies," Int J Mol Sci., Mar. 2015, 16(4):6718-56.
Tawfik et al., "Man-made cell-like compartments for molecular evolution," Nat Biotechnol., Jul. 1998, 16(7):652-6.
Toseland, "Fluorescent labeling and modification of proteins," J Chem Biol., Apr. 2013, 6(3):85-95.
Vallejo et al., "Fluorescence-Activated Droplet Sorting for Single-Cell Directed Evolution," ACS Synth Biol., Jun. 2019, 8(6):1430-1440.
Zhao et al., "Isothermal Amplification of Nucleic Acids," Chemical Reviews, Nov. 2015, 115(22):12491-12545.
Zheng, "Spectroscopy-based quantitative fluorescence resonance energy transfer analysis," Methods Mol Biol., 2006, 337:65-77.
U.S. Appl. No. 16/353,937, filed Mar. 14, 2019, Frisen et al.
U.S. Appl. No. 17/707,189, filed Mar. 29, 2022, Chell et al.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Boulé et al., "Terminal deoxynucleotidyl transferase indiscriminately incorporates ribonucleotides and deoxyribonucleotides," J Biol Chem., Aug. 2001, 276(33):31388-93.
Burgess, "Spatial transcriptomics coming of age," Nat Rev Genet., Jun. 2019, 20(6):317, 1 page.
Caliari et al., "A practical guide to hydrogels for cell culture," Nat Methods., Apr. 2016, 13(5):405-14.
Dalma-Weiszhausz et al., "The affymetrix GeneChip platform: an overview," Methods Enzymol., 2006, 410:3-28.
Evers et al., "The effect of formaldehyde fixation on RNA: optimization of formaldehyde adduct removal," J Mol Diagn., May 2011, 13(3):282-8.
Gansauge et al., "Single-stranded DNA library preparation from highly degraded DNA using T4 DNA ligase," Nucleic Acids Res., Jun. 2017, 45(10):e79, 10 pages.
Hafner et al., "Identification of microRNAs and other small regulatory RNAs using cDNA library sequencing," Methods, Jan. 2008, 44(1):3-12.
Hanauer et al., "Separation of nanoparticles by gel electrophoresis according to size and shape," Nano Lett., Sep. 2007, 7(9):2881-5.

(56) References Cited

OTHER PUBLICATIONS

Hattersley et al., "Development of a microfluidic device for the maintenance and interrogation of viable tissue biopsies," Lab Chip., Nov. 2008, 8(11):1842-6.
Ho et al., "Characterization of an ATP-Dependent DNA Ligase Encoded by Chlorella Virus PBCV-1," Journal of Virology, Mar. 1997, 71(3):1931-1937.
Hsuih et al., "Novel, Ligation-Dependent PCR Assay for Detection of Hepatitis C Virus in Serum," Journal of Clinical Microbiology, Mar. 1996, 34(3):501-507.
Hughes et al., "Highly Efficient, Massively-Parallel Single-Cell RNA-Seq Reveals Cellular States and Molecular Features of Human Skin Pathology," bioRxiv, Jul. 2019, 51 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Kumar et al., "Template-directed oligonucleotide strand ligation, covalent intramolecular DNA circularization and catenation using click chemistry," J Am Chem Soc., May 2007, 129(21):6859-64.
Lou et al., "A review of room temperature storage of biospecimen tissue and nucleic acids for anatomic pathology laboratories and biorepositories," Clin Biochem., Mar. 2014, 47(4-5):267-73.
Lykidis et al., "Novel zinc-based fixative for high quality DNA, RNA and protein analysis," Nucleic Acids Res., Jun. 2007, 35(12):e85, 10 pages.
Madissoon et al., "scRNA-seq assessment of the human lung, spleen, and esophagus tissue stability after cold preservation," Genome Biol., Dec. 2019, 21(1):1, 16 pages.
Miller et al., "Chapter 11—Solid and Suspension Microarrays for Microbial Diagnostics," Methods in Microbiology, 2015, 42:395-431.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Nadji et al., "Immunohistochemistry of tissue prepared by a molecular-friendly fixation and processing system," Appl Immunohistochem Mol Morphol., Sep. 2005, 13(3):277-82.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ozsolak et al., "Digital transcriptome profiling from attomole-level RNA samples," Genome Res., Apr. 2010, 20(4):519-25.
Passow et al., "RNAlater and flash freezing storage methods nonrandomly influence observed gene expression in RNAseq experiments," bioRxiv, Jul. 2018, 28 pages.
Porreca et al., "Polony DNA sequencing," Curr Protoc Mol Biol., Nov. 2006, Chapter 7, Unit 7.8, pp. 7.8.1-7.8.22.
Slomovic et al., "Addition of poly(A) and poly(A)-rich tails during RNA degradation in the cytoplasm of human cells," Proc Natl Acad Sci USA, Apr. 2010, 107(16):7407-12.
Taylor et al., "Microfluidic local perfusion chambers for the visualization and manipulation of synapses," Neuron., Apr. 2010, 66(1):57-68, 25 pages.
Thomas et al., "A chamber for the perfusion of in vitro tissue with multiple solutions," J. Neurophysiol., Apr. 2013, 110:269-277.
Toy et al., "A Simple Plastic Perfusion Chamber for Continuous Maintenance and Cinematography of Tissue Cultures," Experimental Cell Research, 1958, 14:97-103.
Ulery et al., "Biomedical Applications of Biodegradable Polymers," J Polym Sci B Polym Phys., Jun. 2011, 49(12):832-864.
Vandenbroucke et al., "Quantification of splice variants using real-time PCR," Nucleic Acids Research, 2001, 29(13):e68, 7 pages.
Vickovic et al., "SM-Omics: An automated Platform for High-Throughput Spatial Multi-Omics," bioRxiv, Oct. 2020, 40 pages.
Wang et al., "Optimization of Process Conditions for Infected Animal Tissues by Alkaline Hydrolysis Technology," Procedia Environmental Sciences, 2016, 31:366-374.
Wohnhaas et al., "DMSO cryopreservation is the method of choice to preserve cells for droplet-based single-cell RNA sequencing," Scientific Reports, Jul. 2019, 9(1):10699, 14 pages.
Zhang et al., "Genome-wide open chromatin regions and their effects on the regulation of silk protein genes in Bombyx mori," Sci Rep., Oct. 2017, 7(1):12919, 9 pages.
Mulder et al., "CapTCR-seq: hybrid capture for T-cell receptor repertoire profiling," Blood Advances, Dec. 2018, 2(23):3506-3514.

\* cited by examiner

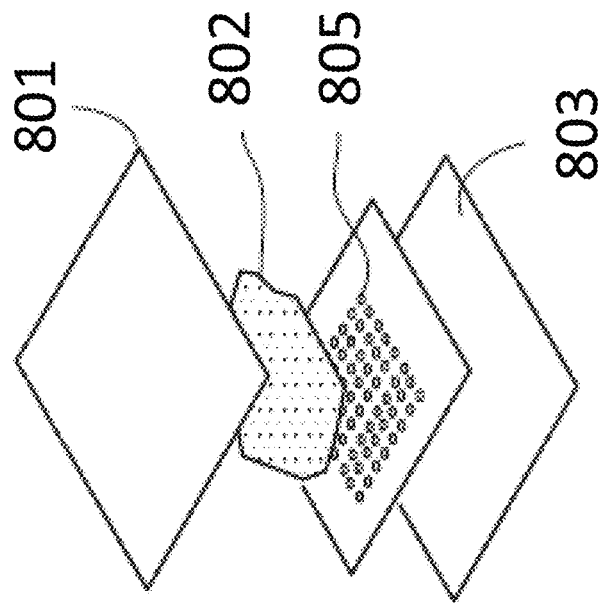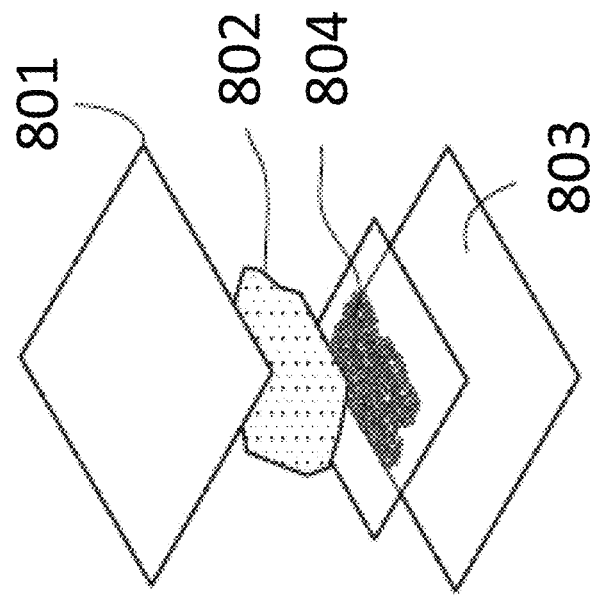
FIG. 8A

12A: Vibratome
12B: Generation of live tissue sections

FIG. 12C: Perfusion chamber

12D: Assembled onto a microscope for electrical and optical recordings

Top Differentially Expressed Genes (Only genes in the all-vs-all comparison with expression ≥ 0.3 and p-value ≤ 0.05 are shown)

| Condition_type | Condition1 | Feature_ID | Feature_name | Condition2 | Mean1 | Mean2 | log2FC | adj_p_value |
|---|---|---|---|---|---|---|---|---|
| Drug Treatment | Linsitinib | ENSG00000130032 | PRRG3 | Osimertinib | 0.820 | 0.233 | 1.815 | 0.000 |
| Drug Treatment | Linsitinib | ENSG00000179862 | CITED4 | Osimertinib | 0.472 | 0.177 | 1.415 | 0.000 |
| Drug Treatment | Linsitinib | ENSG00000185567 | AHNAK2 | Osimertinib | 0.634 | 0.294 | 1.108 | 0.000 |
| Drug Treatment | Linsitinib | ENSG00000107281 | NPDC1 | Osimertinib | 0.397 | 0.187 | 1.082 | 0.000 |
| Drug Treatment | Linsitinib | ENSG00000005884 | ITGA3 | Osimertinib | 2.171 | 1.034 | 1.070 | 0.000 |
| Drug Treatment | Untreated | ENSG00000146250 | PRSS35 | Linsitinib | 0.394 | 0.047 | 3.065 | 0.000 |
| Drug Treatment | Untreated | ENSG00000085662 | AKR1B1 | Linsitinib | 54.156 | 13.683 | 1.985 | 0.000 |
| Drug Treatment | Untreated | ENSG00000268621 | IGFL2-AS1 | Linsitinib | 0.358 | 0.095 | 1.916 | 0.000 |
| Drug Treatment | Untreated | ENSG00000108691 | CCL2 | Linsitinib | 0.791 | 0.210 | 1.914 | 0.000 |
| Drug Treatment | Untreated | ENSG00000109846 | CRYAB | Linsitinib | 0.847 | 0.295 | 1.520 | 0.000 |

FIG. 24B

SIMULTANEOUS SPATIO-TEMPORAL MEASUREMENT OF GENE EXPRESSION AND CELLULAR ACTIVITY

CROSS-REFERENCE TO RELATED APPLICATIONS

This application is a continuation of and claims priority to international Application No. PCT/US2021/033405, filed on May 20, 2021, which claims priority to U.S. Provisional Patent Application No. 63/029,121, filed May 22, 2020 and U.S. Provisional Patent Application No. 63/044,028, filed Jun. 25, 2020. The entire contents of the foregoing applications are incorporated herein by reference.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

Spatial gene expression technology generally allows for the capture of gene transcripts from frozen or fixed tissues while maintaining the spatial positioning of the gene transcripts within the tissues. However, the frozen and/or fixed nature of the sample limits concurrent experiments associated with the temporal aspect of gene expression, particularly in live cells and during conditions in which the sample is manipulated, for example, using pharmacological compositions. Further, spatial gene expression technology workflows generally are not amenable to the use of live tissues or cells; as such, the study or tracking of cellular activities is not available. Thus, there remains a need to develop novel devices and methods that address a situation in which spatial gene expression arrays can be used to detect gene expression and cellular activity concurrently in live or living tissues. Disclosed herein are systems and methods that utilize a perfusion chamber or a multi-well plate in conjunction with live tissue sections (e.g., generated through a vibratome) or cells (e.g., cultured directly on the substrate) that allow for the recording of cellular activity under standard conditions or in the presence of pharmacological manipulations.

SUMMARY

The present disclosure provides methods for tracking temporal information, e.g., by recording cellular activity and gene expression, in combination with spatial gene expression arrays for simultaneous spatio-temporal measurements. The present disclosure also provides devices, e.g., a perfusion chamber system or flowcell mounted to the spatial array, and a multi-well plate system, for such measurements. In some embodiments, provided herein are drug screening methods using the spatio-temporal measurements to generate a comprehensive multiomic understanding of drug's impact on tissue or cell culture.

In one aspect, provided herein is a method for identifying location and/or abundance of an analyte in a biological sample, the method comprising: (a) recording a cellular activity and/or an intracellular gene expression of a nucleic acid of the biological sample, and in some embodiments, the biological sample is located within a perfusion chamber in a plurality of perfusion chambers, and the perfusion chamber comprises a substrate; (b) contacting the biological sample with the substrate comprising a plurality of capture probes, and in some embodiments, a capture probe of the plurality of the capture probes comprises (i) a spatial barcode and (ii) a capture domain that binds specifically to a sequence present in the analyte; (c) extending the capture probe using the analyte that is specifically bound to the capture domain as a template, thereby generating an extended capture probe; (d) amplifying the extended capture probe to produce a plurality of extended capture probes; and (e) determining (i) all or a portion of the sequence of the spatial barcode, or a complement thereof, and (ii) all or a portion of the sequence of the analyte, or a complement thereof, and using the determined sequences of (i) and (ii) to identify the location and/or abundance of the analyte in the biological sample.

In some embodiments, provided herein is the method for identifying a location of an analyte in a biological sample, further comprising: mounting a gasket onto the substrate and mounting a cover onto the gasket to define a plurality of perfusion chambers. In some embodiments, the substrate comprises a plurality of substrate regions. In some embodiments, a substrate region of the plurality comprises the capture probe comprising (i) the spatial barcode and (ii) the capture domain that binds specifically to the sequence present in the analyte. In some embodiments, the gasket includes (i) a plurality of apertures corresponding to the plurality of substrate regions, respectively, (ii) a plurality of input channels being fluidly connected to the plurality of apertures, respectively, and (iii) a plurality of output channels being fluidly connected to the plurality of apertures, respectively. In some embodiments, the plurality of apertures of the gasket are aligned with the plurality of substrate regions of the substrate when the gasket is mounted onto the substrate. In some embodiments, the cover includes an inlet and an outlet, the inlet being fluidly connected to the plurality of input channels when the cover is mounted onto the gasket, the outlet being fluidly connected to the plurality of output channels when the cover is mounted onto the gasket. In some embodiments, the plurality of perfusion chambers are defined by (i) the plurality of substrate regions of the substrate, (ii) the plurality of apertures of the gasket that is mounted onto the substrate, and (iii) the cover that is mounted onto the gasket.

In some embodiments, the mounting a gasket onto the substrate and the mounting a cover onto the gasket to define a plurality of perfusion chambers occur prior to the recording the cellular activity or the recording the intracellular gene expression.

In some embodiments, the method further comprises perfusing a test compound through the perfusion chamber before the recording step. In some embodiments, the test compound is an agonist. In some embodiments, the test compound is an antagonist. In some embodiments, the test compound activates the cellular activity. In some embodiments, the test compound inhibits the cellular activity.

In one aspect, provided herein is a method for identifying location and/or abundance of an analyte in a biological sample, the method comprising: (a) recording a cellular activity and/or an intracellular gene expression of a nucleic acid of the biological sample, and in some embodiments, the biological sample is located within a well of a multi-well plate; (b) contacting the biological sample with a substrate comprising a plurality of capture probes, and in some embodiments, a capture probe of the plurality of the capture probes comprises (i) a spatial barcode and (ii) a capture domain that binds specifically to a sequence present in the analyte; (c) extending the capture probe using the analyte that is specifically bound to the capture domain as a template, thereby generating an extended capture probe; (d) amplifying the extended capture probe to produce a plurality of extended capture probes; and (e) determining (i) all or a portion of the sequence of the spatial barcode, or a complement thereof, and (ii) all or a portion of the sequence of the analyte, or a complement thereof, and using the determined sequences of (i) and (ii) to identify the location and/or abundance of the analyte in the biological sample.

In some embodiments, provided herein is the method for identifying a location of an analyte in a biological sample, further comprising treating the biological sample with one or more drugs.

In one aspect, provided herein is a method for determining the effect of one or more drugs applied on a cellular activity and/or an intracellular gene expression of a nucleic acid in a biological sample, the method comprising: (a) culturing the biological sample on a substrate, and in some embodiments, the substrate comprises a plurality of capture probes, and
in some embodiments, a capture probe of the plurality of the capture probes comprises (i) a spatial barcode and (ii) a capture domain that is capable to bind specifically to a an analyte associated with the cellular activity and/or the intracellular gene expression in the biological sample; (b) treating the biological sample with the one or more drugs; (c) recording the cellular activity and/or the intracellular gene expression of the nucleic acid of the biological sample; (d) capturing the analyte from the biological sample, and in some embodiments, the analyte is captured by the capture domain of the capture probe; and (e) determining the effect of the one or more drugs applied on the cellular activity and/or the intracellular gene expression in the biological sample, based on the level of the captured analyte.

In some embodiments, the multi-well plate is a 6-well plate, an 8-well plate, a 12-well plate, a 24-well plate, a 48-well plate, or a 96-well plate. In some embodiments, the multi-well plate is heat-resistant. In some embodiments, the multi-well plate is capable for automatic detecting of the cellular activity and/or the intracellular gene expression.

In some embodiments, the plurality of capture probes are directly attached to a surface of the well. In some embodiments, the plurality of capture probes are attached to the substrate. In some embodiments, the substrate is within the well. In some embodiments, the substrate is a coverslip. In some embodiments, the coverslip comprises plastic, metal, or glass. In some embodiments, the capture probe is attached to the substrate via a linkage group. In some embodiments, the linkage group is an amide group.

In some embodiments, the well or the substrate comprises a fiducial marker.

In some embodiments, the treating step occurs prior to the recording step. In some embodiments, the treating step and the recording step occur at substantially the same time.

In some embodiments, the biological sample is treated with the one or more drugs at substantially the same time. In some embodiments, the biological sample is treated with the one or more drugs at different times. In some embodiments, the biological sample is treated with one or more drugs about 6 hours, 12 hours, 18 hours, 24 hours, 30 hours, 36 hours, 42 hours, or 48 hours prior to fixing the biological sample.

In some embodiments, a drug of the one or more drugs is an agonist. In some embodiments, a drug of the one or more drugs is an antagonist.

In some embodiments, the biological sample is treated with a drug, and the drug is a small molecule.

In some embodiments, a drug of the one or more drugs activates the cellular activity and/or the intracellular gene expression. In some embodiments, a drug of the one or more drugs inhibits the cellular activity and/or the intracellular gene expression.

In some embodiments, a drug of the one or more drugs is conjugated with a fluorophore, and/or an oligonucleotide. In some embodiments, the oligonucleotide comprises a sequence that uniquely identifies the drug.

In some embodiments, provided herein, further comprising culturing the biological sample in the perfusion chamber or the well before the recording step.

In some embodiments, the biological sample is cultured in a culture medium to maintain its viability. In some embodiments, the culture medium is replaced at an appropriate interval manually or automatically.

In some embodiments, the biological sample is cultured statically.

In some embodiments, the biological sample is cultured in the perfusion chamber, and the method further comprising perfusing the culture medium within the perfusion chamber.

In some embodiments, the culture medium is supplemented with oxygen.

In some embodiments, the culture medium comprises a blocking reagent. In some embodiments, the biological sample is treated with the blocking reagent. In some embodiments, the blocking reagent is bovine serum albumin (BSA), serum, gelatin (e.g., fish gelatin), milk (e.g., non-fat dry milk), casein, polyethylene glycol (PEG), polyvinyl alcohol (PVA), or polyvinylpyrrolidone (PVP), biotin blocking reagent, a peroxidase blocking reagent, levamisole, Carnoy's solution, glycine, lysine, sodium borohydride, pontamine sky blue, Sudan Black, trypan blue, FITC blocking agent, and/or acetic acid.

In some embodiments, the cellular activity comprises protein activity, phosphorylation activity, G protein-coupled receptor related activity, ion channel activity, ligand-receptor binding activity, neural activity, protein synthesis, protein expression and localization, transient optical activity, cell-to-cell interactions, cellular morphology, or combinations thereof.

In some embodiments, the recording comprises optical recording. In some embodiments, the optical recording comprises contacting the biological sample with a chemical dye. In some embodiments, the chemical dye is a voltage-sensitive dye, a pH-sensitive dye, a temperature-sensitive dye, a light-sensitive dye, an oxygen-sensitive dye, or a metal sensitive dye. In some embodiments, the chemical dye is a metal-sensitive dye (e.g., a calcium-sensitive dye).

In some embodiments, the optical recording comprises labelling the biological sample with an indicator. In some embodiments, the indicator is a genetically-encoded indicator. In some embodiments, the genetically-encoded indicator is a genetically-encoded neural activity indicator, a genetically-encoded voltage indicator (GEVI) or a genetically-encoded calcium indicator (GECI, or GCaMP).

In some embodiments, the chemical dye or the indicator further comprises a fluorophore.

In some embodiments, the optical recording is achieved by in situ hybridization. In some embodiments, the optical recording is achieved by fluorescence resonance energy transfer (FRET).

In some embodiments, the optical recording comprises hybridization of a plurality of optically-labelled probes to (a) a protein, a lipid, a nucleic acid or a combination thereof associated with the cellular activity; or (b) the nucleic acid associated with the intracellular gene expression.

In some embodiments, an optically-labelled probe of the plurality is a peptide nucleic acid (PNA) probe labelled with a fluorophore.

In some embodiments, the PNA probe is at least 10 nucleic acid, at least 15 nucleic acids, at least 20 nucleic acids, at least 25 nucleic acids, at least 30 nucleic acids or more. In some embodiments, the nucleic acid hybridized to the PNA probe is DNA. In some embodiments, the nucleic acid hybridized to the PNA probe is RNA. In some embodiments, the RNA is mRNA.

In some embodiments, the optical recording is conducted using fluorescent time-lapse microscopy.

In some embodiments, the recording step occurs prior to the contacting step. In some embodiments, the contacting step occurs prior to the recording step. In some embodiments, the recording step and the contacting step occur at substantially the same time.

In some embodiments, the biological sample is a tissue sample. In some embodiments, the tissue sample is a live tissue section.

In some embodiments, the tissue sample is an organoid sample or a spheroid culture sample.

In some embodiments, the tissue sample is an organoid sample. In some embodiments, the organoid sample comprises normal organoids and/or cancer organoids. In some embodiments, the organoid sample comprises cancer organoids. In some embodiments, the organoid sample comprises intestinal organoids, liver organoids, pulmonary organoids, and/or neural organoids. In some embodiments, the organoid sample is originated from disease-affected tissues (e.g., cancer tissues), normal tissue, disease-affected cells (e.g., cancer cells), normal cells, differentiated cells (e.g., somatic cells), and/or stem cells. In some embodiments, the organoid sample is originated from stem cells. In some embodiments, the stem cells are embryonic stem cells, induced pluripotent stem cells, and/or somatic stem cells.

In some embodiments, the tissue sample is embedded in hydrogels.

In some embodiments, the biological sample is a cell culture sample. In some embodiments, the cell sample is a primary cell culture sample. In some embodiments, the primary cell culture sample comprises individual cells that are isolated from a fresh tissue. In some embodiments, the cell sample comprises a plurality of adherent cells. In some embodiments, the cell sample comprises a plurality of suspension cells. In some embodiments, the cell sample is transferred to the well from a separate cell culture. In some embodiments, the cell sample comprises a plurality of disease-affected cells. In some embodiments, one or more cells of the cell sample are transfected or infected. In some embodiments, the biological sample is from a human patient or a model animal (e.g., a mouse).

In some embodiments, the analyte comprises a mutation. In some embodiments, the analyte comprises a single nucleotide polymorphism (SNP). In some embodiments, the analyte comprises a trinucleotide repeat. In some embodiments, the analyte is associated with a disease or condition.

In some embodiments, the analyte is a DNA molecule. In some embodiments, the analyte is a complementary DNA (cDNA). In some embodiments, the analyte is an RNA molecule. In some embodiments, the RNA molecule is an mRNA molecule.

In some embodiments, the capture domain of the capture probe is blocked prior to the contacting step. In some embodiments, the capture domain is blocked by a blocking probe.

In some embodiments, the biological sample comprises a plurality of live cells, and the live cells are stained by immunofluorescence before the recording step. In some embodiments, the one or more live cells are treated with protease K and/or trypsin.

In some embodiments, the biological sample is stained using a detectable label. In some embodiments, the detectable label is Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS). In some embodiments, the detectable label is H&E.

In some embodiments, the biological sample is imaged. In some embodiments, the biological samples is imaged using brightfield imaging.

In some embodiments, the biological sample is permeabilized after the recording step with a permeabilization agent selected from an organic solvent, a cross-linking agent, a detergent, and an enzyme, or a combination thereof.

In some embodiments, the biological sample is fixed after contacting the biological sample with the substrate, or culturing the biological sample on the substrate. In some embodiments, the biological sample is fixed with ethanol, methanol, acetone, formaldehyde (e.g., 2% formaldehyde), paraformaldehyde-Triton, glutaraldehyde, or combinations thereof.

In some embodiments, the capture probe further comprises a functional sequence. In some embodiments, the functional sequence is a primer sequence or a complement thereof. In some embodiments, the capture probe further comprises a unique molecular sequence or a complement thereof. In some embodiments, the capture probe further comprises an additional primer binding sequence or a complement thereof. In some embodiments, the capture domain comprises a sequence that is substantially complementary to the sequence of the analyte. In some embodiments, the capture domain comprises a sequence that is partially complementary to the sequence of the analyte. In some embodiments, the capture domain comprises an oligo d(T) sequence.

In some embodiments, in the extending step, the capture probe is extended at the 3' end. In some embodiments, the extending step utilizes a reverse transcriptase. In some embodiments, the extending step utilizes fluorescently labeled nucleotides.

In some embodiments, the biological sample is removed after the amplifying step. In some embodiments, the biological sample is enzymatically removed after the amplifying step.

In some embodiments, the amplifying step comprises amplifying (i) all or part of sequence of the analyte bound to the capture domain, or a complement thereof, and (ii) all or a part of the sequence of the spatial barcode, or a complement thereof.

In some embodiments, the amplifying step comprises rolling circle amplification.

In some embodiments, the amplifying step utilizes a DNA polymerase, a plurality of primers, and a plurality of nucleotides.

In some embodiments, the amplifying is not isothermal. In some embodiments, the amplifying is isothermal.

In some embodiments, the produced nucleic acid is released from the extended capture probe.

In some embodiments, the determining step comprises sequencing. In some embodiments, the determining step comprises sequencing (i) all or a portion of the sequence of the spatial barcode or the complement thereof, and (ii) all or a portion of the sequence of the analyte. In some embodiments, the sequencing is high throughput sequencing. In some embodiments, the sequencing step comprises in situ sequencing, Sanger sequencing methods, next-generation sequencing methods, and nanopore sequencing.

In some embodiments, the sequencing comprises ligating an adapter to the nucleic acid.

In one aspect, provided herein is a method for determining location and/or abundance of an analyte in a live tissue or cell sample, the method comprising:
- (a) providing a plurality of perfusion chambers, wherein a perfusion chamber of the plurality of perfusion chambers comprises a substrate, a gasket mounted onto the substrate, and a cover mounted onto the gasket, wherein the live tissue or cell sample is located within the perfusion chamber of the plurality of perfusion chambers, wherein
  - (1) the substrate comprises a plurality of substrate regions, wherein a substrate region of the plurality comprises a plurality of capture probes, wherein a capture probe of the plurality of capture probes comprises (i) a spatial barcode and (ii) a capture domain that binds specifically to a sequence present in the analyte;
  - (2) the gasket comprises (i) a plurality of apertures corresponding to the plurality of substrate regions, respectively, (ii) a plurality of input channels being fluidly connected to the plurality of apertures, respectively, and (iii) a plurality of output channels being fluidly connected to the plurality of apertures, respectively, and wherein the plurality of apertures of the gasket are aligned with the plurality of substrate regions of the substrate when the gasket is mounted onto the substrate;
  - (3) the cover comprises an inlet and an outlet, the inlet being fluidly connected to the plurality of input channels when the cover is mounted onto the gasket, the outlet being fluidly connected to the plurality of output channels when the cover is mounted onto the gasket; and
  - (4) the plurality of perfusion chambers are defined by (i) the plurality of substrate regions of the substrate, (ii) the plurality of apertures of the gasket that is mounted onto the substrate, and (iii) the cover that is mounted onto the gasket;
- (b) perfusing one or more test compounds through the perfusion chamber;
- (c) recording a cellular activity and/or an intracellular gene expression of a nucleic acid of the live tissue or cell sample,
- (d) permeabilizing the live tissue or cell sample such that the analyte is specifically bound to the capture domain of the capture probe of the plurality of capture probes;
- (e) disassembling the gasket and the cover from the substrate;
- (f) extending the capture probe at the 3' end using the analyte that is specifically bound to the capture domain as a template, thereby generating an extended capture probe;
- (g) amplifying the extended capture probe to produce a plurality of extended capture probes; and
- (h) sequencing (i) all or a portion of the sequence of the spatial barcode, or a complement thereof, and (ii) all or a portion of the sequence of the analyte, or a complement thereof, and using the determined sequences of (i) and (ii) to determine the location and the location and/or abundance of the analyte in the live tissue or cell sample.

In one aspect, provided herein is a method for identifying location and/or abundance of an analyte in a live tissue or cell sample, the method comprising:
- (a) providing a multi-well plate comprising a substrate and a gasket mounted onto the substrate, wherein the substrate comprises a plurality of substrate regions, wherein a substrate region of the plurality of substrate regions comprises capture probes, wherein a capture probe of the plurality of capture probes comprises (i) a spatial barcode and (ii) a capture domain that binds specifically to a sequence present in the analyte; wherein the gasket comprises a plurality of apertures, wherein the gasket is configured to be mounted onto the substrate such that the plurality of apertures are aligned with the plurality of substrate regions, respectively; wherein a well of the multi-well plate is defined by a substrate region of the substrate and an aperture of the gasket; wherein the live tissue or cell sample is located within the well of the multi-well plate;
- (b) treating the live tissue or cell sample with one or more test compounds;
- (c) recording a cellular activity and/or an intracellular gene expression of a nucleic acid of the live tissue or cell sample;
- (d) permeabilizing the live tissue or cell sample such that the analyte is specifically bound to the capture domain of the capture probe of the plurality of capture probes;
- (e) disassembling the gasket from the substrate; extending the capture probe at the 3' end using the analyte that is specifically bound to the capture domain as a template, thereby generating an extended capture probe;
- (g) amplifying the extended capture probe to produce a plurality of extended capture probes; and
- (h) sequencing (i) all or a portion of the sequence of the spatial barcode, or a complement thereof, and (ii) all or a portion of the sequence of the analyte, or a complement thereof, and using the determined sequences of (i) and (ii) to identify the location and/or abundance of the analyte in the live tissue or cell sample.

In one aspect, provided herein is a method for identifying location and/or abundance of an analyte in a live tissue or cell sample, the method comprising:
- (a) providing a multi-well plate, wherein a well of the multi-well plate comprises a substrate, wherein the substrate comprises a plurality of capture probes, wherein a capture probe of the plurality of capture probes comprises (i) a spatial barcode and (ii) a capture domain that binds specifically to a sequence present in the analyte; wherein the live tissue or cell sample is located within the well of the multi-well plate;
- (b) treating the live tissue or cell sample with one or more test compounds;

(c) recording a cellular activity and/or an intracellular gene expression of a nucleic acid of the live tissue or cell sample;

(d) permeabilizing the live tissue or cell sample such that the analyte is specifically bound to the capture domain of the capture probe of the plurality of capture probes;

(e) extending the capture probe at the 3' end using the analyte that is specifically bound to the capture domain as a template, thereby generating an extended capture probe; amplifying the extended capture probe to produce a plurality of extended capture probes; and (g) sequencing (i) all or a portion of the sequence of the spatial barcode, or a complement thereof, and (ii) all or a portion of the sequence of the analyte, or a complement thereof, and using the determined sequences of (i) and (ii) to identify the location and/or abundance of the analyte in the live tissue or cell sample.

In one aspect, provided herein is a kit comprising a) an array comprising a plurality of capture probes; b) a perfusion chamber defined by mounting a gasket on the array, and a cover mounted on the gasket, wherein the cover includes: (i) an inlet being fluidly connected to a plurality of input channels, and (ii) an outlet being fluidly connected to a plurality of output channels; and c) an instruction for using the kit.

In one aspect, provided herein is a kit comprising a) a multi-well plate comprising a plurality of capture probes, wherein the plurality of capture probes are directly attached (e.g., printed) to a surface of a well of the multi-well plate; and b) an instruction for using the kit.

In one aspect, provided herein is a kit comprising a) a coverslip comprising a plurality of capture probes; b) a multi-well plate, wherein the coverslip is attached to a surface of a well of the multi-well plate; and c) an instruction for using the kit. In some embodiments, the multi-well plate is a 6-well plate, an 8-well plate, a 12-well plate, a 24-well plate, a 48-well plate, or a 96-well plate.

In one aspect, provided herein is a kit comprising a) a slide comprising a plurality of arrays, wherein an array of the plurality of arrays comprises capture probes; b) a gasket comprising a plurality of apertures, wherein the gasket is configured to be mounted onto the slide such that the plurality of apertures are aligned with the plurality of arrays; and c) an instruction for using the kit.

In one aspect, provided herein is an apparatus for measuring cellular activity and/or gene expression, comprising: a gasket including a plurality of apertures, a plurality of input channels being fluidly connected to the plurality of apertures, respectively, and a plurality of output channels being fluidly connected to the plurality of apertures, respectively; and a cover configured to be mounted onto the gasket, the cover comprising: an inlet configured to be fluidly connected to the plurality of input channels of the gasket when the cover is mounted onto the gasket, and an outlet configured to be fluidly connected to the plurality of output channels of the gasket when the cover is mounted onto the gasket.

In some embodiments, the plurality of apertures includes: inlet ports that fluidly connect to the plurality of input channels, respectively; and outlet ports that fluidly connect to the plurality of output channels, respectively.

In some embodiments, the apparatus described herein further comprises a substrate having a plurality of substrate regions. In some embodiments, the gasket is configured to be mounted onto the substrate such that the plurality of apertures are aligned with the plurality of substrate regions, respectively. In some embodiments, the cover is configured to be mounted onto the gasket opposite to the substrate. In some embodiments, a plurality of perfusion chambers are defined by (i) the plurality of substrate regions of the substrate, (ii) the plurality of apertures of the gasket that is mounted onto the substrate, and (iii) the cover that is mounted onto the gasket In some embodiments, the gasket is made of silicone.

In some embodiments, each of the substrate regions is configured to attach a capture probe that includes (i) a spatial barcode and (ii) a capture domain that binds to a sequence present in an analyte.

In some embodiments, the gasket has a thickness that ranges between 0.6 mm and 1.0 mm.

In some embodiments, the gasket includes an upstream bore and a downstream bore. In some embodiments, the plurality of input channels extend between the upstream bore and the inlet ports of the plurality of apertures, respectively. In some embodiments, the plurality of output channel extend between the downstream bore and the outlet ports of the plurality of apertures, respectively.

In some embodiments, the plurality of input channels have different lengths between the upstream bore and the inlet ports of the plurality of apertures, respectively.

In some embodiments, the plurality of output channels have different lengths between the downstream bore and the outlet ports of the plurality of apertures, respectively.

In some embodiments, the upstream bore is positioned to be opposite to the downstream bore with respect to a center of the gasket. In some embodiments, the upstream bore is configured to be aligned with the inlet of the cover. In some embodiments, the downstream bore is configured to be aligned with the outlet of the cover.

In some embodiments, each of the plurality of apertures includes at least a portion having a width that varies between the inlet port and the outlet port.

In some embodiments, each of the plurality of apertures includes: a first portion including the inlet port and having a first width; and a second portion including the outlet port and having a second width.

In some embodiments, the first width of the first portion varies between the inlet port and the second portion. In some embodiments, the first width of the first portion gradually increases from the inlet port to an interface between the first portion and the second portion. In some embodiments, the second width of the second portion is consistent. In some embodiments, the first width of the first portion is identical to the second width of the second portion at the interface between the first portion and the second portion.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIGS. 8A and 8B are schematics illustrating expanded FIG. 8A and side views FIG. 8B of an electrophoretic transfer system configured to direct transcript analytes toward a spatially-barcoded capture probe array.

FIG. 13A shows spectral overlap during FRET excitation. FIG. 13B demonstrates that FRET excitation occurs at distances between the emission donor and excitation acceptor of less than 10 nm. FIG. 13C shows orientation of the emission donor and excitation acceptor molecules.

FIG. 24B shows the top differentially expressed genes between different treatment cultures.

DETAILED DESCRIPTION

I. Introduction

Figure 1:
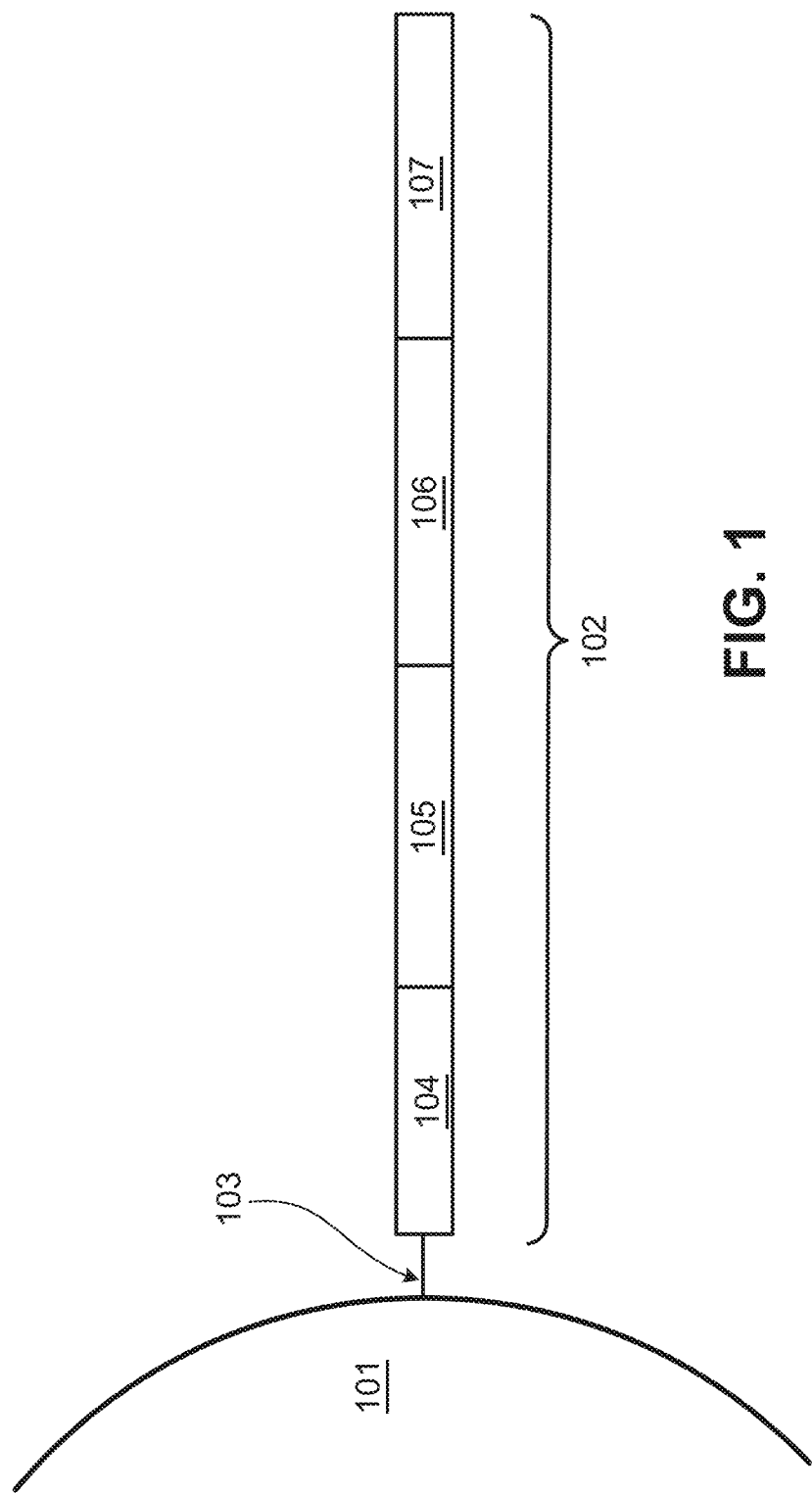
FIG. 1 is a schematic diagram showing an example of a barcoded capture probe, as described herein.

Disclosed herein are methods and apparatus for measuring cellular activity and/or gene expression (e.g., by optical recordings) to track temporal information as well as identifying a location of a target analyte (e.g., using capture probes attached to a surface (e.g., a substrate) within a perfusion chamber, or a well of a multi-well plate) to track spatial information in a biological sample (e.g., a cell culture or live tissue sections). Here, the perfusion chamber and the multi-well plate are two exemplary types of culturing systems that allow live tissue/cell samples to be recorded in situ, and culture medium can be perfused or replaced to maintain tissue/cell viability. One direct application of the methods described herein is to determine the effect of drugs to the cellular activity and/or gene expression, and correlate the determined effect with the spatial information as obtained using capture probes, thereby providing an in-depth understanding of the drug's effect to the biological sample.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLOS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev D, dated October 2020), and/or the Visium Spatial Tissue Optimization Reagent Kits User Guide (e.g., Rev D, dated October 2020), both of which are available at the 10x Genomics Support Documentation website, and can be used herein in any combination. Further non-limiting aspects of spatial analysis methodologies and compositions are described herein.

Some general terminologies that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a connected probe (e.g., a ligation product) or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)).

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that is useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, a sequence complementary to a portion of a connected probe described herein, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 are common to all of the probes attached to a given feature. In some embodiments, the UMI sequence 106 of a capture probe attached to a given feature is different from the UMI sequence of a different capture probe attached to the given feature.

Figure 2:
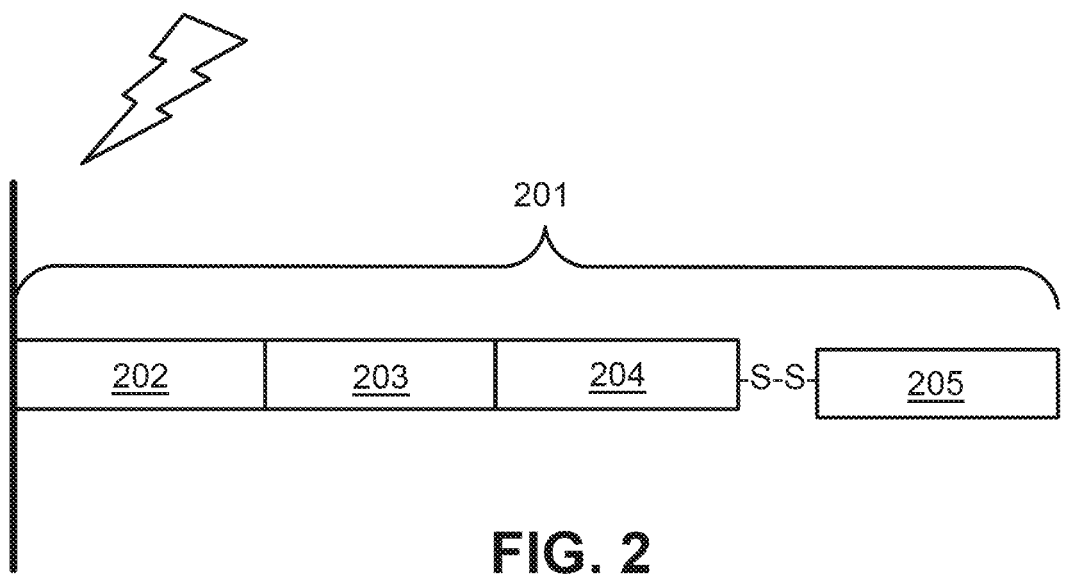
FIG. 2 is a schematic illustrating a cleavable capture probe, wherein the cleaved capture probe can enter into a non-permeabilized cell and bind to target analytes within the sample.

FIG. 2 is a schematic illustrating a cleavable capture probe, wherein the cleaved capture probe can enter into a non-permeabilized cell and bind to analytes within the sample. The capture probe 201 contains a cleavage domain 202, a cell penetrating peptide 203, a reporter molecule 204, and a disulfide bond (—S—S—). 205 represents all other parts of a capture probe, for example a spatial barcode and a capture domain.

Figure 3:
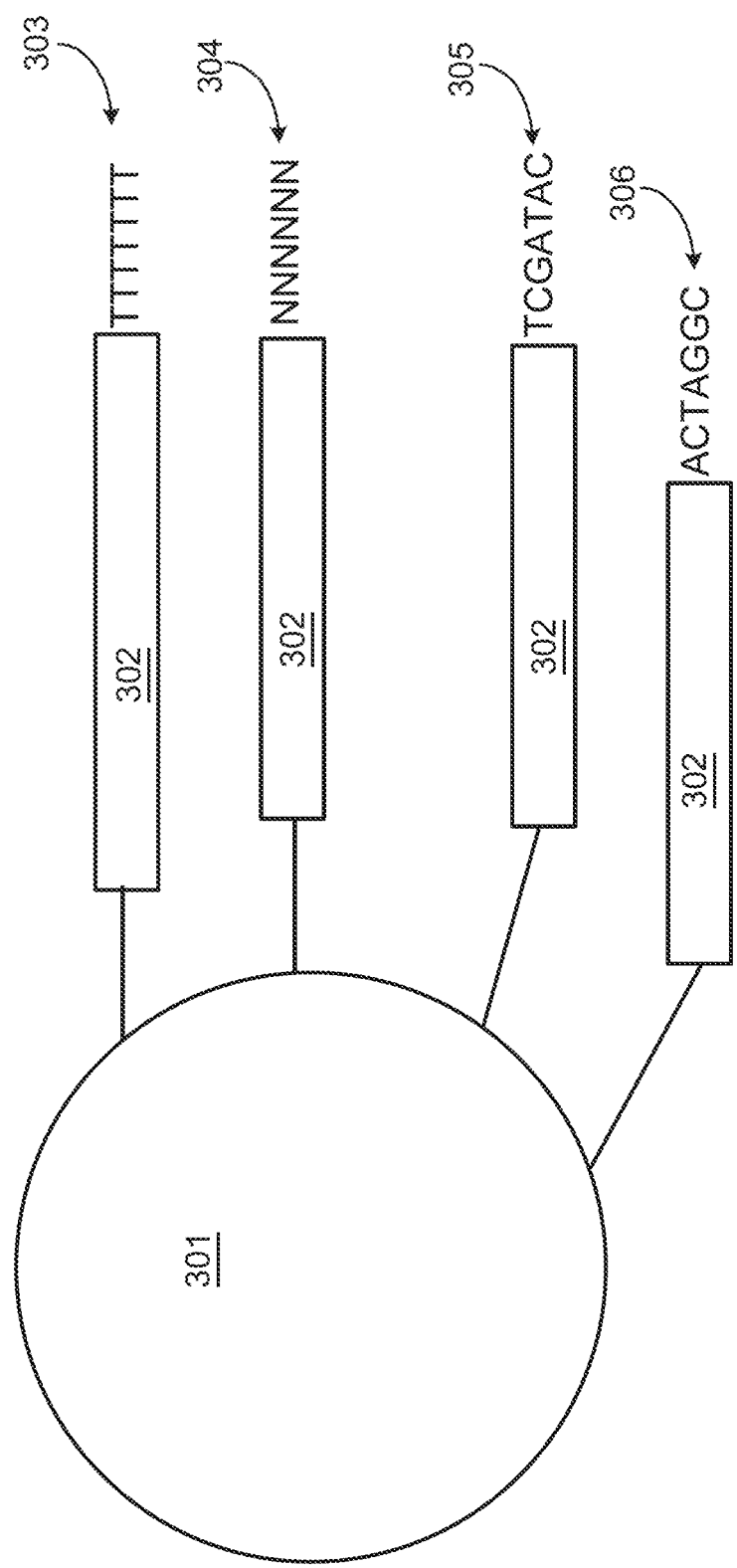
FIG. 3 is a schematic diagram of an exemplary multiplexed spatially-barcoded feature.

FIG. 3 is a schematic diagram of an exemplary multiplexed spatially-barcoded feature. In FIG. 3, the feature 301 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 302. One type of capture probe associated with the feature includes the spatial barcode 302 in combination with a poly(T) capture domain 303, designed to capture mRNA target analytes. A second type of capture probe associated with the feature includes the spatial barcode 302 in combination with a random N-mer capture domain 304 for gDNA analysis. A third type of capture probe associated with the feature includes the spatial barcode 302 in combination with a capture domain complementary to a capture handle sequence of an analyte capture agent of interest 305. A fourth type of capture probe associated with the feature includes the spatial barcode 302 in combination with a capture domain that can specifically bind a nucleic acid molecule 306 that can function in a CRISPR assay (e.g., CRISPR/Cas9). While only four different capture probe-barcoded constructs are shown in FIG. 3, capture-probe barcoded constructs can be tailored for analyses of any given analyte associated with a nucleic acid and capable of binding with such a construct. For example, the schemes shown in FIG. 3 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MHC multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents. See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) a capture handle sequence. As used herein, the term "analyte binding moiety barcode" refers to a barcode that is associated with or otherwise identifies the analyte binding moiety. As used herein, the term "analyte capture sequence" or "capture handle sequence" refers to a region or moiety configured to hybridize to, bind to, couple to, or otherwise interact with a capture domain of a capture probe. In some embodiments, a capture handle sequence is complementary to a capture domain of a capture probe. In some cases, an analyte binding moiety barcode (or portion thereof) may be able to be removed (e.g., cleaved) from the analyte capture agent.

Figure 4:
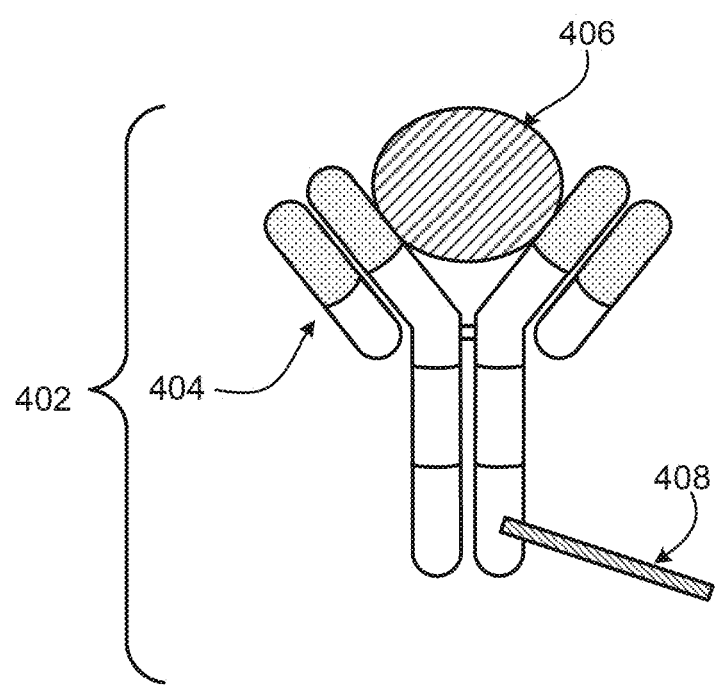
FIG. 4 is a schematic diagram of an exemplary analyte capture agent.

FIG. 4 is a schematic diagram of an exemplary analyte capture agent 402 comprised of an analyte-binding moiety 404 and an analyte-binding moiety barcode domain 408. The exemplary analyte-binding moiety 404 is a molecule capable of binding to an analyte 406 and the analyte capture agent is capable of interacting with a spatially-barcoded capture probe. The analyte-binding moiety can bind to the analyte 406 with high affinity and/or with high specificity. The analyte capture agent can include an analyte-binding moiety barcode domain 408, a nucleotide sequence (e.g., an oligonucleotide), which can hybridize to at least a portion or an entirety of a capture domain of a capture probe. The analyte-binding moiety barcode domain 408 can comprise an analyte binding moiety barcode and a capture handle sequence described herein. The analyte-binding moiety 404 can include a polypeptide and/or an aptamer. The analyte-binding moiety 404 can include an antibody or antibody fragment (e.g., an antigen-binding fragment).

Figure 5:
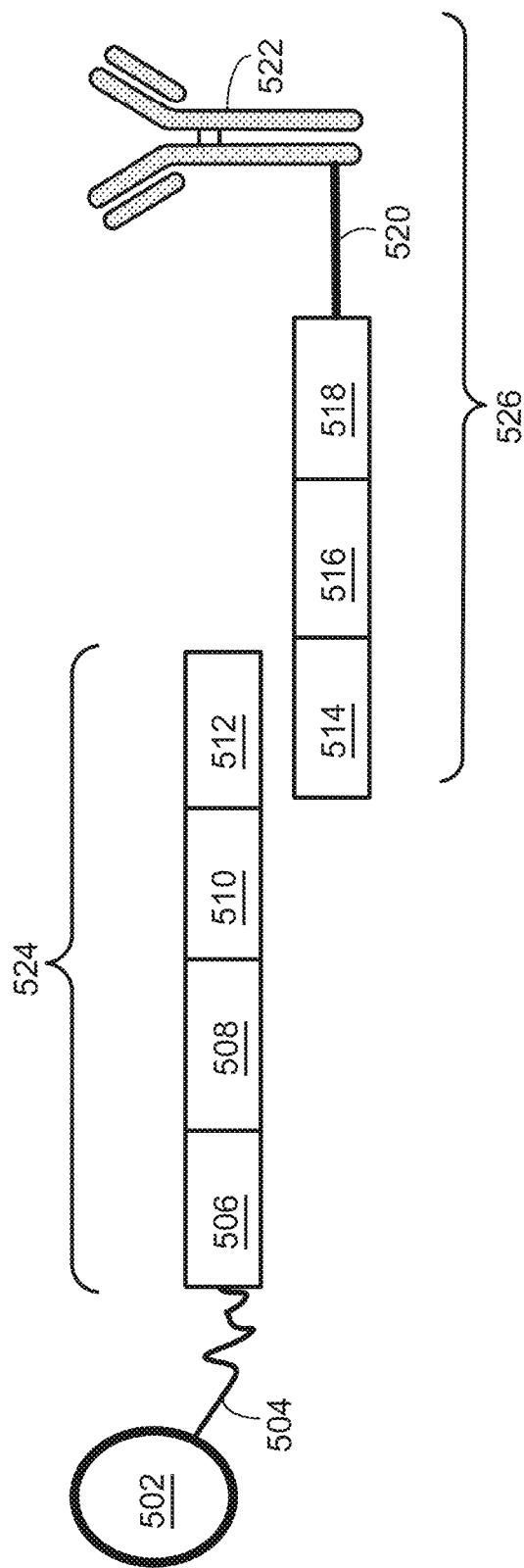
FIG. 5 is a schematic diagram depicting an exemplary interaction between a feature-immobilized capture probe 524 and an analyte capture agent 526.

FIG. 5 is a schematic diagram depicting an exemplary interaction between a feature-immobilized capture probe 524 and an analyte capture agent 526. The feature-immobilized capture probe 524 can include a spatial barcode 508 as well as functional sequences 506 and UMI 510, as described elsewhere herein. The capture probe can also include a capture domain 512 that is capable of binding to an analyte capture agent 526. The analyte capture agent 526 can include a functional sequence 518, analyte binding moiety barcode 516, and a capture handle sequence 514 that is capable of binding to the capture domain 512 of the capture probe 524. The analyte capture agent can also include a linker 520 that allows the capture agent barcode domain 516 to couple to the analyte binding moiety 522.

Figure 6A:
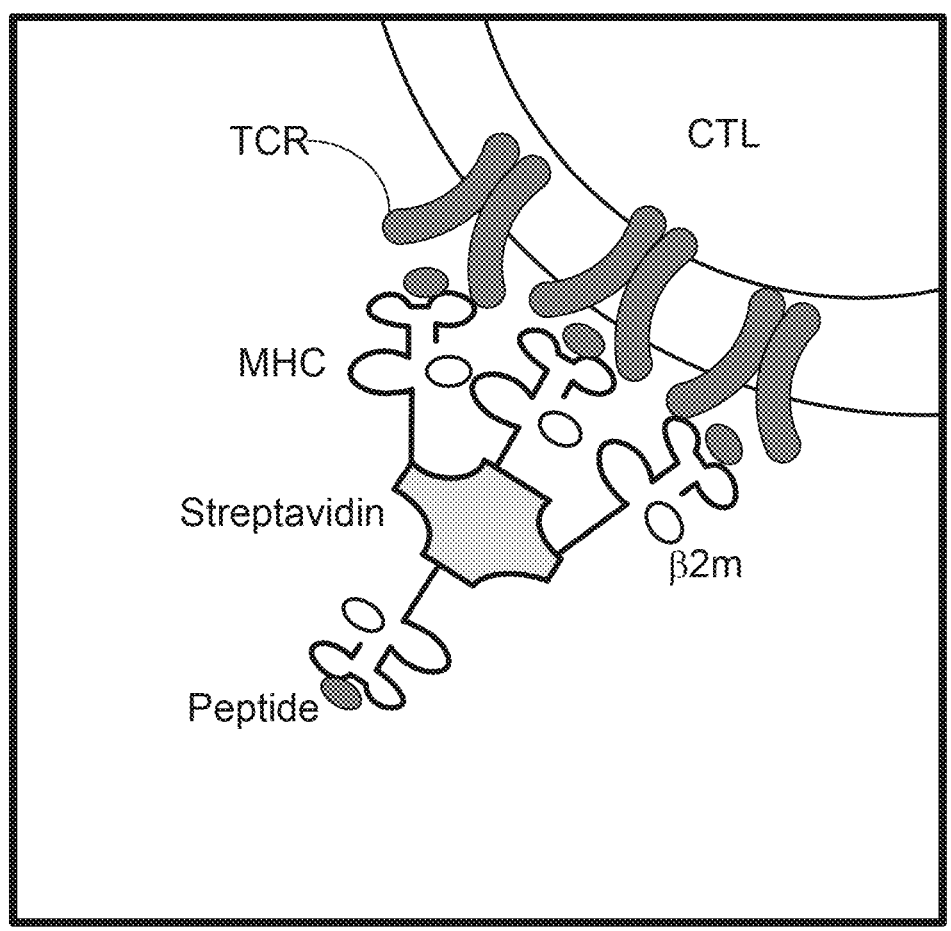
FIGS. 6A, 6B, and 6C are schematics illustrating how streptavidin cell tags can be utilized in an array-based system to produce spatially-barcoded cells or cellular contents.
Figure 6B:
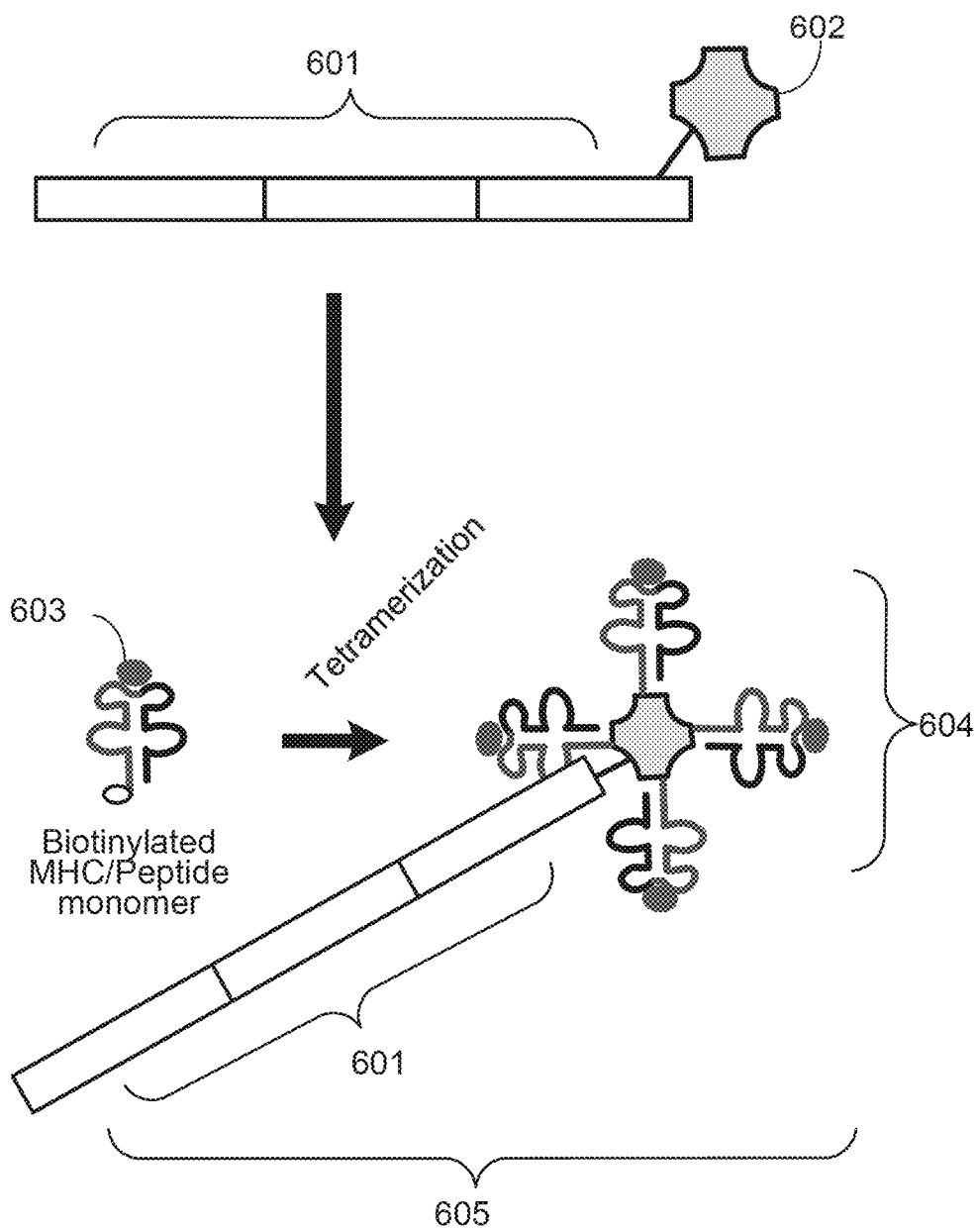
Figure 6C:
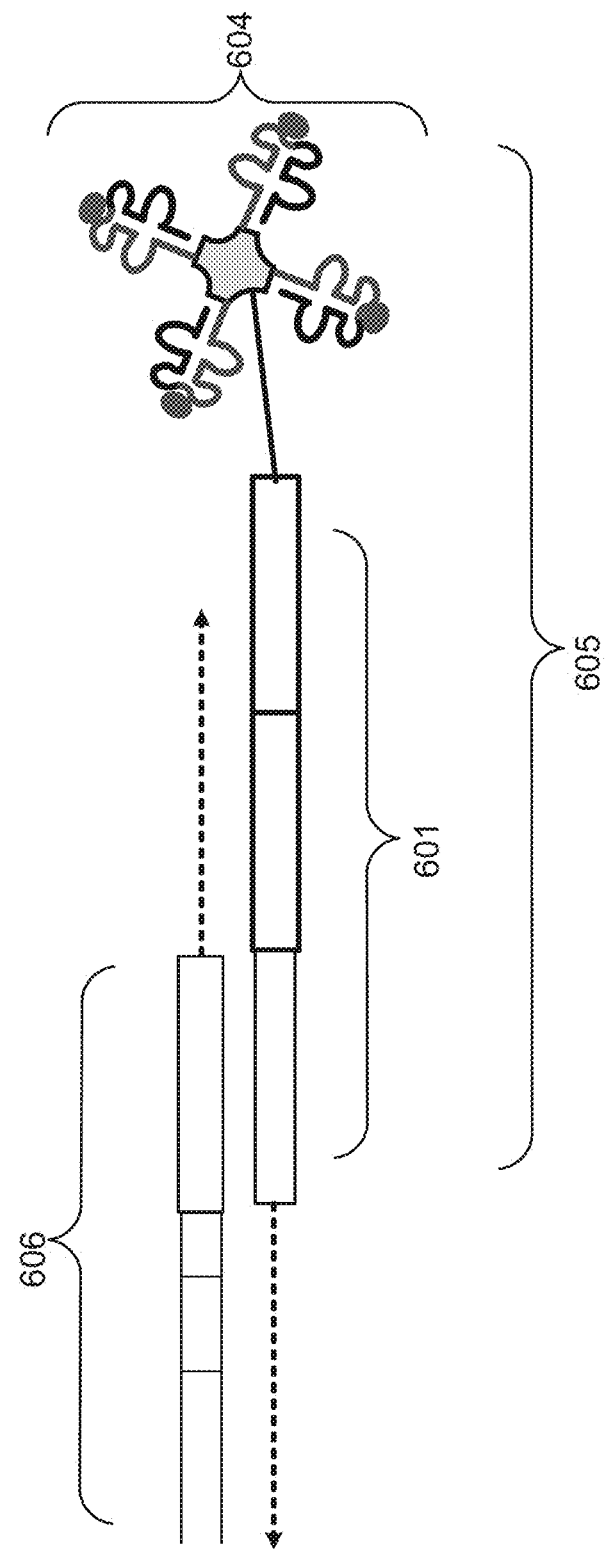

FIGS. 6A, 6B, and 6C are schematics illustrating how streptavidin cell tags can be utilized in an array-based system to produce a spatially-barcoded cell or cellular contents. For example, as shown in FIG. 6A, peptide-bound major histocompatibility complex (MHC) can be individually associated with biotin ($\beta$2m) and bound to a streptavidin moiety such that the streptavidin moiety comprises multiple pMHC moieties. Each of these moieties can bind to a TCR such that the streptavidin binds to a target T-cell via multiple MHC/TCR binding interactions. Multiple interactions synergize and can substantially improve binding affinity. Such improved affinity can improve labelling of T-cells and also reduce the likelihood that labels will dissociate from T-cell surfaces. As shown in FIG. 6B, a capture agent barcode domain 601 can be modified with streptavidin 602 and contacted with multiple molecules of biotinylated MHC 603 such that the biotinylated MHC 603 molecules are coupled with the streptavidin conjugated capture agent barcode domain 601. The result is a barcoded MHC multimer complex 605. As shown in FIG. 6B, the capture agent barcode domain sequence 601 can identify the MHC as its associated label and also includes optional functional sequences such as sequences for hybridization with other oligonucleotides. As shown in FIG. 6C, one example oligonucleotide is capture probe 606 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1"), R2), a flow cell attachment sequence (e.g., P5 or P7 or partial sequences thereof)), etc. In some cases, capture probe 606 may at first be associated with a feature (e.g., a gel bead) and released from the feature. In other embodiments, capture probe 606 can hybridize with a capture agent barcode domain 601 of the MHC-oligonucleotide complex 605. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of the corresponding sequences may be a complement of the original sequence in capture probe 606 or capture agent barcode domain 601. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 606 spatial barcode sequence may be used to identify a feature and the sequence derived from spatial barcode sequence on the capture agent barcode domain 601 may be used to identify the particular peptide MHC complex 604 bound on the surface of the cell (e.g., when using MHC-peptide libraries for screening immune cells or immune cell populations).

Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/ or into or onto the biological sample.

In some cases, capture probes may be configured to prime, replicate, and consequently yield optionally barcoded extension products from a template (e.g., a DNA or RNA template, such as an analyte or an intermediate agent (e.g., a connected probe (e.g., a ligation product) or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form a connected probe (e.g., a ligation product) with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction). Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., Nucleic Acids Res. 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a connected probe (e.g., a ligation product). In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the connected probe (e.g., a ligation product) is released from the analyte. In some instances, the connected probe (e.g., a ligation product) is released using an endonuclease (e.g., RNAse H). The released connected probe (e.g., a ligation product) can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev D, dated October 2020), and/or the Visium Spatial Tissue Optimization Reagent Kits User Guide (e.g., Rev D, dated October 2020). In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array.

Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

II. Simultaneous Spatio-Temporal Measurement of Gene Expression and Cellular Activity Spatial transcriptomics is performed on biological samples, for example tissue sections that are in some manner processed prior to assaying. Spatial workflows allow for the detection of, for example, gene expression from frozen or fixed tissues while maintaining the spatial position of the gene expression within the tissue. The disclosed methods and systems allow for the utilization of a spatial assay platform in conjunction with live tissue sections or cells for the study of, for example, pharmacological drug discovery, protein interactions, or other cellular activities that are best studied using live tissues or cells as a starting material.

(a) Biological sample

In some embodiments, disclosed herein are methods of detecting cellular activity and/or gene expression in a biological sample. In some instances, the biological sample is a tissue sample. In some embodiments, the tissue sample is a live tissue section. In some embodiments, the live tissue sample is sectioned (e.g., using a vibratome or any slicing instruments known in the art) from a fresh tissue. In some embodiments, the live tissue section can be treated (e.g., an enzymatic dissociation) to release individual cells, such that the isolated individual cells can be analyzed using the methods described herein. In some embodiments, the tissue sample is an intact tissue. In some embodiments, the tissue sample is a semi-intact tissue.

In some embodiments, the live tissue sample is cultured (e.g., in a tissue culture medium) in the perfusion chamber or the multi-well plate described herein before a recording step. Recording as used herein includes but is not limited to determining or measuring the abundance of an analyte or biological activity in a sample. In some instances, recording includes imaging the sample using any of the method steps disclosed herein. In some instances, the recording includes determining the abundance of an analyte (e.g., protein, RNA, DNA) or biological activity in a sample. In some instances, recording (e.g., determining) is performed using qualitative techniques. In some instances, recording (e.g., determining) is performed using quantitative techniques. In some instances, recording includes detecting the presence of and/or abundance of a reporter or detectable marker (e.g., fluorescent protein detection). Recording a cellular or biological activity includes measuring the presence or abundance of an activity in a cell. Activities include but are not limited to protein activity (e.g., kinase activity), phosphorylation activity, G protein-coupled receptor related activity, ion channel activity (e.g., switch between open and closed conformation), ligand-receptor binding activity, neural activity (e.g., neuronal action potentials), protein synthesis (e.g., transcription or translation) activity, protein expression and localization (e.g., sub-cellular organelle protein expression and trafficking), transient optical activity (e.g., optical reporter gene expression), cell-to-cell interaction, cellular morphology, vesicular trafficking (e.g., exocytosis or endocytosis), protein translocation and/or protein post-translational modifications (e.g., ubiquitination or glycosylation). In some embodiments, the cellular activity includes processes in cell signaling pathways or cascades. In some embodiments, the cellular activity includes conformational changes of biomolecules (e.g., proteins or nucleic acids).

In some embodiments, the live tissue sample is cultured in a separate tissue culture or a substrate (e.g., a coverslip, sponge gels, etc.), then transferred to the perfusion chamber or the multi-well plate described herein. In some embodiments, additional compounds (e.g., artificial cerebrospinal fluid) are supplemented to the tissue culture medium to maintain cell viability of the live tissue sample (e.g., a neuronal tissue). In some embodiments, the live tissue sample is directly placed in the perfusion chamber or the multi-well plate, without culturing before the recording step. For example, the live tissue sample can be sectioned from a fresh tissue and directly placed in the perfusion chamber or the multi-well plate before the recording step. In some embodiments, the sectioned live tissue sample is placed in a suspension oxygenated medium to maintain tissue viability.

In some embodiments, the tissue sample is an organoid sample. An organoid is a miniaturized and simplified version of an organ produced in vitro in three dimensions that shows realistic micro-anatomy. For example, some organoids are derived from one or a few cells from a tissue, embryonic stem cells or induced pluripotent stem cells, which can self-organize in three-dimensional culture owing to their self-renewal and differentiation capacities. In some embodiments, the organoid sample is a cerebral organoid, gut organoid, intestinal organoid (e.g., small intestinal organoid), stomach (or gastric) organoid, lingual organoid, thyroid organoid, thymic organoid, testicular organoid, hepatic organoid, pancreatic organoid, epithelial organoid, liver organoid, pulmonary organoid, neural organoid, brain organoid, lung organoid, kidney organoid, embryonic organoid, blastocyst-like organoid, cardiac organoid, retinal organoid, or any combinations thereof. In some embodiments, the organoid sample is originated from disease-affected tissues (e.g., cancer tissues) or normal tissues. In some embodiments, the organoid sample is originated from disease-affected cells (e.g., cancer cells) or normal cells. In some embodiments, the organoid is originated from stem cells (e.g., embryonic stem cells, induced pluripotent stem cells, and/or somatic stem cells), or differentiated cells (e.g., somatic cells). Details can be found, e.g., in Xu, et al., *Journal of Hematology & Oncology* 11.1 (2018): 116; and Clevers, Hans, Cell 165.7 (2016): 1586-1597; each of which is incorporated herein by reference by its entirety.

In some embodiments, overall tissue viability of cells in the tissue sample is at least or about 60%, at least or about 65%, at least or about 70%, at least or about 75%, at least or about 80%, at least or about 85%, at least or about 90%, at least or about 95%, at least or about 96%, at least or about 97%, at least or about 98%, at least or about 99%, or 100%.

In some embodiments, the biological sample is a cell sample (e.g., cells present in a cell culture). In some embodiments, the cell sample is cultured in the perfusion chamber or the multi-well plate before the recording step, e.g., for at least 1 hour, at least 2 hours, at least 3 hours, at least 4 hours, at least 6 hours, at least 12 hours, at least 1 day, at least 2 days, at least 3 days, at least 4 days, at least 5 days, at least a week, at least 2 weeks, at least 3 weeks, or longer. In some embodiments, the cells of the cell sample are directly cultured in the perfusion chamber or the multi-well plate, e.g., by seeding the cells at an appropriate density known in the art. The perfusion chamber or the multi-well plate can serve as a cell culture container and a culture medium can be perfused (or added) within the perfusion chamber or the multi-well plate to maintain viability of the cells. In some embodiments, the cell sample is transferred to the perfusion chamber or the multi-well plate from a separate cell culture. In some embodiments, the cell sample is a cell line.

In some embodiments, at least one cell in the cell sample is transfected or infected by methods known in the art. In some embodiments, the cell sample is infected by a viral vector, e.g., a virus that includes a nucleic acid that encodes at least one protein of interest. Exemplary viral vectors include adenoviruses (reviewed in Altaras et al., 2005, *Adv. Biochem. Eng. Biotechnol.*, 99:193-260), adeno-associated viruses (reviewed in Park et al., 2008, *Front. Biosci.*, 13:2653-59; see also Williams, 2007, *Mol. Ther.*, 15:2053-54), parvoviruses, lentiviruses, retroviruses (reviewed in Tai et al., 2008, *Front. Biosci.*, 13:3083-95), and the herpes simplex virus. Methods of delivery of nucleic acids are reviewed in Patil et al., 2005, *AAPS J.*, 7:E61-77, which is incorporated herein by reference in its entirety.

In some embodiments, the cell sample is a primary cell culture sample. The primary cell culture sample comprises cells dissociated from fresh tissue samples. Additional nutrients may be supplemented to the culture medium according to specific cell types (e.g., neuron, epithelial cells, or endothelial cells) to maintain cell viability. In some embodiments, the cell sample is an immortalized cell line (e.g., a human cell line) sample. In some embodiments, the cell sample comprises adherent cells and/or suspension cells.

In some embodiments, overall viability of cells in the cell sample is at least or about 60%, at least or about 65%, at least or about 70%, at least or about 75%, at least or about 80%, at least or about 85%, at least or about 90%, at least or about 95%, at least or about 96%, at least or about 97%, at least or about 98%, at least or about 99%, or 100%.

In some embodiments, the biological sample is a three dimensional (3D) culture sample. In some embodiments, the 3D culture sample is an organoid sample (e.g., comprising one or more types of organoids). In some embodiments, the 3D culture sample is a spheroid sample (e.g., comprising one or more types of spheroids). In some embodiments, the biological sample is embedded in hydrogels.

In some embodiments, the biological sample is from a human (e.g., human patients). In some embodiments, the biological sample is from an animal model (e.g., mice).

The analyte can be any analyte disclosed herein, or multiples thereof. In some instances, the analyte is a nucleic acid. In some instances, the analyte is a protein. In some instances, both a nucleic acid analyte and a protein analyte are measured from the same sample. In some instances, the methods disclosed herein include measuring and/or determining the relative abundance of an analyte compared to a reference sample. In some instances, the methods disclosed herein include determining the tertiary or quaternary structure of the analyte. In some instances, the methods disclosed herein identify one or more post-translational modifications on an analyte. This includes, without limitation, the presence and abundance of one or more post-translational modifications. In some instances, the methods disclosed herein determine the enzymatic activity of an analyte.

In some instances, the methods disclosed herein determine the location of an analyte. In some instances, the location of the analyte is fluid over time. That is, the location of an analyte can vary depending on its function. For example, in some instances, the methods disclosed herein allow a user to determine analyte translocation or trafficking across any organelle in the cell (e.g., as described herein). In some instances, translocation or trafficking occurs in or around an endoplasmic reticulum (ER) in a cell. In some instances, translocation or trafficking occurs in or around a Golgi apparatus in a cell. In some instances, an analyte can be detected as associating with a cell or nuclear membrane surface.

In some embodiments, the biological sample is treated with a blocking reagent described herein. In some instances, the blocking reagent can prevent molecular (e.g., test compounds or drugs described herein) or cellular (e.g., live cells) adhesion to a capture probe.

(b) Perfusion Chamber

Figure 10A:
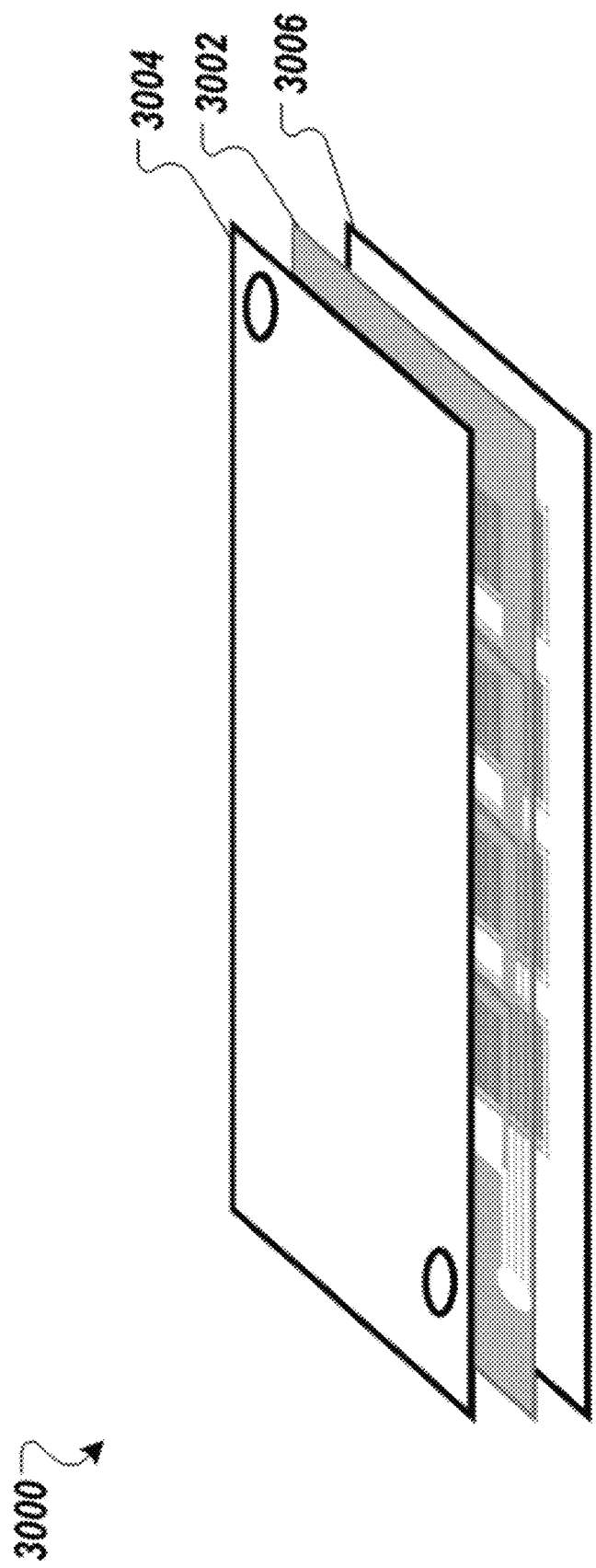
FIG. 10A shows a schematic perspective view of an example system.
Figure 10B:
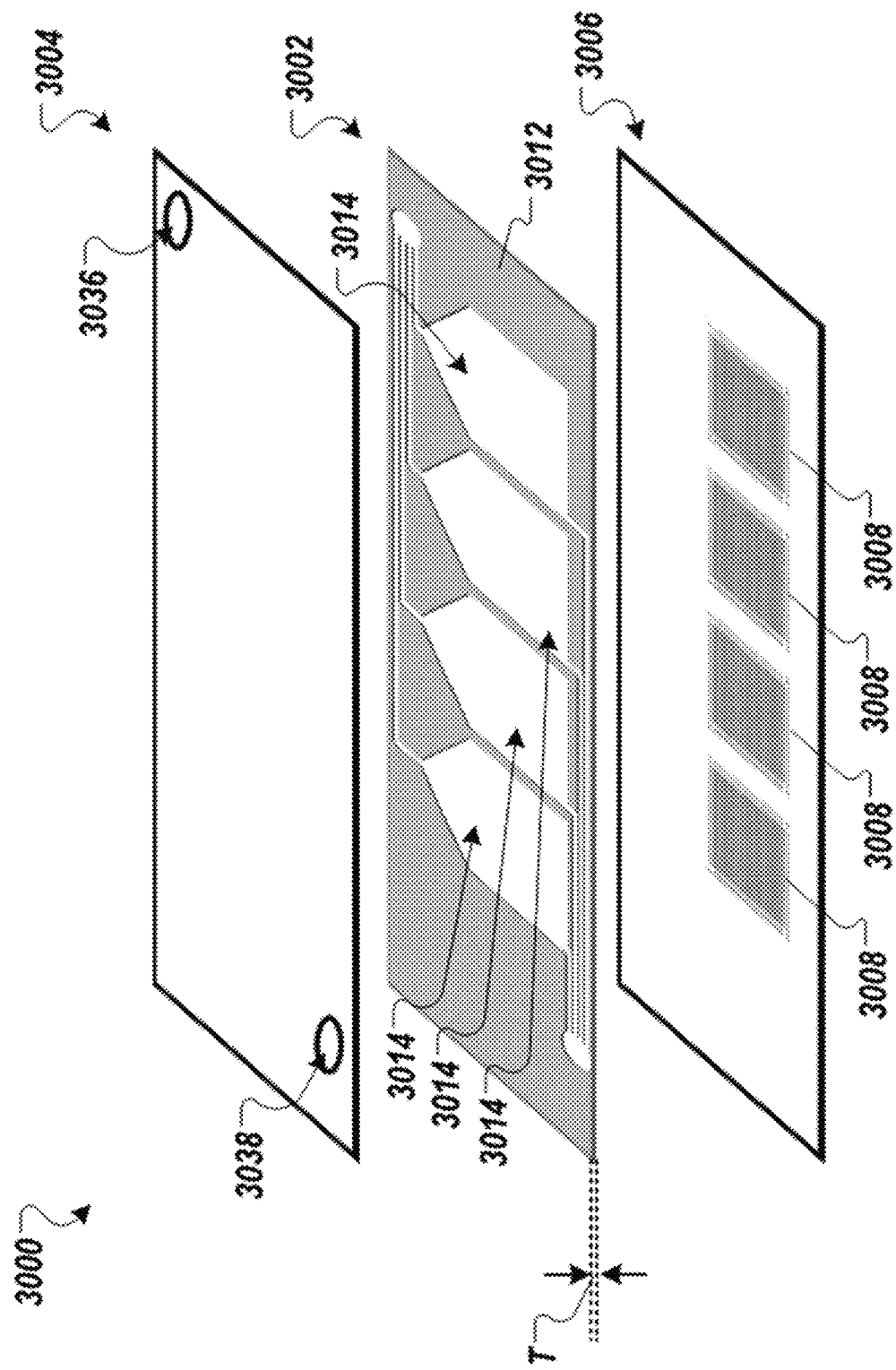
FIG. 10B shows an exploded view of an example system in FIG. 10A.

Referring to FIGS. 10A-10B and 11A-11C, an example system 3000 is described which can be used for capturing temporal aspects of gene expression in a biological sample. FIG. 10A is a schematic perspective view of the system 3000, and FIG. 10B is an exploded view of the system 3000 of FIG. 10A. As described herein, the system 3000 is configured to define one or more chambers that can be used for measuring cellular activity or gene expression in a biological sample. In some embodiments, a chamber is an array area of a spatial transcriptomics slide, for example an array area of a Visium gene expression slide wherein the array area comprises a plurality of capture probes as described herein.

The system 3000 can include a gasket 3002 and a cover 3004. The system 3000 may further include a substrate 3006. In general, as illustrated in FIG. 10A, the gasket 3002 and the cover 3004 are configured to be reversibly mounted onto the substrate 3006 to define chambers that contain biological samples placed on the substrate 3006. Such chambers can be used as perfusion chambers into which fluids are introduced for various analyses, such as measuring cellular activities or gene expression. As described herein, the system 3000 is configured to be able to achieve laminar flow so that multiple samples (e.g., cells, tissues, etc.) can be contacted with fluid at the same time.

Figure 11A:
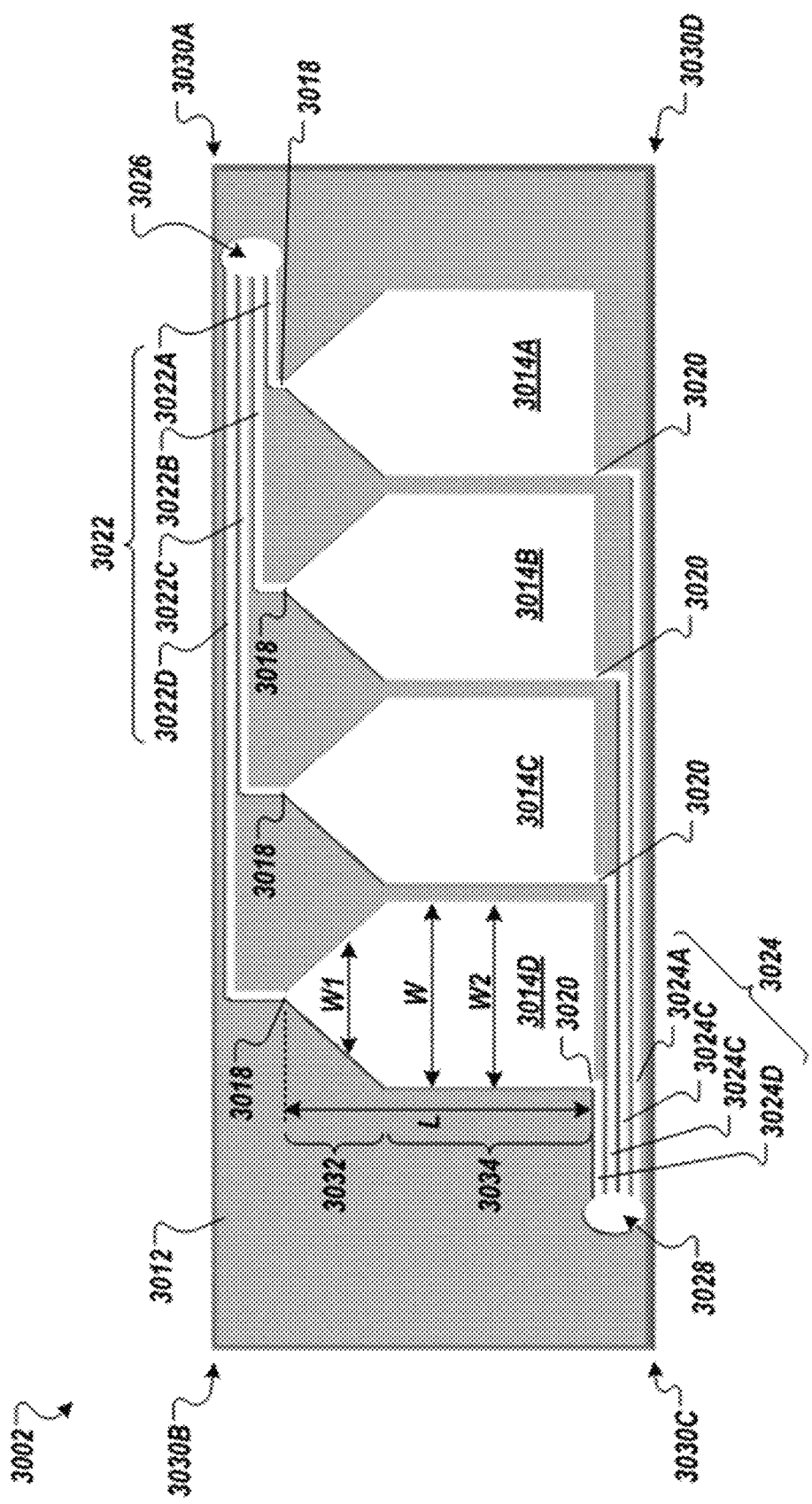
FIG. 11A shows a top view of an example gasket.
Figure 11B:
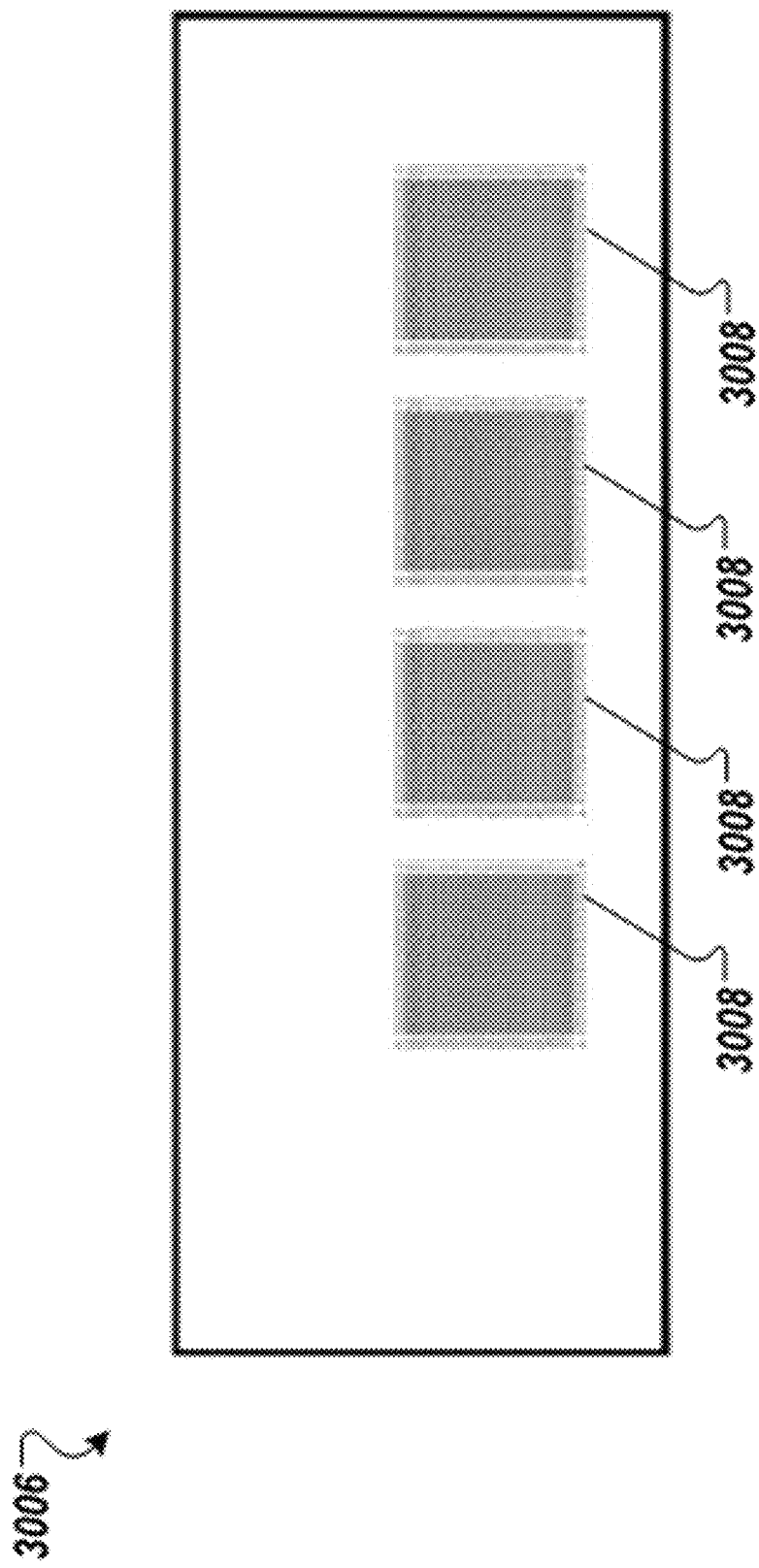
FIG. 11B shows a top view of an example substrate.

As shown in FIGS. 10B and 11B, the substrate 3006 includes one or more substrate regions 3008, each of which is configured to receive a biological sample. In some implementations, the substrate 3006 includes a plurality of substrate regions 3008 for placing a plurality of samples. The substrate regions 3008 can comprise a plurality of capture probes, as described herein. The capture probes can include a spatial barcode and a capture domain that binds to a sequence present in an analyte. The substrate regions 3008 can be arranged on the substrate 3006 in various two-dimensional arrays. In the illustrated example, the substrate 3006 has four substrate regions 3008 arranged in line (i.e., a one by four array). However, other configurations are possible. By way of example, eight substrate regions 3008 can be arranged in a two by four array. In some instances, the substrate 3006 includes at least 1, 2, 3, 4, 5, 6, 7, 8, 9, 10, 12, 14, 16 or more substrate regions 3008. In some instances, the substrate regions 3008 are arranged in one row (e.g., a one by two, one by three, one by four array, or an array of one by any suitable number). In some instances, the substrate regions 3008 are arranged in two rows (e.g., a two by two, two by three, two by four array, or an array of two by any suitable number). The substrate regions 3008 can be arranged in a symmetrical array (e.g., an array of two by two, two by three, two by four, etc.) or a non-symmetrical array (e.g., an array that has a first number of substrate regions in a first column and a second number (different from the first number) of substrate regions in a second column).

Figure 11C:
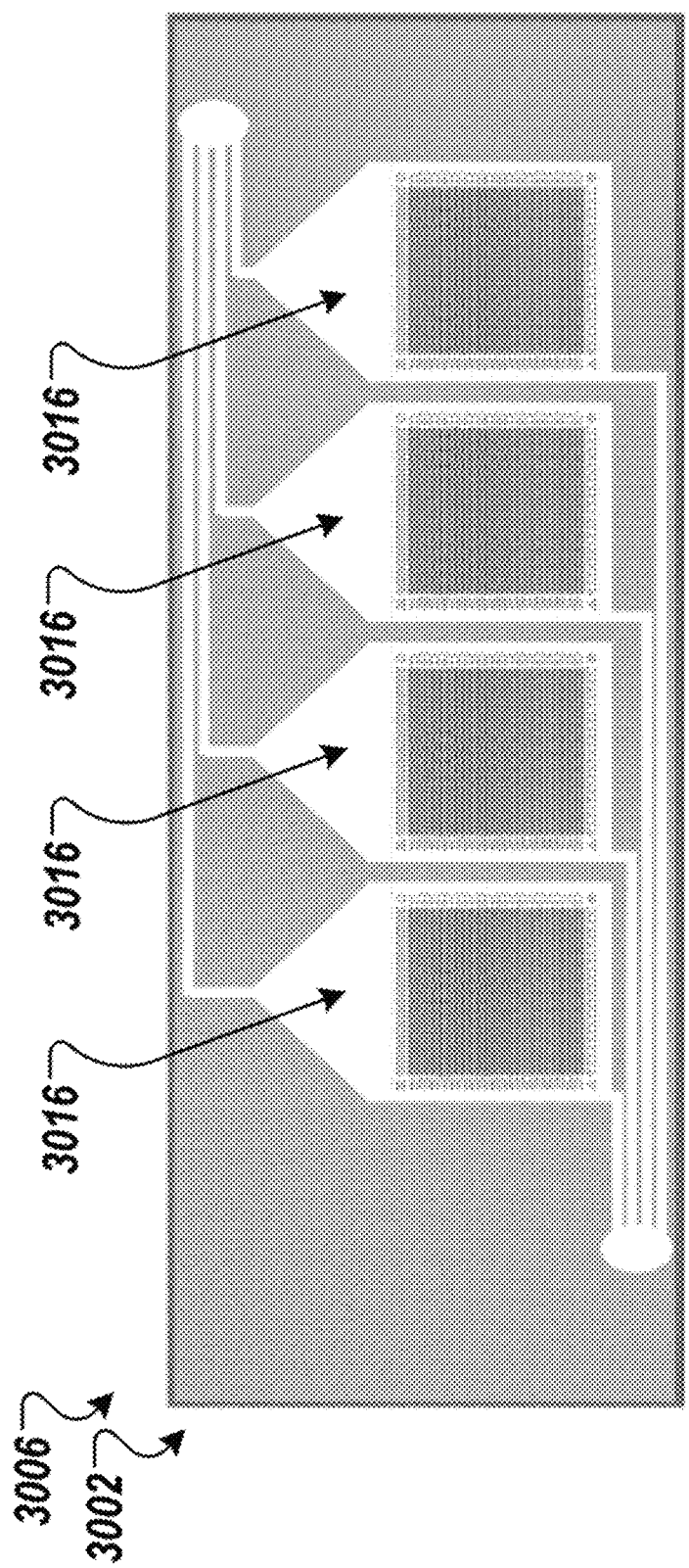
FIG. 11C shows a top view of an example gasket disposed on an example substrate.

The gasket 3002 includes a gasket body 3012 and one or more apertures 3014 defined in the gasket body 3012. The gasket 3002 is configured to be reversibly disposed onto the substrate 3006. In some implementations, the gasket 3002 includes the same number of apertures 3014 as the substrate regions 3008 of the substrate 3006. Alternatively, the gasket 3002 may have more or less apertures 3014 than number of the substrate regions 3008. The apertures 3014 are arranged to correspond to the substrate regions 3008 when the gasket 3002 is positioned on the substrate 3006. For example, when the gasket 3002 is disposed on the substrate 3006, the apertures 3014 of the gasket 3002 are aligned with the substrate regions 3008 of the substrate 3006, respectively, thereby defining a plurality of chambers 3016, as shown in FIG. 11C. As described herein, the plurality of chambers 3016 are used as perfusion chambers for biological samples on the substrate 3006. In some embodiments, the plurality of chambers 3016 allow for independent experiments or replicates run on one substrate 3006.

Each aperture 3014 can have at least two ports through which fluid can flow into and out from the aperture 3014. For example, the aperture 3014 can include an inlet port 3018 and an outlet port 3020 as shown in FIG. 11A. Conversely, the aperture 3014 can include an inlet port 3020 and an outlet port 3018. The inlet port 3018 is configured to permit fluid to enter the aperture 3014 (or the chamber 3016 defined at least by the aperture 3014), and the outlet port 3020 is configured to permit fluid to exit the aperture 3014 (or the chamber 3016 defined at least by the aperture 3014).

The gasket 3002 further includes one or more input channels 3022 and one or more output channels 3024. The input channels 3022 can be at least partially enclosed by the substrate 3006 and the cover 3004 when the gasket 3002 is sandwiched between the substrate 3006 and the cover 3004, so that fluid can flow along the input channels 3022. Similarly, the output channels 3024 can be at least partially enclosed by the substrate 3006 and the cover 3004 when the gasket 3002 is disposed between the substrate 3006 and the cover 3004, so that fluid can flow along the output channels 3024.

The inlet ports 3018 are fluidly connected to the input channels 3022, respectively. Accordingly, the input channels 3022 are fluidly connected to the apertures 3014 through the inlet ports 3018, respectively. The outlet ports 3020 are fluidly connected to the output channels 3024, respectively. Accordingly, the output channels 3024 are fluidly connected to the apertures 3014 through the outlet ports 3020, respectively. FIG. 11A shows the gasket 3002 can include an upstream bore 3026 and a downstream bore 3028, or vice versa. The upstream bore 3026 is fluidly connected to the input channels 3022 so that the input channels 3022 extend commonly from the upstream bore 3026. Accordingly, the input channels 3022 extend between the upstream bore 3026 and the inlet ports 3018 of the apertures 3014, respectively. The downstream bore 3028 is fluidly connected to the output channels 3024 so that the output channels 3024 extend commonly from the downstream bore 3028. Accordingly, the output channels 3024 extend between the downstream bore 3028 and the output ports 3020 of the apertures 3014, respectively.

Although the gasket 3002 is primarily described as having a single upstream bore 3026 for all the input channels 3022 and a single downstream bore 3028 for all the output channels 3024, alternative configurations are possible. For example, the gasket 3002 can include multiple upstream bores 3026, and at least one of the multiple upstream bores 3026 is fluidly connected to multiple input channels 3022. Similarly, the gasket 3002 can include multiple downstream bores 3028, and at least one of the multiple downstream bores 3028 is fluidly connected to multiple output channels 3024. In other examples, the gasket 3002 can include multiple upstream bores 3026 for respective input channels 3022, and/or multiple downstream bores 3028 for respective output channels 3024.

In some implementations, at least two or more of the input channels 3022 have different lengths between the upstream bore 3026 and the respective inlet ports 3018. For example, in the illustrated example of FIG. 11A, the input channels 3022 includes first, second, third, and fourth input channels 3022A-3022D, and the first, second, third, and fourth input channels 3022A-3022D have different lengths L1-L4 that are determined as distances of routes or paths between the upstream bore 3026 and the respective inlet ports 3018 of the apertures 3014. Alternatively or in addition, at least two of the input channels 3022 can have the same length between the upstream bore 3026 and the respective inlet ports 3018. By way of example, the upstream bore 3026 can be positioned between a group of first and second apertures 3014A-B and a group of third and fourth apertures 3014C-D (e.g., where the upstream bore 3026 is positioned along a hypothetical line that splits the two groups), and the first and second input channels 3022A-B can have the same lengths as the third and fourth input channels 3022C-D, respectively.

In addition or alternatively, at least two or more of the output channels 3024 have different lengths between the downstream bore 3028 and the respective outlet ports 3020. For example, in the illustrated example of FIG. 11A, the output channels 3024 includes first, second, third, and fourth input channels 3024A-D, and the first, second, third, and fourth input channels 3024A-D have different lengths L5-L8 that are determined as distances of routes or paths between the downstream bore 3028 and the respective outlet ports 3020 of the apertures 3014. Alternatively or in addition, at least two of the outlet channels 3024 can have the same length between the downstream bore 3028 and the respective outlet ports 3020. By way of example, the downstream bore 3028 can be positioned between the group of first and second apertures 3014A-B and the group of third and fourth apertures 3014C-D (e.g., where the downstream bore 3028 is positioned along a hypothetical line that splits the two groups), and the first and second output channels 3024A-B can have the same lengths as the third and fourth output channels 3024C-D, respectively.

The upstream bore 3026 and the downstream bore 3028 can be arranged in various positions in the gasket 3002. In some implementations, as illustrated in FIG. 11A, the upstream bore 3026 can be positioned to be opposite to the downstream bore 3028 with respect to the group of the apertures 3014. For example, the gasket 3004 has a rectangular shape of the gasket body 3012 with four corners 3030A-D. The upstream bore 3026 can be positioned at a first corner 3030A of the gasket body 3012, and the downstream bore 3028 can be positioned it a third corner 3030C that is opposite to the first corner 3030A. In other implementations, the upstream bore 3026 can be positioned to be opposite to the downstream bore 3028 relative to a center C of the gasket 3002. Other positions of the upstream bore 3026 and the downstream bore 3028 are also possible to provide suitable fluid stream into and out from the apertures 3014.

In some implementations, the inlet/input features (e.g., the inlet port 3018, the input channels 3022, the upstream bore 3026, etc.) can be reversed with the outlet/output features (e.g., the outlet port 3020, the output channels 3024, the downstream bore 3028, etc.). For example, the outlet/output features can be used for receiving fluid and the inlet/input features can be used for discharging the fluid.

The gasket 3002 can be made of one or more various materials. The gasket 3002 can be made of a material that provides appropriate seals at the interface between the gasket 3002 and the substrate 3006, and at the interface between the gasket 3002 and the cover 3004, so that fluid paths are sealingly defined along the input channels 3022, the chambers 3016 (defined at least by the apertures 3014), and the output channels 3024 in the system 3000 without leakage between adjacent fluid paths or leakage from the system 3000 as a whole. In some implementations, the gasket 3002 can be made of silicone. Alternatively, the gasket 3002 can be made of natural rubber, nitrile rubber, polytetrafluoroethylene (PTFE), for example. In some instances, the gasket is reversibly applied and connected to the cover 3004 and/or the substrate 3006.

The gasket 3002 can be configured in various dimensions. In some implementations, the gasket 3002 has a thickness T that ranges between 0.1 mm and 5.0 mm. In other implementations, the thickness T of the gasket 3002 can range between 0.6 mm and 1.0 mm. In yet other implementations, the thickness T of the gasket 3002 can be less than 0.1 mm. In yet other implementations, the thickness T of the gasket 3002 can be greater than 5.0 mm.

The apertures 3014 of the gasket 3002 can be configured in various dimensions. Each aperture 3014 can have an area that ranges between 40 $mm^2$ and 90 $mm^2$. Each aperture 3014 can have a volume that ranges between 2 $mm^3$ and 175 $mm^3$. The apertures 3014 can have the same area and volume. Alternatively, at least one of the apertures 3014 have a different area or volume from the other apertures 3014.

The apertures 3014 of the gasket 3002 can be configured in various shapes. For example, as shown in FIG. 11A, each aperture 3014 has a length L and a width W. In some implementations, the aperture 3014 can have the width W that varies at least partially along the length L. For example, the aperture 3014 includes a first portion 3032 and a second portion 3034. The first portion 3032 of the aperture 3014 includes the inlet port 3018, and the second portion 3034 of the aperture 3014 includes the outlet port 3020. The first portion 3032 has a first width W1, and the second portion has a second width W2. In some implementations, the first width W1 of the first portion 3032 can vary between the inlet port 3018 and the second portion 3034 (e.g., an end of the second portion 3034 that interfaces the inlet port 3018). For example, the first width W1 of the first portion 3032 can gradually increase from the inlet port 3018 to the interface between the first portion 3032 and the second portion 3034, so that the first portion 3032 has generally a triangular shape. In addition or alternatively, the second width W2 of the second portion 3034 can be consistent in the direction of the length L. The first width W1 of the first portion 3032 can be identical to the second width W2 of the second portion 3034 at the interface between the first portion 3032 and the second portion 3034.

Figure 17:
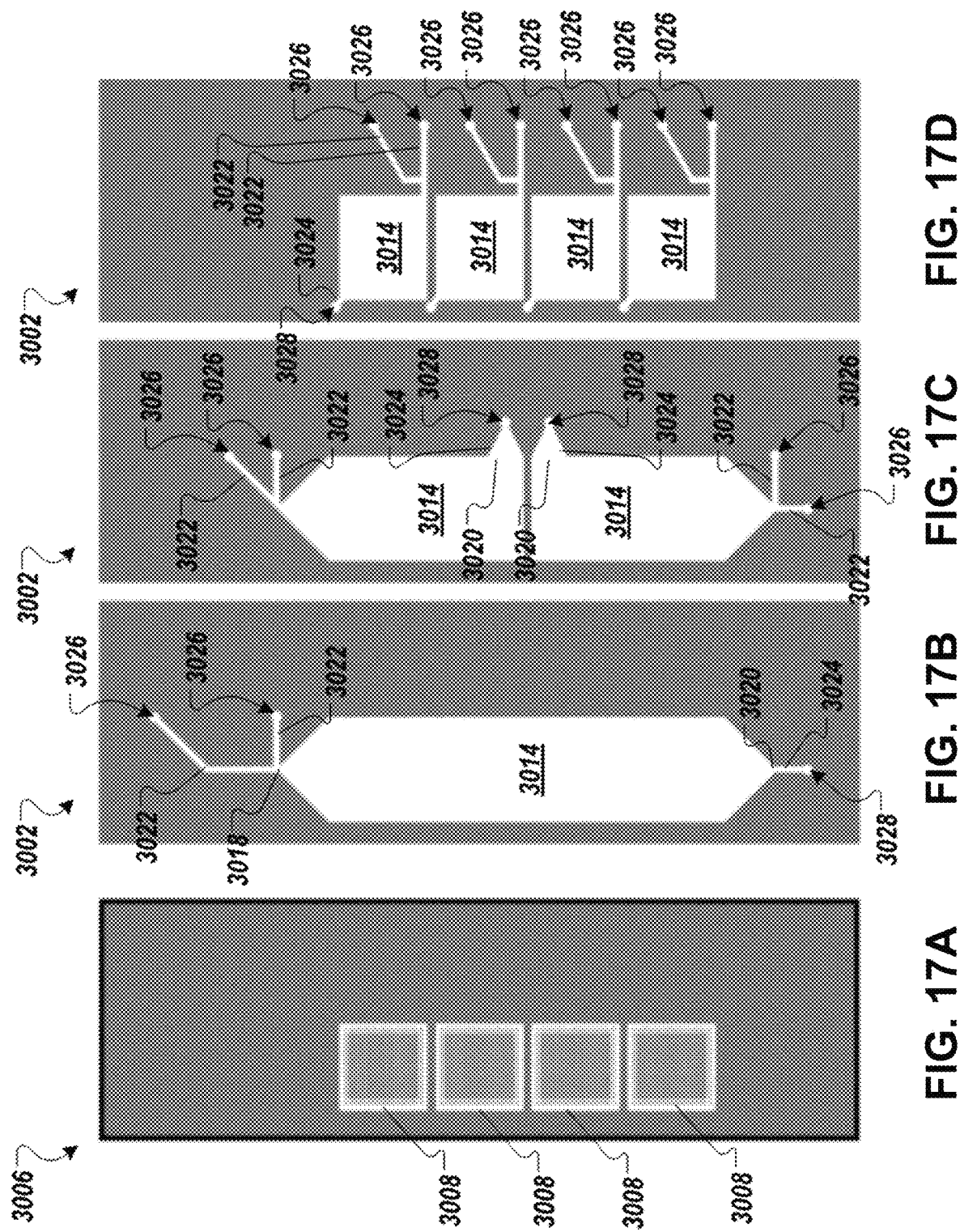
FIGS. 17A-17D show exemplary gasket configurations.

In other examples, the aperture 3014 of the gasket 3002 can have different configurations. For example, as illustrated in FIG. 17D, the aperture 3014 can be shaped as a square or rectangular that has a consistent width along the length. Other suitable shapes, such as circular, oval, hexagonal, etc. are also possible.

In some implementations, the gasket 3002 can include the number of apertures 3014 that is identical to the number of the substrate regions 3008 of the substrate 3006, so that the apertures 3014 are aligned with the respective substrate regions 3008, as shown in FIGS. 11C and 17D. In other implementations, the gasket 3002 can have the apertures 3014 less than the substrate regions 3008 of the substrate 3006 so that at least one of the apertures 3014 is aligned with a plurality of substrate regions 3008. For example, as illustrated in FIGS. 17A and 17C, where the substrate 3006 has four substrate regions 3008, the gasket 3002 can have two apertures 3014 that is each configured to align with two of the substrate regions 3008. In this configuration, fluid that is introduced into each aperture 3014 runs through two substrate regions 3008. In another example, as illustrated in FIG. 17B, the gasket 3002 has a single aperture 3014 configured to align with four substrate regions 3008 of the substrate 3006, so that fluid that is introduced into the aperture 3014 is commonly supplied to all the four substrate regions 3008. In yet other implementations, the gasket 3002 can have the apertures 3014 more than the substrate regions 3008 of the substrate 3006 so that at least one of the substrate regions 3008 can be aligned with two or more apertures 3014.

In some implementations, each aperture 3014 can have a single input channel 3022 and a single output channel 3024, as shown in FIG. 11A. In other implementations, each aperture 3014 can have multiple input channels 3022 and/or multiple output channels 3024. By way of example, in FIGS. 17B-17D, each aperture 3022 has two input channels 3022.

In some implementations, the input channels 3022 and/or the output channels 3024 can have a consistent width along their lengths, as illustrated in FIGS. 11A and 17B-17D. In other implementations, the input channels 3022 and/or the output channels 3024 can have varied widths along their lengths. By way of example, as illustrated in FIG. 17C, the output channels 3024 can have a width that decreases from the output port 3020 to the downstream bore 3028.

Referring to FIGS. 10A-10B, the cover 3004 is configured to be positioned on the gasket 3002. For example, the cover 3004 can be mounted onto the gasket 3002 opposite to the substrate 3006, so that the plurality of chambers 3016 are defined in the system 3000.

The cover 3004 can include an inlet 3036 and an outlet 3038. The inlet 3036 is positioned such that the inlet 3036 is fluidly connected to the plurality of input channels 3022 of the gasket 3002 when the cover 3004 is mounted onto the gasket 3002. The inlet 3036 can be used to introduce fluid into the system 3000 (e.g., into the chambers 3016 defined at least part by the apertures 3014 of the gasket 3002). For example, the inlet 3036 can be aligned with the upstream bore 3026 of the gasket 3002 when the cover 3004 is disposed on the gasket 3002.

The outlet 3038 is positioned such that the outlet 3038 is fluidly connected to the plurality of output channels 3024 of the gasket 3002 when the cover 3004 is mounted onto the gasket 3002. The outlet 3038 can be used to discharge fluid from the system 300 (e.g., from the chambers 3016 defined at least part by the apertures 3014 of the gasket 3002). For example, the outlet 3038 can be aligned with the downstream bore 3028 of the gasket 3002 when the cover 3004 is disposed on the gasket 3002.

In the illustrated example, the cover 3004 includes a single inlet 3036 and a single outlet 3038 for multiple chambers 3016 (FIG. 11C). In other implementations, the cover 3004 can have multiple inlets 3036 and/or multiple outlets 3038 for respective ones of at least some of the multiple chambers 3016.

The cover 3004 can be made of one or more various materials. In some implementations, the cover 3004 is made of plastic. In other implementations, the cover 3004 can be made of Silica glass, Quartz, Polystyrene, PLA (Poly Lactic Acid), Acrylic or Polymethyl Methacrylate (PMMA), Polycarbonate (PC), Polyethylene (PE), Polypropylene (PP), Polyethylene Terephthalate (PETE or PET), Polyvinyl Chloride (PVC), and/or Acrylonitrile-Butadiene-Styrene (ABS), or other suitable materials.

In some implementations, as illustrated in FIGS. 10A-10B, the cover 3004 is separately made and disposed on the gasket 3002. Alternatively, the cover 3004 and the gasket 3002 can be made in a single piece that can be placed on a substrate in the same or similar way as described herein. In some embodiments, the cover 3004 and the gasket 3002 are reversibly placed on the substrate, for example for removal during downstream processing of the sample located in one or more of the chambers on the substrate.

(c) Substrates Comprising Multi-Well Plates

In some embodiments, a substrate described herein comprises a multi-well plate and includes one or more wells, each of which is configured to receive a biological sample. In some implementations, the multi-well plate includes a plurality of wells for placing a plurality of samples. In some embodiments, the plurality of capture probes, as described herein, are directly attached to the wells. For example, the capture probes are directly printed at a surface (e.g., a bottom surface) in the wells. In some embodiments, the plurality of capture probes are attached (e.g., printed) to a substrate, e.g., a coverslip, and the substrate is placed within the wells. In some embodiments, the coverslips are custom made to fit within the multi-well plate. In some embodiments, the coverslip comprises plastic (e.g., polystyrene plastic), metal, glass, or any materials compatible for attachment of the capture probes. In some embodiments, the capture probes are attached to the wells or the substrate chemically, e.g., via one or more linkage groups. In some embodiments, the linkage groups include amide groups, epoxides, thiol, Acrydite™. In some embodiments, the well or the substrate has additional surface chemistry to facilitate the growth and/or attachment of cells as known in the art. In some embodiments, the well (e.g., a polystyrene microplate well) or the substrate (e.g., a polystyrene coverslip) is exposed to a plasma gas to order to modify the hydrophobic plastic surface to make it more hydrophilic. The resulting surface carries a net negative charge due to presence of oxygen-containing functional groups (e.g., hydroxyl and/or carboxyl groups). In some embodiments, the well or the substrate is coated with poly-lysine and/or collagen. Details can be found, e.g., in Curtis et al., The *Journal of Cell Biology* 97.5 (1983): 1500-1506, which is incorporated herein by reference in its entirety.

Figure 18:
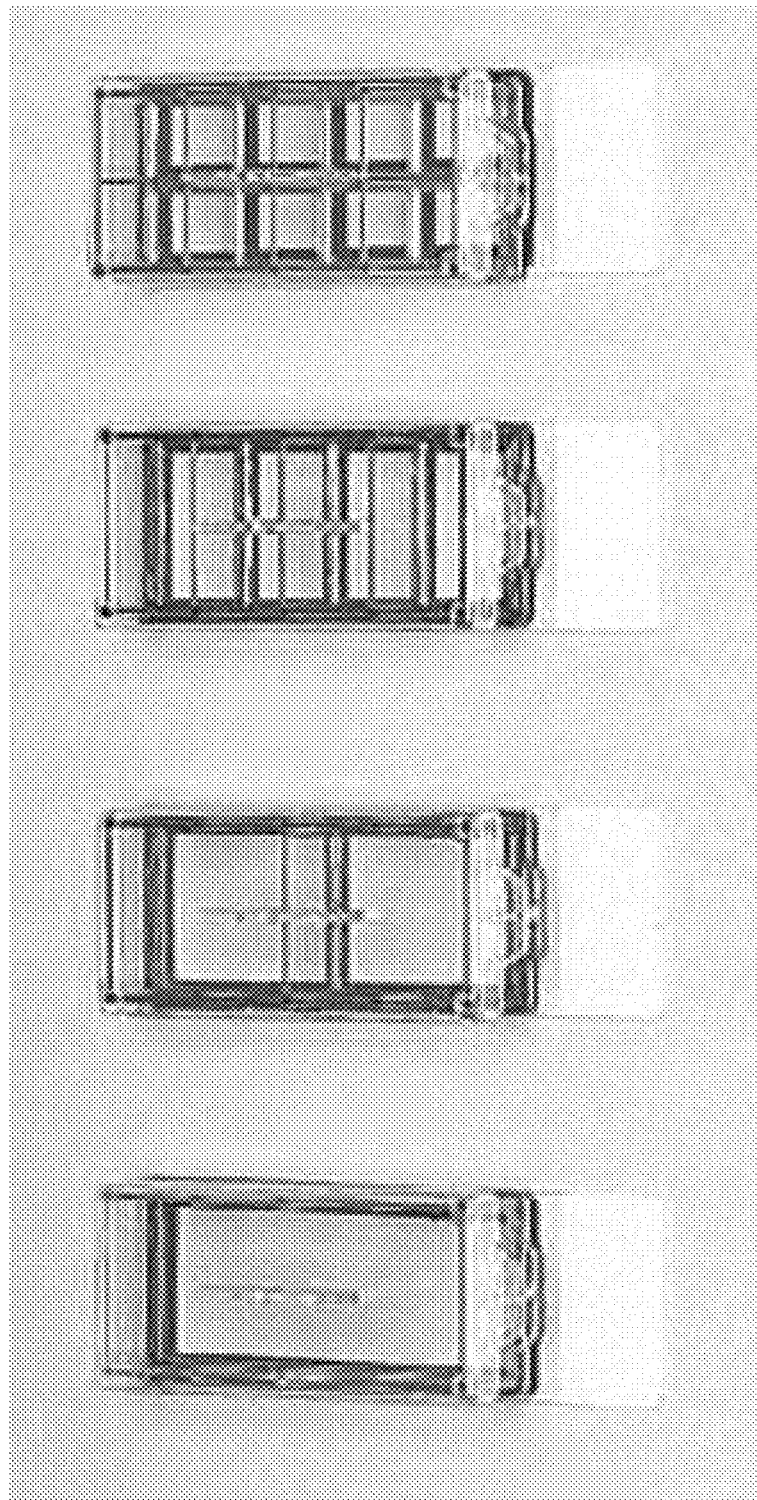
FIG. 18 shows exemplary multi-well tissue culture plate configurations.

In some embodiments, the wells can be arranged in the multi-well plate in various two-dimensional ways. For example, as illustrated in FIG. 18, a multi-well plate can have a single well; two wells arranged in line (i.e., a one by two plate); or four wells arranged in line (i.e., a one by four plate). However, other configurations are possible. By way of example, eight wells can be arranged in a two by four plate. In some instances, the multi-well plate includes at least 1, 2, 3, 4, 5, 6, 7, 8, 9, 10, 12, 14, 16, 24, 48, 96, 384, or more one or more wells. In some instances, the wells are arranged in one row (e.g., a one by two, one by three, one by four plate, or a plate of one by any suitable number). In some instances, the wells are arranged in two rows (e.g., a two by two, two by three, two by four plate, or a plate of two by any suitable number). The wells can be arranged in a symmetrical plate (e.g., a plate of two by two, two by three, two by four, etc.) or a non-symmetrical array (e.g., a plate that has a first number of wells in a first column and a second number (different from the first number) of wells in a second column).

In some embodiments, the multi-well plate described herein is assembled by mounting a gasket comprising a plurality of apertures (e.g., any one of the gasket described herein) onto a substrate comprising a plurality of substrate regions (e.g., a spatial array slide). Thus, a well of the assembled multi-well plate is defined by the substrate region of the substrate, and the aperture of the gasket. In some embodiments, the gasket is configured to be mounted onto the substrate such that the plurality of apertures are aligned with the plurality of substrate regions, respectively. The configuration of the substrate regions and apertures of the assembled multi-well plate can be any one of the configurations described herein. In some embodiments, the assembled multi-well plate is disassembled after permeabilizing the biological sample (e.g., a live tissue sample or cell sample), and the substrate (e.g., the spatial array slide) is subjected to spatial analysis.

In some embodiments, tissue culture dishes useful in methods disclosed herein include, but are not limited to, 35 mm, 60 mm, 100 mm, 150 mm diameter dishes as well as flasks T-25, T-27, T-175, T-225. In some embodiments, multi will plates includes multi-layer flasks. Methods disclosed herein can further include microfluidic culture chips (e.g., chips manufactured by Darwin Microfluidics, Paris, France).

In some embodiments, the multi-well plate is commercially available. For example, the multi-well plate described herein is a 6-well plate, an 8-well plate, a 12-well plate, a 24-well plate, a 48-well plate, a 96-well plate or a 384-well plate. In some embodiments, the multi-well plate is custom made, e.g., to accommodate specific needs (e.g., automatic detection of cellular activities or intracellular gene expressions). In some embodiments, the multi-well plate is heat-resistant, such that the plate is compatible with one or more steps of the spatial analysis described here (e.g., reverse transcription and/or PCR amplification). In some embodiments, the spatial gene expression of tissues or cells is obtained within each individual well of the multi-well plate. In some embodiments, the multi-well plate is capable of automatic detection (e.g., plate-based scanning) of cellular activity and/or the intracellular gene expression as described herein.

In some embodiments, the well or the substrate described herein comprises one or more fiducial markers. For example, the fiducial markers can allow for proper orientation, detection, and/or rotation of the sample on the substrate. In some instances, the fiducial markers provide a visual reference of the biological sample (e.g., one or more cells in the biological sample) in respect to the substrate.

(d) Methods of Measuring Cellular Activity

In one aspect, cellular activity of a biological sample can be recorded using the methods as described herein. Examples of cellular activity can include, but are not limited to: protein activity (e.g., kinase activity), phosphorylation activity, G protein-coupled receptor related activity, ion channel activity (e.g., switch between open and closed conformation), ligand-receptor binding activity, neural activity (e.g., neuronal action potentials), protein synthesis (e.g., transcription or translation) activity, protein expression and localization (e.g., sub-cellular organelle protein expression and trafficking), transient optical activity (e.g., optical reporter gene expression), cell-to-cell interaction, cellular morphology, vesicular trafficking (e.g., exocytosis or endocytosis), protein translocation and/or protein post-translational modifications (e.g., ubiquitination or glycosylation). In some embodiments, the cellular activity includes processes in cell signaling pathways or cascades. In some embodiments, the cellular activity includes conformational changes of biomolecules (e.g., proteins or nucleic acids). In some embodiments, the cellular activity is that which occurs upon contacting one or more cells with a pharmacological compound. For example, the detection of apoptosis of one or more cells is recorded pre and post addition of, for example, a drug that may or may not be useful in treating cancers or other aberrant cellular proliferation diseases. As such, the methods described herein can be used in drug discovery. Additionally, the present methods can be used to track or monitor the success or failure of a patient being treated with a drug or medicament, for example by tracking the presence or absence of the desired cellular activity that is expected to occur when a patient is treated with the desired drug or medicament. Therefore, the present methods can be used to help determine a treatment regimen for a patient, track or monitor the success of that treatment during therapy and track or monitor post therapeutic treatment success or relapse.

In some embodiments, the methods include a recording step of the biological sample. In some instances, the biological sample is a live tissue section as described herein. In some instances, the biological sample is a culture of cells as described herein. The recording detects one or more of the cellular activities disclosed herein. In some instances, the recording step comprises optical recording. In some instances, optical recording includes measuring of membrane potential activity. In some instances, optical recording captures fast (approximately 1 msec) cellular electrical activity such as ion channel activity (e.g., switch between open and closed conformation) or neural activity (e.g., neuronal action potentials). In some instances, optical recording includes using chemical dyes or indicators. In some embodiments, the chemical dye or indicator comprises a fluorophore, such that the fluorescent signal, or lack thereof, can be recorded in order to detect one or more cellular activities. In some instances, the recording step comprises electrical recording.

In some embodiments, the chemical dye is a voltage-sensitive dye, a pH-sensitive dye, a temperature-sensitive dye, a light-sensitive dye, an oxygen-sensitive dye, a metal sensitive dye, or any chemical dyes that can be used to track one or more cellular activities as described herein.

In some embodiments, the chemical dye is a voltage-sensitive dye. Voltage-sensitive dyes, also known as potentiometric dyes, are dyes which change their spectral properties in response to voltage changes. They are able to provide linear measurements of firing activity of single neurons, large neuronal populations or activity of myocytes. Many physiological processes are accompanied by changes in cell membrane potential which can be detected with voltage sensitive dyes. Measurements may indicate the site of action potential origin, and measurements of action potential velocity and direction may be obtained.

In some instances, potentiometric dyes can be used to monitor the electrical activity inside cell organelles where it is not possible to insert an electrode, such as the mitochondria and dendritic spine. This technology is powerful for the study of patterns of activity in complex multicellular preparations. It also makes possible the measurement of spatial and temporal variations in membrane potential along the surface of single cells.

In some embodiments, the voltage-sensitive dye may be contacted with the biological sample using a contact method chosen from: intravenous injection; intramuscular injection; intraventricular injection; spinal tap; craniotomy with direct contact of dye to cortical surface of the tissue sample (e.g., a brain tissue sample).

Non-limiting examples of suitable voltage-sensitive dyes include, but are not limited to: merocyanine-rhodamine dyes including NK 2761; minonaphthylethenylpyridinium dyes including Di-4-ANEPPS, di-8-ANEPPS, Di-2-ANEPEQ, Di-8-ANEPPQ and Di-12-ANEPPQ; dialkylaminophenylpolyenylpyridinium dyes including RH 160, RH 237, RH 414, RH 421, and RH 795; oxonol dyes including RH 155, RH 482, RH 1691, RH 1692, and RH 1838; and dipicrylamine (DPA).

In some instances, the voltage-sensitive dye includes a membrane-localized voltage-sensitive protein coupled to a capture protein. In some embodiments, the capture protein is arranged and disposed to capture small-molecule fluorescent dyes. In some embodiments, the voltage sensitive protein is an opsin, such as, but not limited to, a microbial opsin. Suitable microbial opsins include, but are not limited to, QuasAr2, Ace2N, or a combination thereof. In some embodiments, the voltage sensitive protein includes at least one voltage-sensing domain selected from the group consisting of a Ciona intestinalis voltage-sensing domain (CiVSD), Danio rerio voltage-sensing domain (DrVSD), Gallus gallus voltage-sensing domain (GgVSD), or a combination thereof. In some embodiments, a capture protein is a covalent capture protein. In one embodiment, the covalent capture protein is selected from the group consisting of HaloTag, SNAP-tag, TMP-tag, pLac-tag, CLIP-tag, or a combination thereof. In some embodiments, the capture protein is a non-covalent capture protein. In one embodiment, the non-covalent capture protein is selected from the group consisting of TMP-tag, biotin-avidin, and a combination thereof. A detailed description can be found, e.g., in U.S. Pat. No. 10,405,750, and in PCT Application Publication No. 2018102577A1, each of which is incorporated herein by reference in its entirety.

In some embodiments, the chemical dye is a calcium-sensitive dye, e.g., a calcium-sensitive fluorescent dye (or indicator). Imaging $Ca^{2+}$-sensitive fluorescent indicators provides a common approach for studying $Ca^{2+}$ signals in many contexts. Fluorescent indicators are particularly useful for measuring acute $Ca^{2+}$ changes in a relatively noninvasive manner. The availability of indicators that can be targeted to specific cellular domains, coupled with variations in affinity, brightness or spectral characteristics, provides tools for exploring spatially and temporally diverse $Ca^{2+}$ signals, and moreover, multiplexing the readout of $Ca^{2+}$ with other cellular functions. Non-limiting examples of fluorescent indicators to monitor intracellular $Ca^{2+}$ concentration include fluorescent protein reporters such as pericams, cameleons, modified yellow cameleons (YCs), and camgaroos. The $Ca^{2+}$ signals can also be measured with synthetic indicators such Fura-2, Indol-1, and Fluo-4. The procedures described can be applied to many imaging modalities, including wide-field, confocal, and total internal reflection (TIRF) microscopy. It is known in the art that the experimental details can vary depending on the cell type, imaging system, and characteristics of the $Ca^{2+}$ signals being studied. Using appropriate technology and suitable indicators, it is possible to monitor $Ca^{2+}$ signals spanning from subcellular to multicellular, at high speed or time lapse, within living cells. Details can be found in, e.g., Bootman, Martin D., et al. *Cold Spring Harbor Protocols* 2013.2 (2013): pdb-top066050; which is incorporated by reference in its entirety.

In some embodiments, the indicator is a genetically-encoded indicator, e.g., a genetically-encoded neural activity indicator, a genetically-encoded voltage indicator (GEVI) or a genetically-encoded calcium indicator (GCaMP). Genetically encoded voltage indicator (or GEVI) is a protein that can sense membrane potential in a cell and relate the change in voltage to a form of output, often fluorescent level. A GEVI is an optogenetic recording tool that enables exporting electrophysiological signals from cultured cells, live animals, including the human brain. Examples of notable GEVIs include ArcLight, ASAP1, ASAP3, and Ace2N-mNeon.

GEVI can have many configuration designs in order to realize voltage sensing function. An essential feature of GEVI structure is that it must situate on the cell membrane. Conceptually, the structure of a GEVI should permit the function of sensing the voltage difference and reporting it by change in fluorescence. Usually, the voltage-sensing domain (VSD) of a GEVI spans across the membrane and is connected to the fluorescent protein(s).

In some instances, by structure, GEVIs include at least four categories: (1) GEVIs that contain a fluorescent protein FRET pair, e.g., VSFP1, (2) single opsin GEVIs, e.g., Arch, (3) opsin-FP FRET pair GEVIs, e.g., MacQ-mCitrine, and (4) single FP with special types of voltage sensing domains, e.g. ASAP1. In some instances, the GEVI contains a fluorescent protein FRET pair. In some instances, the GEVI is a single opsin GEVI. In some instances, the GEVI is an opsin-FP FRET pair GEVI. In some instances, the GEVI is a single FP with special types of voltage sensing domains. A majority of GEVIs are based on the Ciona intestinalis voltage sensitive phosphatase (Ci-VSP or Ci-VSD (domain)). Some GEVIs might have similar components, but with different positioning of them. For example, ASAP1 and ArcLight both use a VSD and one FP, but the FP of ASAP1 is on the outside of the cell whereas that of ArcLight is on the inside, and the two FPs of VSFP-Butterfly are separated by the VSD, while the two FPs of Mermaid are relatively close to each other.

Non-limiting examples of GEVIs include FlaSh, VSFP1, SPARC, Flare, VSFP3.1, Mermaid, hVOS, Red-shifted VSFP's, PROPS, Zahra, Zahra 2, ArcLight, Arch, ElectricPk, VSFP-Butterfly, VSFP-CR, Mermaid2, Mac GEVIs, QuasAr1, QuasAr2, Archer, ASAP1, Ace GEVIs, ArcLightning, Pado, ASAP2f, FlicR1, Bongwoori, ASAP2s, ASAP-Y, (pa)QuasAr3(-s), Voltron(-ST), and/or ASAP3. Detailed descriptions can be found, e.g., in Xu et al., Current Opinion in Chemical Biology 39 (2017): 1-10; Bando et al. Cell Reports 26.3 (2019): 802-813, each of which is incorporated by reference in its entirety.

In some embodiments, the genetically-encoded indicator is a genetically-encoded calcium indicator (GECI, or GCaMP). GECI provides an alternative to synthetic indicators. GECIs can be easily targeted to specific cell types or sub-cellular compartments, and are compatible with long-term, repeated in vivo measurements. GECIs consist of a calcium-binding domain such as calmodulin or troponin C, fused to one or more (e.g., one, two, three, four, or more) fluorescent proteins (FPs). In single-FP GECIs, the fluorescence intensity of a circularly permuted FP (cpFP) is modulated by calcium binding-dependent changes in the chromophore environment. In two-FP GECIs and multiple-FP GECIs, calcium binding modulates fluorescence resonance energy transfer (FRET) between FPs. In some embodiments, GECIs are useful for screening for agonists or antagonists of G-protein coupled receptor (GPCR) or ion channels and monitoring neural activity. As a non-limiting example, intracellular calcium level changes induced by G-protein coupled receptor activation can be indicated by fluorescent signal changes emitted by GAcMP. Additional description can be found. e.g., in U.S. Pat. No. 9,518,980 B2, which is incorporated by reference in its entirety.

In some embodiments, the indicator discriminates between live and dead cells. For example, vitality dyes such as LIVE-OR-DYE dead cell dyes are cell membrane impermeable and amine-reactive. Such vitality stains can enter cells with damaged cell membranes, label intracellular proteins, and exhibit high levels of fluorescence. These vitality dyes can also react to cell surface proteins, however because cell surface proteins are less abundant than intracellular proteins the fluorescence associated with live cells is very low. Additional indicators include non-fluorescent dyes that only fluorescence when they enter cells such as live cell labeling or tracking dyes and cell proliferation dyes, for example Cytopainter live cell dyes are hydrophobic compounds that permeate across cell membranes and become highly fluorescent once inside the cell.

In some instances, the step of recording one or more cellular activities includes imaging the biological sample. In some instances, the sample is recorded before the sample is provided with one or more dyes or indicators. In some instances, the sample is recorded at the same time as when the sample is provided with one or more dyes or indicators. In some instances, the sample is recorded after the sample is provided with one or more dyes or indicators. In some instances, the sample is recorded before, during and/or after the sample is provided with one or more dyes or indicators. In some embodiments, temporal formation of cellular activities can be assessed using the methods described herein. For example, temporal (e.g., real-time) formation of the target cellular activity can be recorded by detecting and measuring the cellular activity (e.g., using dyes) by a fluorescent time lapse microscopy. Imaging can be performed using any of the microscopy techniques described herein. In some instances, imaging is performed using fluorescence microscopy, fluorescent time lapse microscopy, confocal microscopy, multi-photon microscopy (e.g., two-photon excitation microscopy), or any known microscopy techniques known in the art.

In some instances, after recording cellular activity, the sample is fixed. In some instances, the analytes in the sample can hybridize to a plurality of probes on an array (e.g., substrate) as described herein. In some instances, the poly-adenylation (poly(A)) sequence of an mRNA hybridizes to a poly-thymine (poly(T)) capture domain sequence on a capture probe. In some instances, the capture probe is extended using the analyte that is specifically bound to the capture domain as a template to generate an extended capture probe. In some instances, the extended capture probe is amplified to produce a plurality of extended capture probes. In some instances, the plurality of extended capture probes, or libraries created therefrom, is sequenced. In some instances, all or a portion of the sequence of the spatial barcode, or a complement thereof, is determined. In some instances, all or a portion of the sequence of the analyte, or a complement thereof, is determined. In some instances, the determined sequences are used to identify the location of the analyte in the biological sample.

(e) Methods of Measuring Gene Expression

In some embodiments, intracellular gene expression of a nucleic acid of a biological sample can be recorded using the methods as described herein. In some embodiments, the method involves multiple molecular dyes attached to a single probe (e.g., a probe that can hybridize to a target nucleic acid) for increased signal-to-noise ratio. In some embodiments, dual probes containing split fluorescent proteins are used. In some embodiments, Forster resonance energy transfer (FRET) based signal generation is used. In some embodiments, fluorescent quenching can occur when the probe binds to the target nucleic acid to restrict signal. In some embodiments, the probe contains fluorescent nucleotides. Details can be found, e.g., in Wu et al., *Chemical Science* 11.1 (2020): 62-69; Spille and Ulrich, *Journal of Cell Science* 128.20 (2015): 3695-3706, each of which is incorporated by reference in its entirety. In some embodiments, the nucleic acid described herein (e.g., an RNA) can be visualized in vivo. In some embodiments, the nucleic acid described herein (e.g., an RNA) can be visualized in vitro.

In some embodiments, the intracellular gene expression can be recorded optically through the use of in situ hybridization (e.g., fluorescent in situ hybridization (FISH)). The objective of in situ hybridization is to determine the presence or absence of one or more nucleic acid sequences of interest at particular spatial locations in a cell or chromosomal sites. Particular nucleic acid sequences are identified within cells by taking advantage of a property of nucleic acids (i.e., their ability to specifically anneal to each other to form hybrids). This process can be used to hybridize two complementary strands of DNA, one strand of RNA to one strand of DNA, and two complementary strands of RNA. In some instances, strand hybridization occurs between natural and artificial nucleic acids. Thus, in some instances, gene expression detection examines a particular transcript of interest.

In some instances, the transcript is associated with normal physiology. In some instances, the transcript is associated with a pathophysiology (e.g., cancer or aberrant development or other disease state). In some instances, a FISH probe is designed to detect one or more mutations. For example, and without limitation, a FISH probe can be designed to detect a point mutation, a single nucleotide polymorphism, an insertion, a deletion, and/or a translocation. In some instances, the probe is designed to detect one or more exons in an mRNA analyte that is alternatively spliced.

In some instances, the probe is directly labeled with a detectable marker as disclosed herein. In some instances, the detectable marker is a fluorescent, radioactive, chemiluminescent, or colorimetric detectable marker. In some instances, the probe is not directly labeled with a detectable marker. In this instance, a second moiety (e.g., comprising a fluorophore) is associated with the hybridized complementary nucleic acids. In some instances, the second moiety includes a fluorescent, radioactive, chemiluminescent, or colorimetric detectable marker.

After a nucleic acid probe is annealed to complementary sequences in cells or tissue, the hybridized probe is visualized. When one of the two strands is labeled, the annealed hybrids can be detected by various methods, including isotopic and nonisotopic (fluorescent and nonfluorescent) approaches. Additional description is found at e.g., Jensen, *The Anatomical Record* 297.8 (2014): 1349-1353, which is incorporated by reference in its entirety.

In some embodiments, the intracellular gene expression can be assessed optically through the use of fluorescence resonance energy transfer (or Forster resonance energy transfer, FRET). The technique of FRET when applied to optical microscopy, permits determination of the approach between two molecules within a distance (several nanometers (e.g., 10 nm)) sufficiently close for molecular interactions to occur. The mechanism of fluorescence resonance energy transfer involves a donor fluorophore in an excited electronic state, which may transfer its excitation energy to a nearby acceptor fluorophore in a non-radiative fashion through long-range dipole-dipole interactions. For example, nucleotide incorporations can be detected through FRET, as described for example in Levene et al., *Science* (2003), 299, 682-686, Lundquist et al., *Opt. Lett.* (2008), 33, 1026-1028, and Korlach et al., *Proc. Natl. Acad. Sci. USA* (2008), 105, 1176-1181, each of which is incorporated by reference in its entirety.

In some embodiments, the recording step comprises hybridizing a plurality of optically-labelled probes to a target nucleic acid. In some embodiments, the optically-labelled probes comprise an optical label, e.g., a fluorophore. In some embodiments, the optically-labelled probes are fluorescently-labelled probes, e.g., fluorescently labelled peptide nucleic acid (PNA) probes. PNAs are synthetic nucleic acid (e.g., DNA) analogs in which the phosphodiester backbone is replaced by repetitive units of N-(2-aminoethyl) glycine to which the purine and pyrimidine bases are attached via a methyl carbonyl linker. The procedures for PNA synthesis are similar to those employed for peptide synthesis, using standard solid-phase manual or automated synthesis. In some instances, the PNA molecules are labelled with biotin or fluorophores. Thus, in some instances, the PNA molecule disclosed herein includes a detection moiety such as a fluorescent, radioactive, chemiluminescent, or colorimetric detectable marker. In some instances, the PNA molecule is associate with (e.g., conjugated to) a biotin molecule that can be detected using e.g., an avidin or streptavidin pulldown, as disclosed herein. A subsequent generation of PNAs involve modification of the N-(2-aminoethyl) glycine backbone (PNA analogs) or chimeric architecture, like PNA-peptide chimeras or PNA-DNA chimeras developed in order to improve the solubility and the cellular uptake of PNAs or to exhibit new biological properties. The synthetic backbone provides PNA with unique hybridization characteristics. Unlike DNA and RNA, the PNA backbone is not charged. Consequently, there is no electrostatic repulsion when PNAs hybridize to its target nucleic acid sequence, giving a higher stability to the PNA-DNA or PNA-RNA duplexes than the natural homo- or heteroduplexes. This greater stability is reflected by a higher thermal melting temperature (Tm), as compared to the corresponding DNA-DNA or DNA-RNA duplexes. Detailed description can be found, e.g., in Pellestor and Paulasova, *European Journal of Human Genetics*, 12.9 (2004): 694-700, which is incorporated by reference in its entirety.

In some embodiments, the optically-labelled probes (e.g., fluorescently labelled PNA probes) can bind to a target nucleic acid in the biological sample. In some embodiments, the target nucleic acid is a DNA. In some instances, the target DNA has been denatured. In some embodiments, the target nucleic acid is an RNA. In some embodiments, the target nucleic acid is a single-stranded DNA or RNA. In some embodiments, the target nucleic acid is a double-stranded DNA or double-stranded RNA. In some embodiments, the target nucleic acid is a DNA/RNA duplex. In some embodiments, the target nucleic acid is an mRNA, a siRNA, a microRNA, or a derivative thereof.

In some embodiments, the optically-labelled probe (e.g., a fluorescently labelled PNA probe) has at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 nucleic acids.

In some embodiments, the optically-labelled probe (e.g., a fluorescently labelled PNA probe) can be used at a final concentration of at least or about $0.1 \times 10^{-6}$ M, at least or about $0.5 \times 10^{-6}$ M, at least or about $1 \times 10^{-6}$ M, at least or about $2 \times 10^{-6}$ M, at least or about $3 \times 10^{-6}$ M, at least or about $4 \times 10^{-6}$ M, at least or about $5 \times 10^{-6}$ M, at least or about $10 \times 10^{-6}$ M, at least or about $20 \times 10^{-6}$ M, at least or about $50 \times 10^{-6}$ M, at least or about $100 \times 10^{-6}$ M, or higher.

In some embodiments, one or more (e.g., 1, 2, 3, 4, or more) optically-labelled probes can hybridize to different portions of the target nucleic acid. In some embodiments, one or more (e.g., 1, 2, 3, 4, or more) optically-labelled probes are used for the detection of the target nucleic acid with a duplex structure, in which case each probe hybridizes specifically to either the sense or antisense strand of the target nucleic acid.

In some embodiments, the optical label can be directly detectable by itself (e.g., radioisotope labels or fluorescent labels) or, in the case of an enzymatic label, can be indirectly detectable, e.g., by catalyzing chemical alterations of a chemical substrate compound or composition, which chemical substrate compound or composition is directly detectable. Optical labels can be suitable for small scale detection and/or suitable for high-throughput screening. As such, suitable optical labels include, but are not limited to, radioisotopes, fluorophores, chemiluminescent compounds, bioluminescent compounds, and dyes.

The optical label can be qualitatively detected (e.g., optically or spectrally), or it can be quantified. Qualitative detection generally includes a detection method in which the existence or presence of the optical label is confirmed, whereas quantifiable detection generally includes a detection method having a quantifiable (e.g., numerically reportable) value such as an intensity, duration, polarization, and/or other properties.

In some embodiments, the optically-labelled probes comprise one or more optical labels, 1, 2, 3, 4, or more. For example, optical labels can be incorporated during nucleic acid polymerization or amplification (e.g., Cy5®-labelled nucleotides, such as Cy5®-dCTP). Any suitable optical label can be used. In some embodiments, the optical label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine 0-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18(5)), DIDS, Dil (DilC18(3)), DiO (DiOC18 (3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™ Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-

3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As discussed herein, in some embodiments, an optical label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate chemical substrates (e.g., an oxidizing reagent plus a chemiluminescent compound). A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinum esters, luciferins, lucigenins, or acridinium esters.

In some embodiments, temporal formation of specific transcripts can be assessed using the methods described herein. For example, one or more fluorescently labelled PNA probes (e.g., a first probe labelled with a donor fluorophore and a second probe labelled with an acceptor fluorophore) can hybridize to different portions (e.g., two adjacent sequences) of a target transcript. Temporal (e.g., real-time) formation of the target transcript can be recorded by measuring the excitation status of the acceptor fluorophore during an appropriate time period, e.g., by fluorescent time lapse microscopy. The donor and acceptor fluorophores can be any FRET pairs known in the art, as described in Bajar et al., *Sensors* 16.9 (2016): 1488, which is incorporated by reference in its entirety.

In some embodiments, the cellular activity as described above can be measured at the same time or using the same sample as a sample in which gene expression is recorded. In some instances, a cellular activity is associated with one biomarker (e.g., one fluorescent color) and gene expression (e.g., detection of a particular gene) is associated with a second biomarker (e.g., a different fluorescent marker). In some instances, both cellular activity and gene expression can be recorded optically using fluorescence microscopy, fluorescent time lapse microscopy, confocal microscopy, multi-photon microscopy (e.g., two-photon excitation microscopy), total internal reflection microscopy, super-resolution microscopy, or any known microscopy techniques known in the art.

In some embodiments, the cellular activity and gene expression can be recorded simultaneously, e.g., by using one or more optical labels (e.g., fluorophores) to tag the chemical dyes, indicators, or optically-labelled probes, such that the cellular activity and the gene expression can be recorded with minimal cross-interferences.

In some instances, after recording gene expression, the sample is fixed. In some instances, the analytes in the sample can hybridize to a plurality of probes on an array (e.g., substrate) as described herein. In some instances, the polyadenylation (poly(A)) sequence of an mRNA hybridizes to a poly-thymine (poly(T)) sequence of a capture domain on a capture probe. In some instances, the capture probe is extended using the analyte that is specifically bound to the capture domain as a template to generate an extended capture probe. In some instances, the extended capture probe is amplified to produce a plurality of extended capture probes (e.g., a plurality of nucleic acids). In some instances, the plurality of extended capture probes, or libraries created therefrom, is sequenced. In some instances, all or a portion of the sequence of the spatial barcode, or a complement thereof, is determined. In some instances, all or a portion of the sequence of the analyte, or a complement thereof, is determined. In some instances, the determined sequences are used to identify the location of the analyte in the biological sample.

(f) Methods of using the Perfusion Chamber and the Multi-Well Plate

Culturing the Biological Sample

In some embodiments, the methods described herein include culturing the biological sample in the perfusion chamber or the multi-well plate. In some embodiments, the biological sample is cultured in a culture medium to maintain its viability. In some embodiments, the culture medium is replaced at an appropriate interval (e.g., about every 12 hours, about every day, about every 2 days, about every 3 days, about every 4 days, about every 5 days, about every 6 days, or about every week). In some embodiments, the culture medium is replaced manually (e.g., by pipetting) or automatically. In some embodiments, the biological sample is cultured statically. In some embodiments, the biological sample is cultured in a perfusion chamber with inlets and outlets as described herein. In some embodiments, the culture medium is perfused to the perfusion chamber at a constant flow rate. In some embodiments, a culture medium (e.g., a tissue or cell culture medium, saline, artificial cerebral spinal fluid (ACSF)) can be perfused to the perfusion chamber to maintain viability of the biological sample (e.g., a tissue or cell sample).

In some embodiments, the culture medium is oxygenated. In some embodiments, additional nutrients or compounds are supplemented to the culture medium to maintain viability of the biological sample. In some embodiments the culture medium includes the blocking reagent described herein. In some instances, the blocking reagent can prevent molecule (e.g., the test compounds or drugs described herein) or cell (e.g., live cells) adhesion to the capture probes. In some embodiments, the blocking reagent is bovine serum albumin (BSA), serum, gelatin (e.g., fish gelatin), milk (e.g., non-fat dry milk), casein, polyethylene glycol (PEG), polyvinyl alcohol (PVA), or polyvinylpyrrolidone (PVP), biotin blocking reagent, a peroxidase blocking reagent, levamisole, Carnoy's solution, glycine, lysine, sodium borohydride, pontamine sky blue, Sudan Black, trypan blue, FITC blocking agent, acetic acid, and/or oligonucleotides including a complementary sequence to the capture oligos.

In some embodiments, the live tissues or cells are cultured in the perfusion chamber or the multi-well plate described herein and grown under conditions to maintain cell viability. For example, temperatures and $CO_2$ concentrations for growing tissues and cells are well known in the art and the methods disclosed herein practice those conditions to maintain sample viability. In some embodiments, tissue culture incubators are utilized during growth and perfusion of the live tissues or cells, typical conditions to maintain cell viability being, for example, 37° C. and 5% $CO_2$.

In some embodiments, chemical dyes, indicators, or optically-labelled probes as described herein can be added to the culture medium, and perfused to the perfusion chamber (or added to the multi-well plate) to interact with the biological sample. In some embodiments, the chemical dyes, indicators, or optically-labelled probes can be added to the biological sample before placing the biological sample into the perfusion chamber or the multi-well plate. In some embodiments, the chemical dyes, indicators, or optically-labelled probes can be added to the biological sample after placing the biological sample to the perfusion chamber or the multi-well plate. In some embodiments, the chemical dyes, indicators, or optically-labelled probes can be internalized to the cells (e.g., cells from a live tissue section) by electropermeabilization, endocytic internalization, or lipid-based permeabilization, while maintaining cell viability.

In some embodiments, the methods described herein can be used to measure dynamic transcriptional FRET imaging. In some embodiments, the methods described herein can be used for real-time transcript detection during pharmacological treatment.

In some embodiments, the biological sample (e.g., cells from a cell culture) is grown or cultured on a substrate (or a surface) within a perfusion chamber or a well of a multi-well plate. In some embodiments, the capture probes described herein are directly printed on the substrate (or the surface). In some embodiments, the existence of capture probes on the substrate (or the surface) does not affect growth of the biological sample. In some embodiments, growth or culturing of the biological sample on the substrate with attached capture probes does not affect data quality of the spatial analysis, e.g., spatial UMI and gene plots; sequencing saturation; median genes per cells; median counts per cell; or median UMIs per cell.

(ii) Live Cell Labelling

In some embodiments, the methods described herein comprise labelling a plurality of live cells of the biological sample. In some embodiments, the live cells are labelled by staining. In some embodiments, the live cells are stained by immunofluorescence (IF). In some embodiments, the live cells are stained intracellularly (e.g., by staining a subcellular organelle including endoplasmic reticulum (ER), Golgi, lysosome, mitochondria, and/or nucleus). In some embodiments, the live cells are stained extracellularly (e.g., plasma membrane staining).

In some embodiments, the live cells are labelled by a fluorescently labelled antibody or antibody fragments thereof. In some embodiments, the live cells are labelled by the chemical dyes, indicators, or optically-labelled probes described herein. In some embodiments, the live cells are labelled by fluorescent reporters (e.g., the live cells are transfected to include a reporter gene). In some embodiments, the stained live cells are detected (e.g., recorded) by time-lapse fluorescence microscopy.

In some embodiments, the live cells are treated with proteinase K and/or trypsin. For example, the treatment can facilitate entry (e.g., by absorption or endocytosis) of the fluorescently labelled antibody or fragments thereof.

(iii) Blocking Probes

In some embodiments, capture probes are blocked prior to contacting the biological sample with the substrate. In some embodiments, capture domains of the capture probes are blocked by blocking probes. In some instances, the capture probes are blocked to prevent molecule (e.g., the test compounds or drugs described herein) or cell (e.g., live cells) adhesion.

In some embodiments, the blocking probe is used to block or modify the free 3' end of the capture domain. In some embodiments, blocking probes can be hybridized to the capture probes to mask the free 3' end of the capture domain, e.g., hairpin probes, partially double stranded probes, or complementary sequences. In some embodiments, the free 3' end of the capture domain can be blocked by chemical modification, e.g., addition of an azidomethyl group as a chemically reversible capping moiety such that the capture probes do not include a free 3' end. Blocking or modifying the capture probes, particularly at the free 3' end of the capture domain, prior to contacting the biological sample with the substrate, prevents modification of the capture probes, e.g., prevents the addition of a poly(A) tail to the free 3' end of the capture probes. In some embodiments, blocking the capture domain reduces non-specific background staining. In some embodiments, the blocking probes are reversible, such that the blocking probes can be removed from the capture domains during or after the time that the capture domains are in contact with the biological sample. In some embodiments, the blocking probe can be removing with RNAse treatment (e.g., RNAse H treatment).

(iv) Fixation

In some embodiments, the biological sample (e.g., a live tissue sample or cell sample) can be fixed in any of a variety of fixatives to preserve the biological structure of the sample prior to analysis. For example, a sample can be fixed via immersion in ethanol, methanol, acetone, formaldehyde (e.g., 2% formaldehyde), paraformaldehyde-Triton, glutaraldehyde, or combinations thereof. In some instances, the biological sample is fixed after recording cellular activity. In some instances, the biological sample is fixed after recording gene expression. In some instances, the biological sample is fixed after recording cellular activity and gene expression. In some embodiments, after fixation, the perfusion chamber can be disassembled such that the substrate (e.g., a spatial array) can be subjected to the spatial analysis as described herein. In some embodiments, the multi-well plate is directly subjected to the spatial analysis, or the individual substrate (e.g., one or more coverslips) can be transferred to a proper platform (e.g., a slide), either manually or automatically, for the spatial analysis. In some embodiments, the biological sample can be fixed during the recording step, followed by the spatial analysis as described herein. In some embodiments, two or more fractions of the biological sample, located in separate perfusion chambers, can be fixed at different time points during the recording step.

In some embodiments, the biological sample is fixed during test compound (e.g. drug) treatment. For example, two or more fractions of the biological sample, each located in separate perfusion chambers (or multi-well plates), can be fixed at different time points during test compound (e.g., drug) treatment. In some embodiments, the biological sample is fixed after test compound (e.g., drug) treatment, then subjected to the spatial analysis as described herein. In some embodiments, one or more steps (e.g., extension of capture probes by reverse transcription) of the spatial analysis are carried out directly in the multi-well plate. For example, the multiple-well plate described herein can be custom made (e.g., heat-resistant), thereby to be compatible with the spatial analysis steps.

(g) Methods for test compound treatment or drug screening

In some embodiments, the methods described herein comprise perfusing one or more (e.g., 1, 2, 3, 4, 5, 6, 7, 8, 9, 10, or more) test compounds through the perfusion chamber. In some embodiments, the test compounds comprises one or more drugs. In some embodiments, one or more test compounds can be perfused through the perfusion chamber, before recording the cellular activity or gene expression as described herein. In some embodiments, one or more test compounds can be perfused through the perfusion chamber, at substantially the same time (e.g., simultaneously) of recording the cellular activity or gene expression as described herein. In some embodiments, the perfusion and recording are automatically performed for high-throughput screening of test compounds (e.g., drugs). In some embodiments, real-time cellular activity or gene expression changes are recorded immediately following perfusion of the test compounds. In some embodiments, culture medium (e.g., without any test compounds) is perfused to remove a test compound from the perfusion chamber, followed by perfusion of the same or a different test compound.

In some embodiments, the methods described herein comprise treating a biological sample with one or more (e.g., 1, 2, 3, 4, 5, 6, 7, 8, 9, 10, or more) test compounds within a multi-well plate or a chambered substrate. In some embodiments, the test compounds comprises one or more drugs. In some embodiments, the test compounds are added to the multi-well plate or chambered substrate manually (e.g., by pipetting) or automatically. In some embodiments, one or more test compounds are added to the multi-well plate or chambered substrate before recording the cellular activity or gene expression as described herein. In some embodiments, one or more test compounds are added to the multi-well plate or chambered substrate at substantially the same time (e.g., simultaneously) of recording the cellular activity or gene expression as described herein. In some embodiments, the test compound treatment and/or the recording of the cellular activity or gene expression are automatically performed for high-throughput screening of test compounds (e.g., drugs). In some embodiments, real-time cellular activity or gene expression changes are recorded immediately following treatment of the test compounds. In some embodiments, a test compound is removed (e.g., by pipetting), followed by addition of the same or a different test compound.

In some embodiments, the test compounds are pre-mixed and perfused to the perfusion chamber (or added to the multi-well plate) at the same time. In some embodiments, the test compounds are sequentially perfused or added. In some embodiments, one or more test compounds are perfused (or added) repeatedly to induce a cellular activity or gene expression change. In some embodiments, the biological sample is treated with one or more test compounds (e.g., drugs) at substantially the same time. In some embodiments, the biological sample is treated with one or more test compounds (e.g., drugs) at different times.

In some embodiments, the test compound (e.g., a drug) can be an agonist. In some embodiments, the test compound (e.g., a drug) can be an antagonist. In some embodiments, the test compound can be a drug, e.g., a small-molecule drug, an antibody or antigen-binding fragment thereof, a pharmacological agent, or any test compounds of interest. In some embodiments, the test compound (e.g., a drug) activates or stimulates one or more cellular activities. In some embodiments, the test compound (e.g., a drug) inhibits one or more cellular activities. In some embodiments, the test compound (e.g., a drug) increases intracellular gene expression of a nucleic acid. In some embodiments, the test compound (e.g., a drug) decreases intracellular gene expression of a nucleic acid. In some embodiments, the test compound (e.g., a drug) decreases the viability and thus gene expression or other cellular activity within a cell or tissue.

In some embodiments, the test compound is an anti-cancer drug. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. Cancers described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the test compounds described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the test compound is an antibody or antigen-binding fragment thereof, e.g., Muromonab-CD3, Efalizumab, Tositumomab-I131, Nebacumab, Edrecolomab, Catumaxomab, Daclizumab, Abciximab, Rituximab, Basiliximab, Palivizumab, Infliximab, Trastuzumab, Adalimumab, Ibritumomab tiuxetan, Omalizumab, Cetuximab, Bevacizumab, Natalizumab, Panitumumab, Ranibizumab, Eculizumab, Certolizumab pegol, Ustekinumab, Canakinumab, Golimumab, Ofatumumab, Tocilizumab, Denosumab, Belimumab, Ipilimumab, Brentuximab vedotin, Pertuzumab, Ado-trastuzumab emtansine, Raxibacumab, Obinutuzumab, Siltuximab, Ramucirumab, Vedolizumab, Nivolumab, Pembrolizumab, Blinatumomab, Alemtuzumab, Evolocumab, Idarucizumab, Necitumumab, Dinutuximab, Secukinumab, Mepolizumab, Alirocumab, Daratumumab, Elotuzumab, Ixekizumab, Reslizumab, Olaratumab, Bezlotoxumab, Atezolizumab, Obiltoxaximab, Brodalumab, Dupilumab, Inotuzumab ozogamicin, Guselkumab, Sarilumab, Avelumab, Emicizumab, Ocrelizumab, Benralizumab, Durvalumab, Gemtuzumab ozogamicin, Erenumab, erenumab-aooe, Galcanezumab, galcanezumab-gnlm, Burosumab, burosumab-twza, Lanadelumab, lanadelumab-flyo, Mogamulizumab, mogamulizumab-kpkc, Tildrakizumab; tildrakizumab-asmn, Fremanezumab, fremanezumab-vfrm, Ravulizumab, ravulizumab-cwvz, Cemiplimab, cemiplimab-rwlc, Ibalizumab, ibalizumab-uiyk, Emapalumab, emapalumab-lzsg, Moxetumomab pasudotox, moxetumomab pasudotox-tdfk, Caplacizumab, caplacizumab-yhdp, Risankizumab, risankizumab-rzaa, Polatuzumab vedotin, polatuzumab vedotin-piiq, Romosozumab, romosozumab-aqqg, "Brolucizumab, brolucizumab-dbll", Crizanlizumab; crizanlizumab-tmca, Enfortumab vedotin, enfortumab vedotin-ejfv, [fam-]trastuzumab deruxtecan, fam-trastuzumab deruxtecan-nxki, Teprotumumab, teprotumumab-trbw, Eptinezumab, eptinezumab-jjmr, Isatuximab, isatuximab-irfc, Sacituzumab govitecan; sacituzumab govitecan-hziy, Inebilizumab, inebilizumab-cdon, "Tafasitamab, tafasitamab-cxix", Belantamab mafodotin, belantamab mafodotin-blmf, Satralizumab, satralizumab-mwge, Atoltivimab, maftivimab, and odesivimab-ebgn, Naxitamab-gqgk, Margetuximab-cmkb, Ansuvimab-zykl, Evinacumab, Dostarlimab, dostarlimab-gxly, Loncastuximab tesirine, loncastuximab tesirine-lpyl, Tanezumab, Aducanumab, Tralokinumab, Teplizumab, Narsoplimab, Retifanlimab, Oportuzumab monatox, Anifrolumab, Inolimomb, Bimekizumab, Balstilimab, Sutimlimab (BIVV009), Ublituximab, Amivantamab, Tisotumab vedotin, Toripalimab, Omburtamab, or Balstilimab. In some embodiments, the antibody or antigen-binding fragment thereof is a multi-specific antibody (e.g., a bispecific antibody). In some embodiments, the antibody or antigen-binding fragment thereof is a single-chain variable fragment (scFv). In some embodiments, the antibody or antigen-binding fragment thereof is part of a chimeric antigen receptor (CAR).

In some embodiments, the test compound is a small molecule drug. In some embodiments, the small molecule drug is designed for treating cancer. For example, the molecular target of the small molecule drug can be selected from tyrosine & serine/threonine kinases (e.g., Imanitib, Gefitinib, Erlotinib, Sunitinib, Lapatinib, Nilotinib, Sorafenib, Temsirolimus, Everolimus, Pazopanib, Crizotinib, Ruxolitinib, Axitinib, Bosutinib, Cabozantinib, Ponatinib, Regorafenib, Ibrutinib, Trametinib, and Perifosine); proteasomes (e.g., Bortezomib and Carfilzomib); matrix metalloproteinases and heat shock proteins (e.g., Batimastat, Ganetespib, and NVP-AUY922); and apoptosis (e.g., Obatoclax and Navitoclax). In some embodiments, the small molecule drug is selected from Afatinib, Axitinib, Bosutinib, Cabozantinib, Certinib, Crizotinib, Dasatinib, Erlotinib, Gefitinib, Ibrutinib, Imatinib, Lapatinib, Linsitinib, Lenvatinib, Osimertinib, Pazopanib, Ponatinib, Regorafenib, Rucaparib, Ruxolitinib, Sunitinib, and Vandetanib. Details can be found, e.g., in Pathak, Akshat, et al. *Vivechan International Journal of Research* 9.1 (2018): 36, which is incorporated herein by reference in its entirety.

In some embodiments, the small molecule drug is used for treating breast cancer, e.g., Ribociclib (Kisqali), Alpelisib (Piqray), Abemaciclib (Verzenio), Talazoparib (Telzenna), Nertinib (Nerlynx), Palbociclib (Ibrance), Ixabepilone (Ixempra), Anastrazole (Arimidex), Lapatinib (Tykerb), Toremifene (Fareston), Letrozole (Femara), Raloxifene (Evista), Tamoxifen Oral Liquid (Soltamax), Exemestane (Aromasin), Testosterone Cypionate (Depo-Testosterone), Fluoxymesterone (Halotestine/Androxy), Fadrozole (Afema), Tamibarotene (Amnolake), and Testosterone Propionate. In some embodiments, the small molecule drug is used for treating leukemia cancer, e.g., Gilteritinib (Xospata), Venetoclax (Venclexta), Bosutinib (Bosulif), Nilotinib (Tasigna), Tretinoin (Vesanoid), Clofarabine (Clolar), Cytarabine/Daunorubicin (Vyxeos), Dasatinib (Sprycel), Ponatinib (Iclusig), Enasidenib (Idhifa), Ivosidenib (Tibsovo), Cladribine (Mavenclad/Leustatin), Mercaptupurine Oral Suspension (Purixan), Methotrexate Oral Solution (Xatmep), Pentostatin (Nipent), Arsenic Trioxide (Trisenox), Quizartinib (Vanflyta), Histamine Dihydrochloride Injection (Ceplene), Ubenimix (Bestatin), Omacetaxine Mepesuccinate (Synribo), and Radotinib (Supect). In some embodiments, the small molecule drug is used for treating lung cancer, e.g., Gefitinib (Irresa), Entrectinib (Rozlytrek), Osimertinib (Tagrisso), Erlotinib (Tarceva), Brigatinib (Alunbirg), Lorbrena (Lorlatinib), Vinorelbine (Navelbine), Zykadia (Certinib), Pemetrexed (Alimta), Alectinib (Alecensa), Xalkori (Crizotinib), Nintedanib (Ofev), Anlotinib (Focus V), Amrubicin (Calsed), and Icotinib (Conmana). In some embodiments, the small molecule drug is used for treating lymphomas, e.g., Copanlisib (Aliqopa), Methoxsalen Solution (Uvadex), Pralatrexate (Folotyn), Bexarotene Topical (Targretin Gel), Pixantrone (Pixuvri), Belinostat (Beleodaq), Zanubrutinib (Brukinsa), Vorinostat (Zolinza), Romidepsin (Istodax), Bexarotene (Targretin), and Mechlorethamine (Valchlor/Ledaga). In some embodiments, the small molecule drug is used for treating myeloma, e.g., Ixazomib (Ninlaro), Melphalan Intravenous (Evomela/Chemostat), Thalidomide (Thalomid), Selinexor (Xpovio), Panobinostat (Farydak), Bortezomib (Velcade), Pomalidomide (Pomalyst), and Dexamethasone High Dose (Neofordex).

In some embodiments, the small molecule drug is used for treating prostate cancer, e.g., Xtandi (Enzalutamide), Apalutamide (Erleada), Ertafitinib (Balversa), Darolutamide (Nubeqa), Bicalutamide (Casodex), Nilutamide (Nilandron), Abiraterone (Zytiga), Xofigo (Radium Ra 223 dichloride), and Pedeliporfin (Tookad). In some embodiments, the small molecule drug is used for treating gastric cancer, e.g., Avapritinib (Ayvakit), Rivoceranib (Aitan), Gimeracil/Oteracil/Tegafur (Teysuno/TS-1), and Eptaplatin/Heptaplatin. In some embodiments, the small molecular drug is used for treating cancer diagnosis, e.g., Fluciclovine 18F (Axumin), Tc 99m Tilmanocept (Lymphoseek), Perflubutane (Sonazoid), Hexyl Aminolevulinate (Cysview), Fluorocholine 18F (IASOcholine/Pcolina), and Gadobuterol (Gadavist). In some embodiments, the small molecule drug is used for treating skin cancer, e.g., Benimetinib (Mektovi), Cobimetinib (Cotellic), Sonidegib (Odomzo), Vismodegib (Erivedge), Imiquimod (Aldara/Zyclara), Amivolevulinic Acid (Ameluz), Methyl Aminolevulinate (Metvixia/Metvix PDT), and Vemurafenib (Zelboraf). In some embodiments, the small molecule drug is used for treating pancreatic cancer, e.g., Irinotecan Liposome Injection (Onivyde). In some embodiments, the small molecule drug is used for treating thyroid tumors, e.g., Vendetanib (Caprelsa). In some embodiments, the small molecule drug is used for treating renal cancer, e.g., Axitinib (Inlyta). In some embodiments, the small molecule drug is used for treating colorectal cancer, e.g., Tipiracil/Trifluridine (Lonsurf), Irinotecan (Camptosar), Oxaliplatin (Eloxatin), Raltitrexed (Tomudex), Irinotecan-Eluting Beads (Paragon Beads/Debiri), and Fruquintinib (Elunate). In some embodiments, the small molecule drug is used for treating solid tumors, e.g., Larotectinib (Viktravi). In some embodiments, the small molecule drug targets multiple cancers, e.g., Fludarabin (Fludara/Oforta), Gemcitabine (Gemzar), Sorafnib (Nexavar), Rucaparib (Rubraca), Doxorubicin (Aridamycin), Acalabrutinib (Calquence), Ibrutinib (Imbruvica), Azacitidine (Vidaza), Lenalidomide (Revlimid), Doxorubicin Liposomal (Doxil), Tazemetostat (Tazverik), Busulfan (Busulfex), Afatinib (Gilotrif), Gemcitabine (Infugem), Carmustine Polifeprosan 20 wafer (Gliadel), Eribulin (Halaven), Paclitaxel-Protein Bound (Abraxane), Trabectedine (Yondelis), Paclitaxel (Taxol), Docetaxel (Taxotere), Idelalisib (Zydelig), Duvelisib (Copiktra), Regorafenib (Stivagra), Nelarabine (Arranon), Capecitabine (Xeloda), Lenvatinib (Lenvima), Olaparib (Lynparza), Niraparib (Zejula), Pazopanib (Votrient), Alitretinoin Topical (Panretin), Mitotane (Lysodren), Valrubicin (Valstar), Hydroxyurea (Hydrea), Mitoxantrone (Novantrone), Zoledronic Acid (Zometa/Reclast), Fotemustine (Muforan), Paclitaxel Nanoparticle (Nanoxel), Topotecan (Hycamtin), Decitabine (Decogen), Tivozanib (Fotivda), Telotristat Etiprate (Xermelo), Imatinib (Gleevec), Trametinib (Mekinist), Cabozantinib (Cabometyx), Encorafenib (Braftovi), Dabrafenib (Tafinlar), Sunintab (Sutent), Levoleucovorin (Fusilev/Khapzory), Bendamustine (Treanda/Belrapzo/Bendeka), Forodesine (Fodosine/Mundesine), Talaporfin (Laserphyrin), Tucidinostat (Epidaza), Doxorubicin Eluting Beads (DC Beads), Temozolomide (Temodar), Paclitaxel Polymeric Micelle Formulation (GenexolPM), Docetaxel polymeric micelle (Nanoxel M), Methotrexate, Treosulfan (Ovastat/Tercondi), Belotecan (Camtobell), Paclitaxel Liposomal(Lipusu/Bevetex), Amsacrine (Amsa PD/Amekrin), Cyclophosphamide, Docetaxel Nanosome (DoceAqualip), Pamidronic acid (Aredia), Mopidamol (Rapenton), Nedaplatin (Aqupla), Cytarabin/Cytarabin Liposomal (DepoCyt), and Dianhydrogalactitol (DAG for Injection).

In some embodiments, the anti-cancer drug is a chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate.

In some embodiments, the test compound is an anti-viral drug, e.g., Acyclovir, Brivudin, Cidofovir, Famciclovir, Fomivirsen, Foscarnet, Ganciclovir, Penciclovir, Valacyclovir, Valganciclovir, Vidarabine, Amantadine, Rimantadine, Oseltamivir, Zanamivir, Interferons, Ribavirin, Adefovir, Emtricitabine, Entecavir, Lamivudine, Telbivudine, Tenofovir, Boceprevir, or Telaprevir. Details of anti-viral drugs can be found, e.g., in Razonable, R. R. *Mayo Clinic Proceedings*. Vol. 86. No. 10. Elsevier, 2011; De Clercq, E., et al., *Clinical Microbiology Reviews* 29.3 (2016): 695-747; and De Clercq, E. *Annual Review of Pharmacology and Toxicology* 51 (2011): 1-24; each of which is incorporated herein by reference in its entirety.

While not intending to be bound by any theory, it is believed that the test compound described herein can be any molecule having desired functions (e.g., anti-cancer functions) or functions to be determined. In some embodiments, when the test compound is applied to a biological sample, the cellular activity (e.g., any of the cellular activities described herein) and/or gene expression (e.g., any of the gene expression detections described herein) of the biological sample are changed.

Also included herein are methods for screening test compounds, e.g., polypeptides, polynucleotides, inorganic or organic large or small molecule test compounds, to identify agents useful in the treatment of disorders or diseases.

As used herein, "small molecules" refer to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, *Pergamon-Elsevier Science Limited* (1998), and include those such as the "split and pool" or "parallel" synthesis techniques, solid-phase and solution-phase techniques, and encoding techniques (See, for example, Czarnik, *Curr. Opin. Chem. Bio.* 1:60-6 (1997)). In addition, a number of small molecule libraries are commercially available. A number of suitable small molecule test compounds are listed in U.S. Pat. No. 6,503,713, which is incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample, e.g., a cell or living tissue, and one or more effects of the test compound is evaluated.

In some embodiments, the test sample is, or is derived from (e.g., a sample taken from) an in vivo model of a disorder as described herein. For example, an animal model, e.g., a rodent such as a rat, can be used.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern Genetic Analysis*, 1999, W. H. Freeman and Company; Ekins and Chu, *Trends in Biotechnology*, 1999, 17:217-218; MacBeath and Schreiber, *Science* 2000, 289(5485):1760-1763; Simpson, *Proteins and Proteomics: A Laboratory Manual*, Cold Spring Harbor Laboratory Press; 2002; Hardiman, Microarrays *Methods and Applications: Nuts & Bolts*, DNA Press, 2003).

A test compound that has been screened by a method described herein and determined to be effective, can be considered a candidate compound. A candidate compound that has been screened, e.g., in an in vivo model of a disorder, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that activate or inhibit one or more cellular activities; alternatively, test compounds that increase or decrease intracellular gene expression of a nucleic acid) in a first screen can be selected and systematically altered, e.g., using rational design, to optimize binding affinity, avidity, specificity, or other parameters. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating disorders or diseases described herein. A variety of techniques useful for determining the structures of "hits" can be used in the methods described herein, e.g., NMR, mass spectrometry, gas chromatography equipped with electron capture detectors, fluorescence and absorption spectroscopy. Thus, the disclosure also includes compounds identified as "hits" by the methods described herein, and methods for their administration and use in the treatment, prevention, or delay of development or progression of a disorder described herein.

Test compounds identified as candidate therapeutic compounds can be further screened by administration to a subject (e.g., an animal model) of a disorder or disease as described herein. The animal can be monitored for a change in the disorder, e.g., for an improvement in a parameter of the disorder, e.g., a parameter related to clinical outcome. In some embodiments, the subject is a human.

In some embodiments, the methods described herein can be used to examine real-time pharmacological and/or stimulus-dependent response of the biological sample. In some embodiments, the methods described herein can examine the pharmacological impact on gene expression. In some embodiments, the methods described herein can be used in conjunction with activity-based fluorescent reporters (e.g., calcium probes and voltage-gated probes).

In some embodiments, the biological sample described herein is treated with one or more test compounds (e.g., drugs) before recording the cellular activity and/or the intracellular gene expression as described herein. In some embodiments, the biological sample described herein is treated with one or more test compounds (e.g., drugs) at substantially the same time as recording the cellular activity and/or the intracellular gene expression as described herein.

In some embodiments, the test compound is conjugated with a fluorophore. In some embodiments, the test compound is conjugated with an oligonucleotide. In some embodiments, the oligonucleotide comprises a sequence that uniquely identifies the test compound. In some instances, the biological sample can be treated with two or more test compounds, and each test compound is conjugated with a barcode sequence that uniquely identifies the test compound. Details can be found, e.g., in U.S. Patent Application No. 62/963,897, which is incorporated herein by reference in its entirety.

In some embodiments, the temporal measurement results (e.g., the cellular activity or gene expression recordings) can be combined with the spatial gene expression analysis results to provide spatio-temporal insights in the biological sample (e.g., in response to drug treatment). In some embodiments, the spatio-temporal insights provide comprehensive assessment of drug effects.

(h) Diffusion-Resistant Media/Lids

To increase efficiency by encouraging analyte diffusion toward the spatially-barcoded capture probes, a diffusion-resistant medium can be used. In general, molecular diffusion of biological analytes can occur in all directions, including toward the capture probes (i.e., toward the spatially-barcoded array), and away from the capture probes (i.e., into the bulk solution). Increasing analyte migration toward the spatially-barcoded array reduces analyte diffusion away from the spatially-barcoded array and increases the capturing efficiency of the capture probes, thereby increasing resolution of the spatial array.

In some embodiments, a diffusion-resistant medium is placed on top of a biological sample (e.g., the live tissue sample or cell sample described herein) that is placed or cultured on top of a spatially-barcoded substrate. For example, the diffusion-resistant medium can be placed onto an array that a biological sample has been cultured on top. In some embodiments, the diffusion-resistant medium and spatially-barcoded array are the same component. For example, the diffusion-resistant medium can contain spatially-barcoded capture probes within or on the diffusion-resistant medium (e.g., coverslip, slide, hydrogel, or membrane). In some embodiments, a biological sample is placed or cultured on a substrate and a diffusion-resistant medium is placed on top of the biological sample. Additionally, a spatially-barcoded capture probe array can be placed in close proximity over a diffusion-resistant medium. For example, a diffusion-resistant medium may be sandwiched between a spatially-barcoded array and a biological sample on a substrate. In some embodiments, a diffusion-resistant medium is disposed or spotted onto a biological sample. In other embodiments, a diffusion-resistant medium is placed in close proximity to a biological sample.

In general, a diffusion-resistant medium can be any material known to limit diffusivity of biological analytes. For example, a diffusion-resistant medium can be a solid lid (e.g., coverslip or glass slide). In some embodiments, a diffusion-resistant medium may be made of glass, silicon, paper, hydrogel polymer monoliths, or other material. In some embodiments, the glass slide can be an acrylated glass slide. In some embodiments, the diffusion-resistant medium is a porous membrane. In some embodiments, the material may be naturally porous. In some embodiments, the material may have pores or wells etched into solid material. In some embodiments, the pore volume can be manipulated to minimize loss of target analytes. In some embodiments, the membrane chemistry can be manipulated to minimize loss of target analytes. In some embodiments, the diffusion-resistant medium (e.g., hydrogel) is attached to a substrate (e.g., glass slide), for example by covalent or non-covalent means. In some embodiments, a diffusion-resistant medium can be any material known to limit diffusivity of poly(A) transcripts. In some embodiments, a diffusion-resistant medium can be any material known to limit the diffusivity of proteins. In some embodiments, a diffusion-resistant medium can be any material know to limit the diffusivity of macromolecular constituents.

In some embodiments, a diffusion-resistant medium includes one or more diffusion-resistant media. For example, one or more diffusion-resistant media can be combined in a variety of ways prior to placing the media in contact with a biological sample including, without limitation, coating, layering, or spotting. As another example, a hydrogel can be placed onto a biological sample followed by placement of a lid (e.g., glass slide) on top of the hydrogel.

In some embodiments, a force (e.g., hydrodynamic pressure, ultrasonic vibration, solute contrasts, microwave radiation, vascular circulation, or other electrical, mechanical, magnetic, centrifugal, and/or thermal forces) is applied to control diffusion and enhance analyte capture. In some embodiments, one or more forces and one or more diffusion-resistant media are used to control diffusion and enhance capture. For example, a centrifugal force and a glass slide can used contemporaneously. Any of a variety of combinations of a force and a diffusion-resistant medium can be used to control or mitigate diffusion and enhance analyte capture.

In some embodiments, a diffusion-resistant medium, along with the spatially-barcoded array and biological sample, is submerged in a bulk solution. In some embodiments, a bulk solution includes permeabilization reagents. In some embodiments, a diffusion-resistant medium includes at least one permeabilization reagent. In some embodiments, a diffusion-resistant medium (i.e. hydrogel) is soaked in permeabilization reagents before contacting the diffusion-resistant medium to the sample. In some embodiments, a diffusion-resistant medium can include wells (e.g., micro-, nano-, or picowells) containing a permeabilization buffer or reagents. In some embodiments, a diffusion-resistant medium can include permeabilization reagents. In some embodiments, a diffusion-resistant medium can contain dried reagents or monomers to deliver permeabilization reagents when the diffusion-resistant medium is applied to a biological sample. In some embodiments, a diffusion-resistant medium is added to the spatially-barcoded array and sample assembly before the assembly is submerged in a bulk solution. In some embodiments, a diffusion-resistant medium is added to the spatially-barcoded array and sample assembly after the sample has been exposed to permeabilization reagents. In some embodiments, permeabilization reagents are flowed through a microfluidic chamber or channel over the diffusion-resistant medium. In some embodiments, the flow controls the sample's access to the permeabilization reagents. In some embodiments, target analytes diffuse out of the sample and toward a bulk solution and get embedded in a spatially-barcoded capture probe-embedded diffusion-resistant medium. In some embodiments, a free solution is sandwiched between the biological sample and a diffusion-resistant medium.

Figure 7:
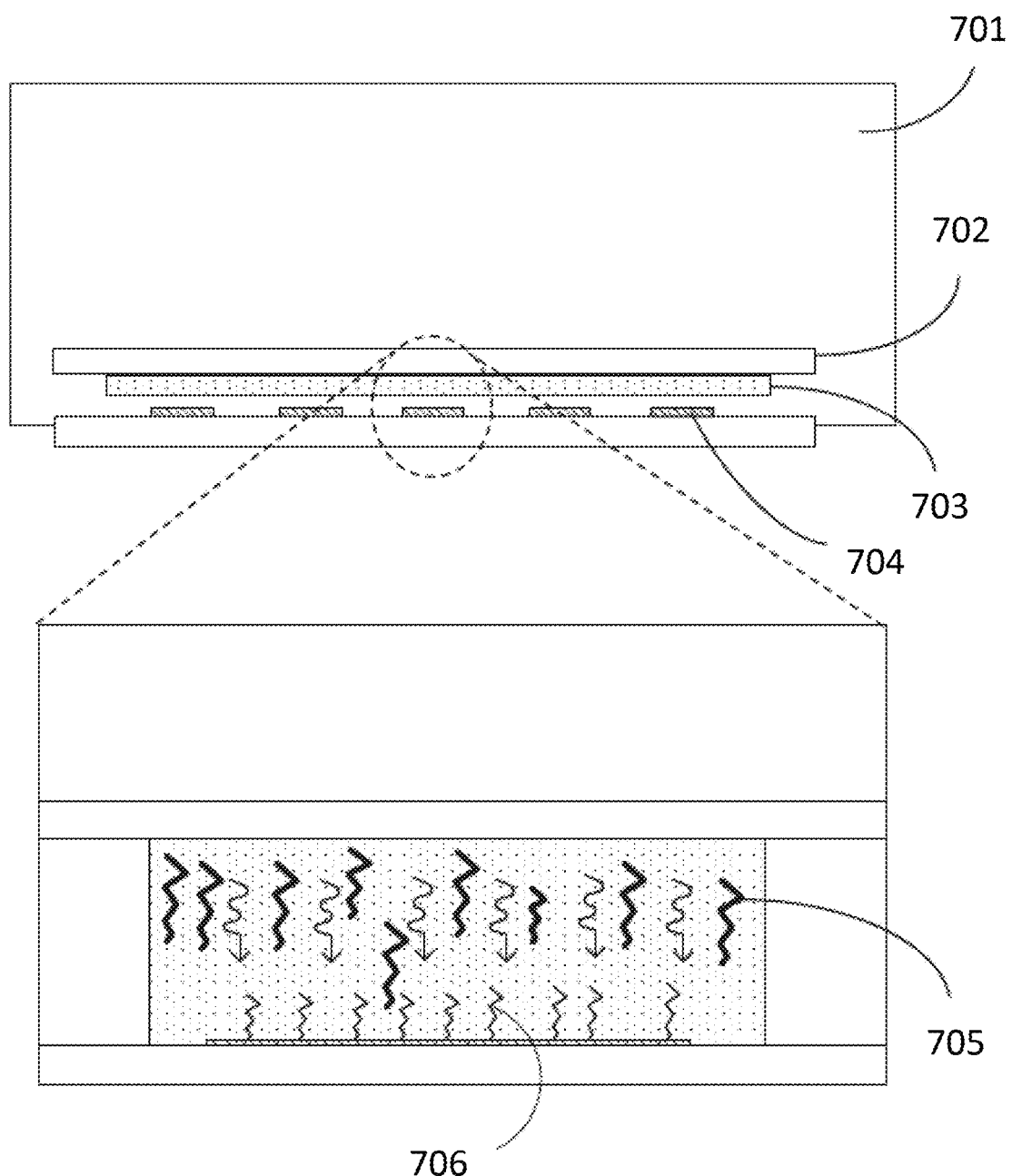
FIG. 7 is a schematic illustrating a side view of a diffusion-resistant medium.

FIG. 7 is an illustration of an exemplary use of a diffusion-resistant medium. A diffusion-resistant medium/lid 702 can be contacted with a sample 703. In FIG. 7, a glass slide 704 is populated with spatially-barcoded capture probes 706, and the sample 703, is contacted with the array 704 and spatially-barcoded capture probes 706. A diffusion-resistant medium/lid 702 can be applied to the sample 703, wherein the sample 703 is sandwiched between a diffusion-resistant medium 702 and a capture probe coated slide 704. When a permeabilization solution 701 is applied to the sample, using the diffusion-resistant medium/lid 702 directs migration of the analytes 705 toward the capture probes 706 by reducing diffusion of the analytes out into the medium. Alternatively, the diffusion resistant medium/lid may contain permeabilization reagents.

(i) Electrophoretic Transfer

In some embodiments, electrophoretic transfer of analytes can be performed while retaining the relative spatial locations of analytes in a biological sample while minimizing passive diffusion of an analyte away from its location in a biological sample. In some embodiments, an analyte captured by a capture probe (e.g., capture probes on a substrate) retains the spatial location of the analyte present in the biological sample from which it was obtained (e.g., the spatial location of the analyte that is captured by a capture probe on a substrate when the analyte is actively migrated to the capture probe by electrophoretic transfer can be more precise or representative of the spatial location of the analyte in the biological sample than when the analyte is not actively migrated to the capture probe). In some embodiments, electrophoretic transport and binding process is described by the Damköhler number (Da), which is a ratio of reaction and mass transport rates. The fraction of analytes bound and the shape of the biological sample will depend on the parameters in the Da. There parameters include electromigration velocity $U_e$ (depending on analyte electrophoretic mobility $\mu_e$ and electric field strength E), density of capture probes (e.g., barcoded oligonucleotides) $p_0$, the binding rate between probes (e.g., barcoded oligonucleotides) and analytes $k_{on}$, and capture area thickness L.

$$Da \sim \frac{k_{on}p_0L}{\mu_e E}$$

Fast migration (e.g., electromigration) can reduce assay time and can minimize molecular diffusion of analytes.

In some embodiments, electrophoretic transfer of analytes can be performed while retaining the relative spatial alignment of the analytes in the sample. As such, an analyte captured by the capture probes (e.g., capture probes on a substrate) retains the spatial information of the cell or the biological sample from which it was obtained. Applying an electrophoretic field to analytes can also result in an increase in temperature (e.g., heat). In some embodiments, the increased temperature (e.g., heat) can facilitate the migration of the analytes towards a capture probe.

In some examples, a spatially-addressable microelectrode array is used for spatially-constrained capture of at least one charged analyte of interest by a capture probe. For example, a spatially-addressable microelectrode array can allow for discrete (e.g., localized) application of an electric field rather than a uniform electric field. The spatially-addressable microelectrode array can be independently addressable. In some embodiments, the electric field can be applied to one or more regions of interest in a biological sample. The electrodes may be adjacent to each other or distant from each other. The microelectrode array can be configured to include a high density of discrete sites having a small area for applying an electric field to promote the migration of charged analyte(s) of interest. For example, electrophoretic capture can be performed on a region of interest using a spatially-addressable microelectrode array.

A high density of discrete sites on a microelectrode array can be used. The surface can include any suitable density of discrete sites (e.g., a density suitable for processing the sample on the conductive substrate in a given amount of time). In one embodiment, the surface has a density of discrete sites greater than or equal to about 500 sites per 1 mm². In some embodiments, the surface has a density of discrete sites of about 100, about 200, about 300, about 400, about 500, about 600, about 700, about 800, about 900, about 1,000, about 2,000, about 3,000, about 4,000, about 5,000, about 6,000, about 7,000, about 8,000, about 9,000, about 10,000, about 20,000, about 40,000, about 60,000, about 80,000, about 100,000, or about 500,000 sites per 1 mm². In some embodiments, the surface has a density of discrete sites of at least about 200, at least about 300, at least about 400, at least about 500, at least about 600, at least about 700, at least about 800, at least about 900, at least about 1,000, at least about 2,000, at least about 3,000, at least about 4,000, at least about 5,000, at least about 6,000, at least about 7,000, at least about 8,000, at least about 9,000, at least about 10,000, at least about 20,000, at least about 40,000, at least about 60,000, at least about 80,000, at least about 100,000, or at least about 500,000 sites per 1 mm².

Figure 8B:
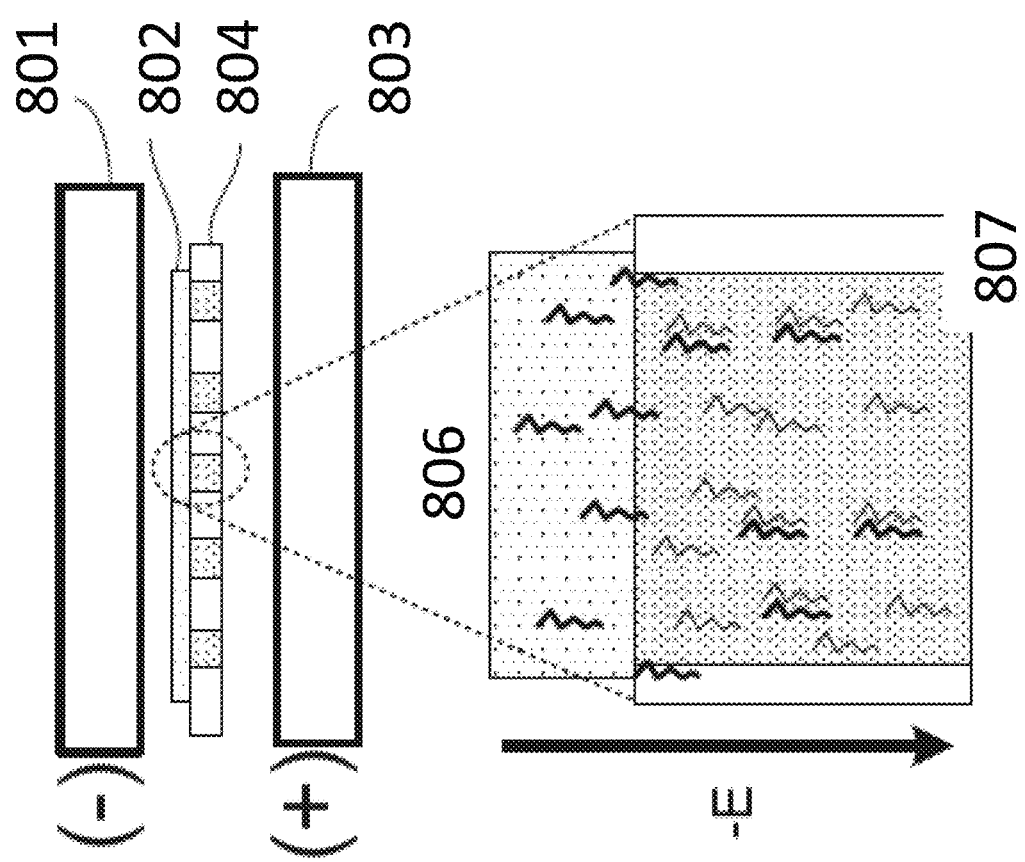

Schematics illustrating an electrophoretic transfer system configured to direct nucleic acid analytes (e.g., mRNA transcripts) toward a spatially-barcoded capture probe array are shown in FIG. 8A and FIG. 8B. In this exemplary configuration of an electrophoretic system, a sample 802 is sandwiched between the cathode 801 and the spatially-barcoded capture probe array 804, 805, and the spatially-barcoded capture probe array 804, 805 is sandwiched between the sample 802 and the anode 803, such that the sample 802, 806 is in contact with the spatially-barcoded capture probes 807. When an electric field is applied to the electrophoretic transfer system, negatively charged nucleic acid analytes 806 will be pulled toward the positively charged anode 803 and into the spatially-barcoded array 804, 805 containing the spatially-barcoded capture probes 807. The spatially-barcoded capture probes 807 interact with the nucleic acid analytes (e.g., mRNA transcripts hybridize to spatially-barcoded nucleic acid capture probes forming DNA/RNA hybrids) 806, making the analyte capture more efficient. The electrophoretic system set-up may change depending on the target analyte. For example, proteins may be positive, negative, neutral, or polar depending on the protein as well as other factors (e.g., isoelectric point, solubility, etc.). The skilled practitioner has the knowledge and experience to arrange the electrophoretic transfer system to facilitate capture of a particular target analyte.

Figures 9A, 9B, 9C, 9D, 9E, 9F, 9G:
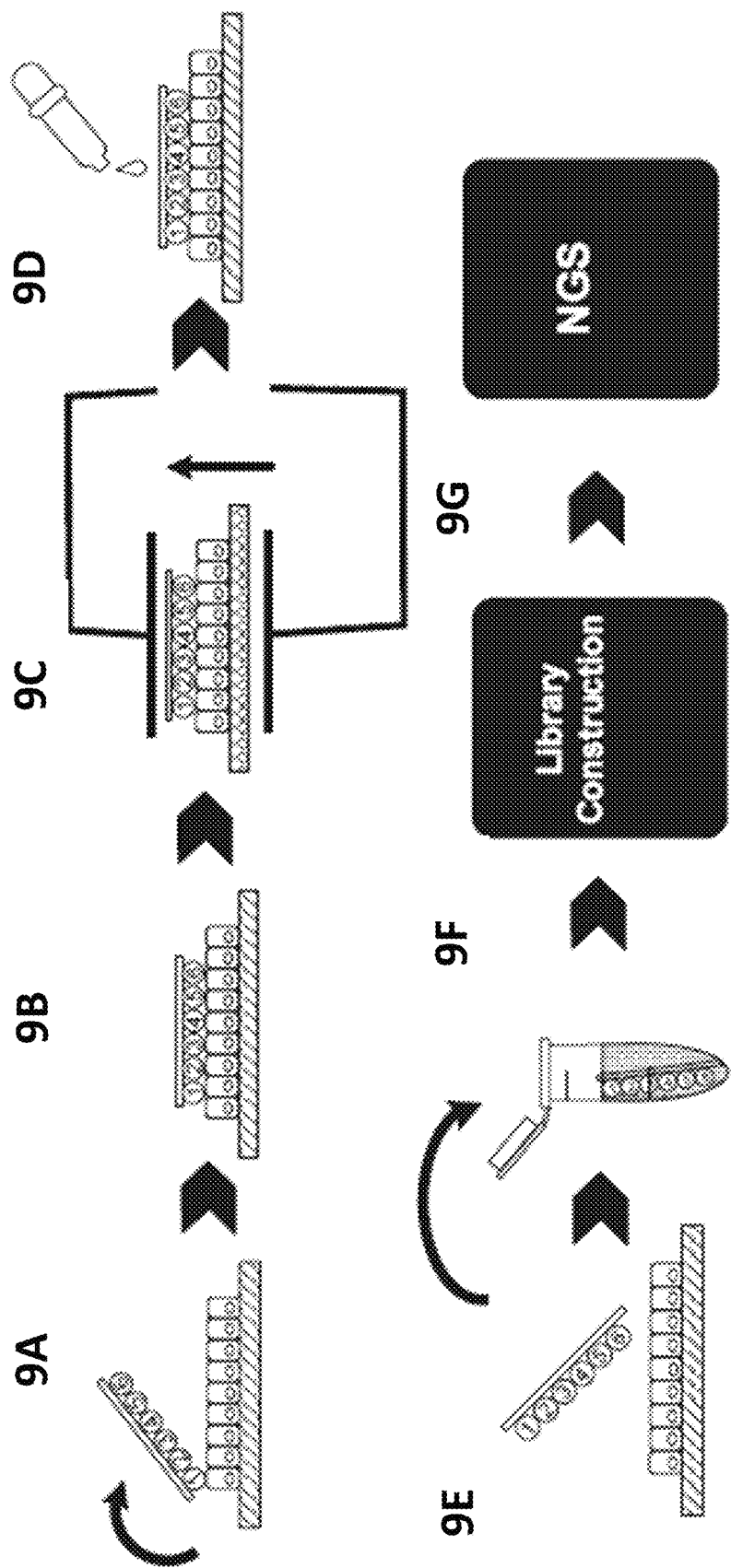
FIGS. 9A-9G show a schematic illustrating an exemplary workflow protocol utilizing an electrophoretic transfer system. NGS: next-generation sequencing.

FIGS. 9A-9G is an illustration showing an exemplary workflow protocol utilizing an electrophoretic transfer system. In the example, FIG. 9A depicts a flexible spatially-barcoded feature array being contacted with a sample. The feature array can be a flexible array, wherein the sample is immobilized on a hydrogel, membrane, or other substrate. FIG. 9B depicts contact of the array with the sample and imaging of the array-sample assembly. The image of the sample/array assembly can be used to verify sample placement, choose a region of interest, or any other reason for imaging a sample on an array as described herein. FIG. 9C depicts application of an electric field using an electrophoretic transfer system to aid in proximal capture of a target analyte by the capture probes on the array. Here, negatively charged mRNA target analytes migrate toward the positively charged anode. FIG. 9D depicts application of reverse transcription reagents and first strand cDNA synthesis of the captured target analytes. FIG. 9E depicts array removal and preparation for library construction (FIG. 9F) and next-generation sequencing (FIG. 9G).

(o) Kits

In some embodiments, also provided herein are kits that include one or more reagents to detect one or more analytes described herein. In some instances, the kit includes a substrate comprising a plurality of capture probes comprising a spatial barcode and the capture domain. In some instances, the kit includes any of the apparatus or components thereof as described herein.

A non-limiting example of a kit used to perform any of the methods described herein includes: a) an array comprising a plurality of capture probes; b) a perfusion chamber defined by mounting a gasket on the array, and a cover mounted on the gasket, wherein the cover includes: (i) an inlet being fluidly connected to a plurality of input channels, and (ii) an outlet being fluidly connected to a plurality of output channels; and c) an instruction for using the kit.

A non-limiting example of a kit used to perform any of the methods described herein includes: a) a multi-well plate comprising a plurality of capture probes, wherein the plurality of capture probes are directly attached (e.g., printed) to a surface of a well of the multi-well plate; and b) an instruction for using the kit. Another non-limiting example of a kit used to perform any of the methods described herein includes: a) a coverslip comprising a plurality of capture probes; b) a multi-well plate, wherein the coverslip is attached to a surface of a well of the multi-well plate; and c) an instruction for using the kit. In some embodiments, the multi-well plate is a 6-well plate, an 8-well plate, a 12-well plate, a 24-well plate, a 48-well plate, or a 96-well plate.

A non-limiting example of a kit used to perform any of the methods described herein includes: a) a slide comprising a plurality of arrays, wherein an array of the plurality of arrays comprises capture probes; b) a gasket comprising a plurality of apertures, wherein the gasket is configured to be mounted onto the slide such that the plurality of apertures are aligned with the plurality of arrays; and c) an instruction for using the kit.

EXAMPLES

The invention is further described in the following examples, which do not limit the scope of the invention described in the claims.

Example 1

Live Sample Preparation and System Setup

Figure 12A:
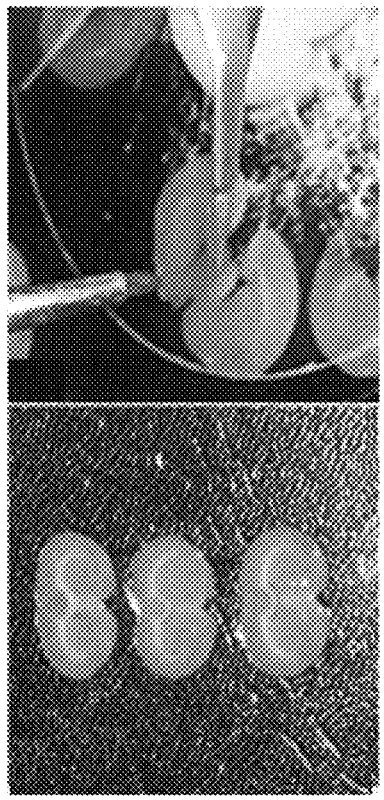
FIG. 12A shows a representative Vibratome for tissue slicing.
Figure 12B:
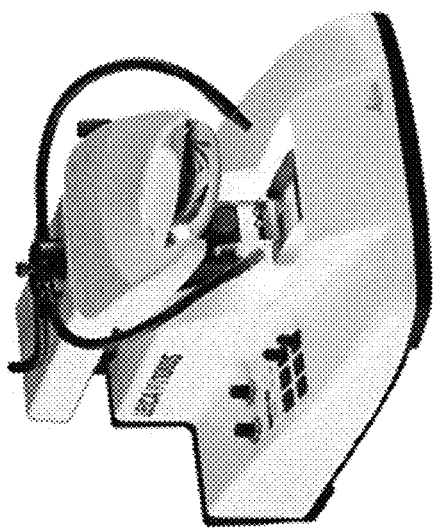
FIG. 12B shows preparation of live tissue sections.
Figure 12C:
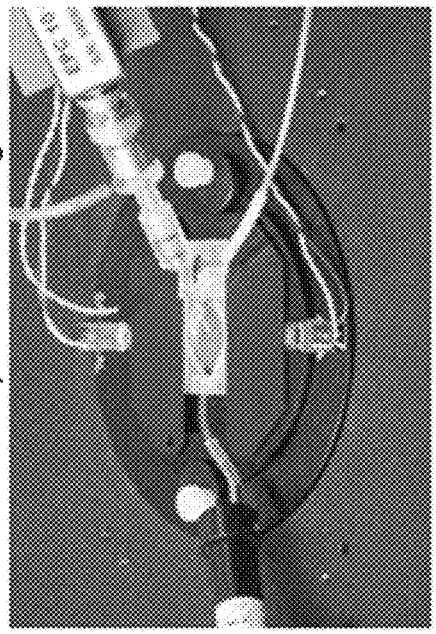
FIGS. 12C and 12D show a representative perfusion chamber and assembly of the chamber to a microscope.
Figure 12D:
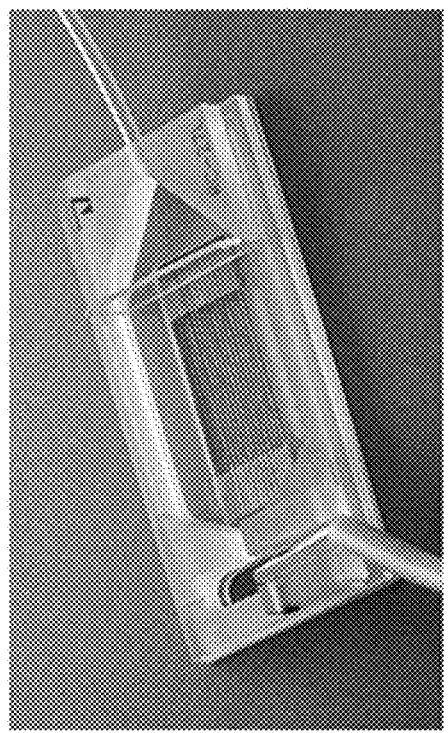
Figures 13A, 13B, 13C:
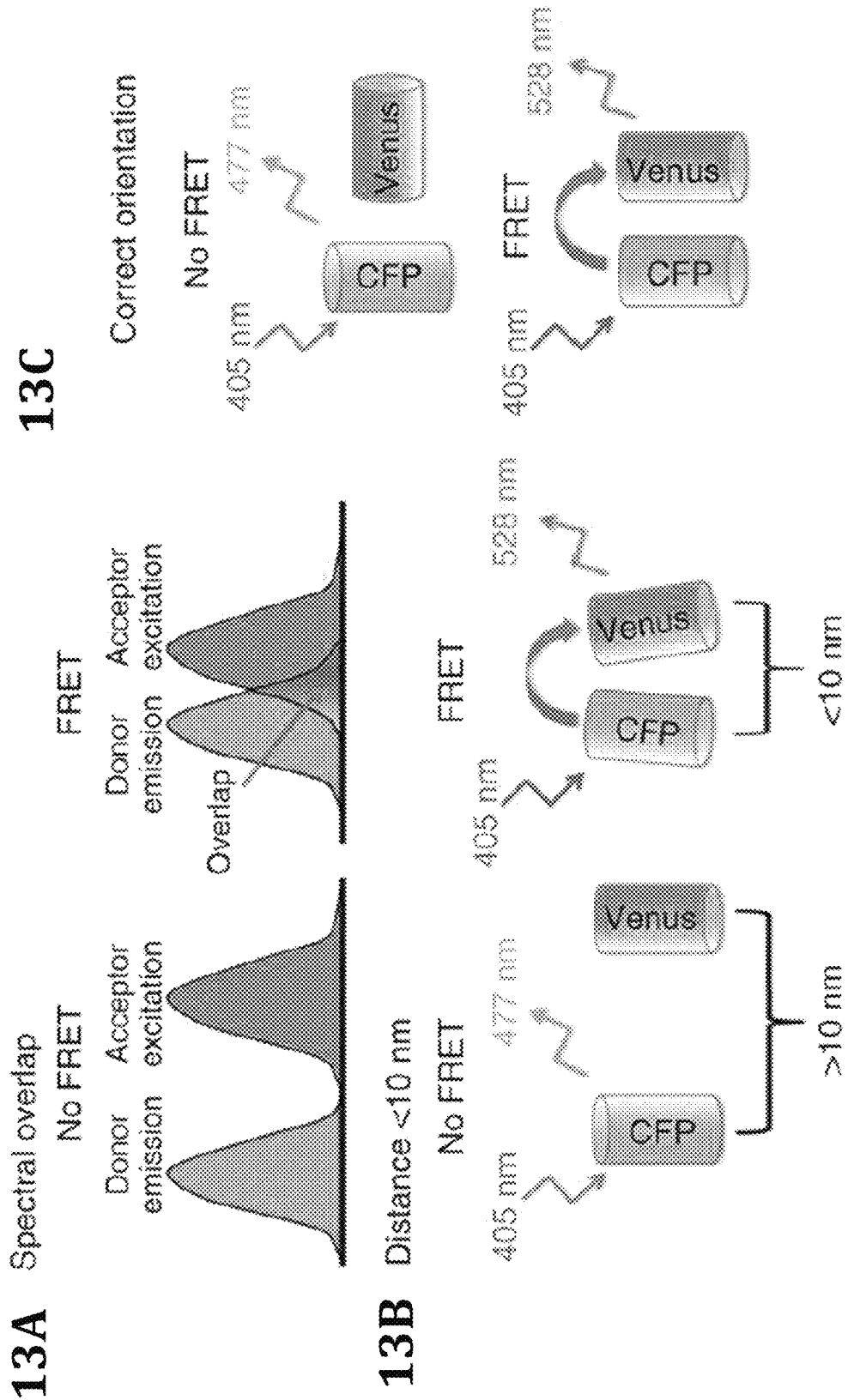
FIGS. 13A-13C show a schematic illustrating mechanisms of fluorescence resonance energy transfer (FRET).
Figure 14:
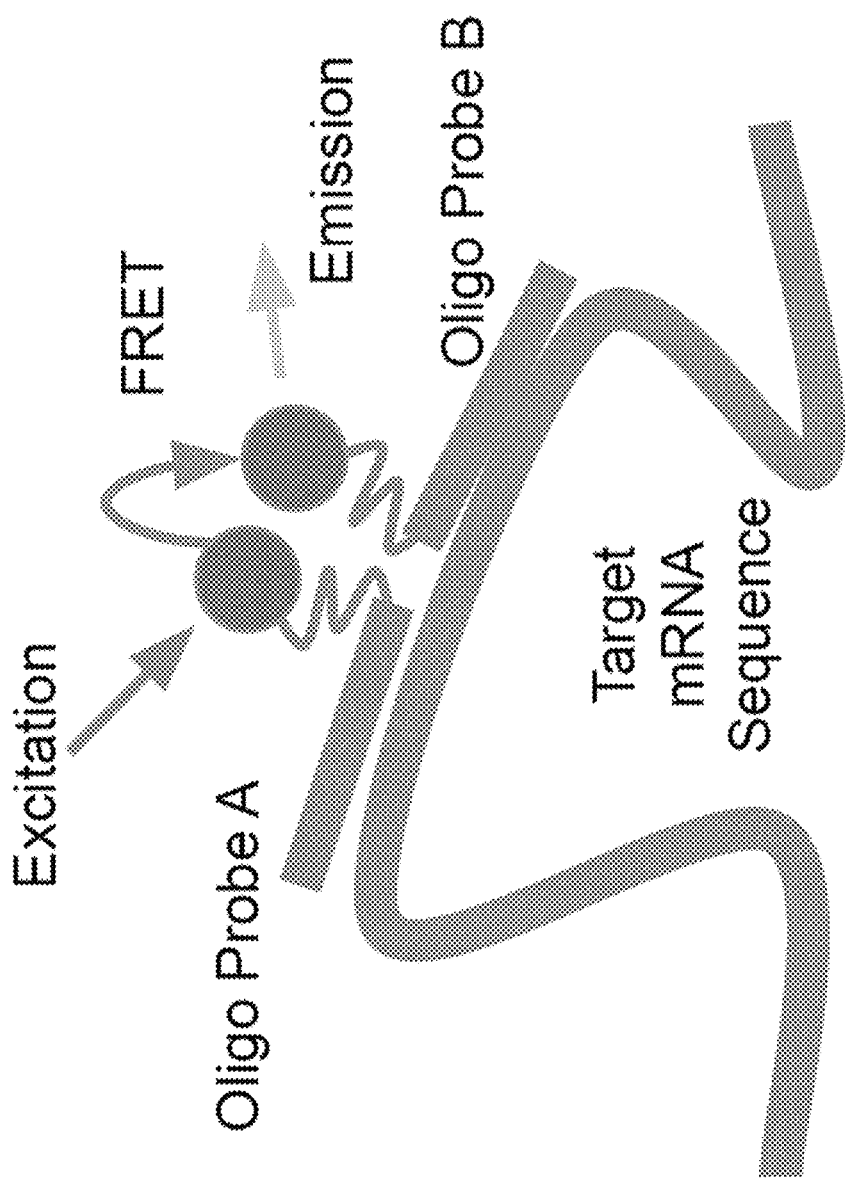
FIG. 14 shows a schematic of detecting hybridization of fluorescently labelled oligo probes to a target mRNA sequence using FRET.

Live samples can be prepared for spatio-temporal measurements as shown in FIGS. 12A-12D. Live samples (e.g., live tissue sections) can be generated using a Vibratome (FIG. 12A) and viability maintained (FIG. 12B) in oxygenated media. Traditional chambers equipped with an inlet and outlet port for constant flow of media can be designed to promote laminar flow as exemplified in FIG. 12C. Such chambers can be adapted to assemble with the spatial array described herein. Alternatively, perfusion chamber assembly can be custom made, for example, as shown in FIGS. 10A-10B. Testing can occur by, for example, placing the perfusion chamber under a microscope or other device or apparatus for capturing cellular activity or gene expression upon testing of the live sample (FIG. 12D).

Example 2

Measuring Cellular Activity Using the Perfusion Chamber or the Multi-Well Plate

As a non-limiting example, the perfusion chamber or the multi-well plate described herein can be used for measurement of cellular activity. For example, live brain tissue sample can be sectioned from a fresh brain tissue by Vibratome and cultured in a perfusion chamber or a multi-well plate described here. Tissue culture medium specific for live brain samples can be perfused through (or added by pipetting) to maintain tissue viability. Voltage-sensitive dyes can be added to the culture medium and perfused to the perfusion chamber (or added to the multi-well plate by pipetting) to interact with the brain tissue sample. Fast membrane potential changes, e.g., action potentials in single neurons, can be optically recorded by time-lapse fluorescent microscopy. Immediately following the recording, the brain tissue sample can be fixed by 2% paraformaldehyde. Following fixation, the cover and gasket are disassembled. The tissue sample can then be subjected to a spatial analysis workflow as described herein.

Example 3

Measuring Intracellular Gene Expression Using the Perfusion Chamber or the Multi-Well Plate As a non-limiting example, a perfusion chamber (or a multi-well plate) described herein can be used for measurement of intracellular gene expression, e.g., splicing of a transcript by FRET. For example, cells expressing the gene transcript can be seeded directly in the perfusion chamber (or the multi-well plate) and cultured for at least 2 days when cell confluence reaches about 80%. Two fluorescently labelled PNA probes can be perfused to the perfusion chamber (or added to the multi-well plate by pipetting) to interact with the cells. The first probe targeting to an upstream exon can be labelled with Cyan Fluorescent Protein (CFP) and the second probe targeting to a downstream exon can be labelled with Venus Fluorescent Protein (VFP or Venus). Upon splicing, the ligated upstream and downstream exons are close enough (e.g., within 10 nm) such that emission of CFP can excite VFP, resulting in VFP-specific fluorescence emission signals. Drugs that interfere with splicing can also be perfused (or added by pipetting) to interact with the cells and VFP-specific emission signals can be recorded. Immediately following the recording, the cells can be fixed by 2% paraformaldehyde. Following fixation, the cover and gasket are disassembled. The cell sample can then be subjected to a spatial analysis workflow as described herein.

Figure 15:
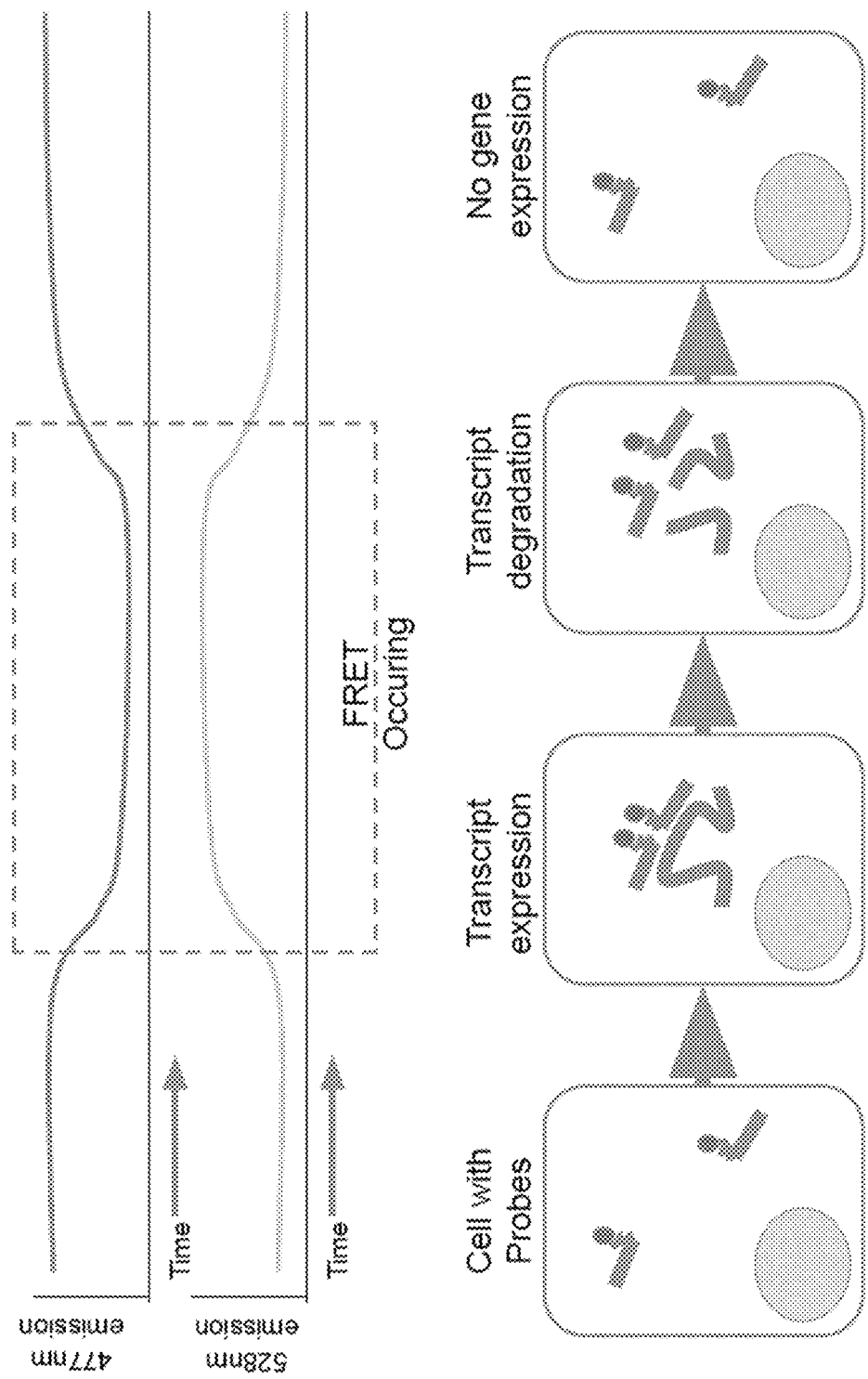
FIG. 15 shows an exemplary recording result and corresponding hybridization status for detecting gene expression of a target mRNA sequence via FRET.
Figure 16:
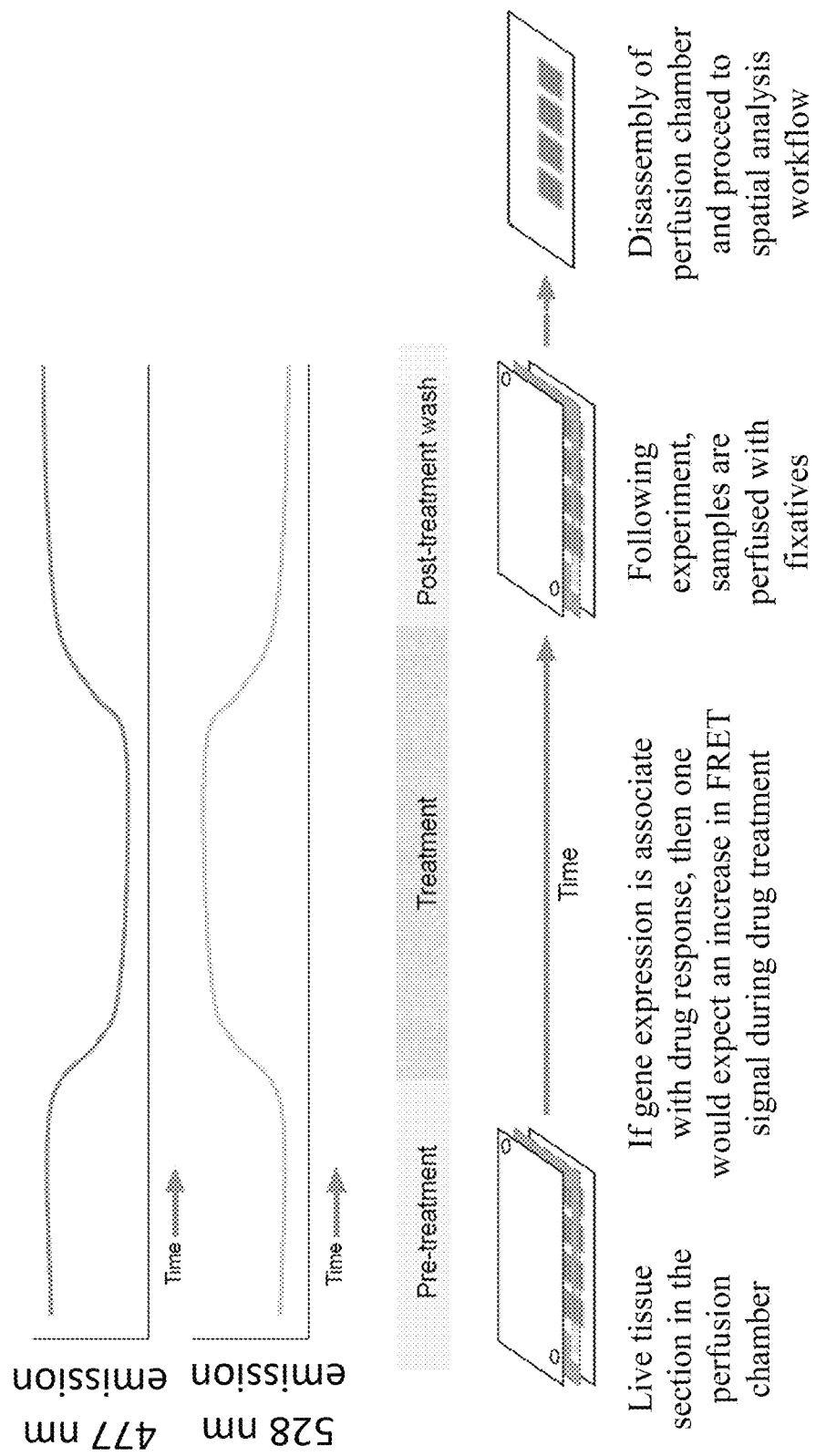
FIG. 16 shows an exemplary recording result and schematic workflow for detecting real-time response during pharmacological treatment via FRET.

As a non-limiting example, the perfusion chamber or the multi-well plate described herein can be used for measurement of intracellular gene expression, e.g., visualizing transcripts in live cells or tissues. Live cells expressing a target mRNA sequence can be seeded directly in the perfusion chamber (or the multi-well plate) and cultured when cell density reaches an appropriate confluence. As shown in FIGS. 13A-13C and FIG. 14, two fluorescently labeled oligo probes (oligo probe A and oligo probe B) targeting neighboring sequences of the target mRNA can be added to the perfusion chamber (or the multi-well plate) to internalize into the live cells. Oligo probe A can be labelled with a CFP as a donor fluorophore and oligo probe B can be labelled with VFP (or Venus) as an acceptor fluorophore. FRET can occur when emission spectra from the donor fluorophore overlaps with the excitation spectra of the acceptor fluorophore. FRET can be detected when distance of the donor and acceptor fluorophores are less than 10 nm and both fluorophores are correctly orientated. Specifically, CFP from oligo probe A can be excited at 405 nm and emits at 477 nm. When VFP from oligo probe B is at a distance less than 10 nm to CFP, the 477 nm emission can further excite VFP to emit at 528 nm. FIG. 15 shows an exemplary recording result of the emission at 477 nm and 528 nm when the cells are excited at 405 nm for a period of time. When the target mRNA is expressed, the two oligo probes can hybridize to the neighboring sequences of the target mRNA that allows FRET to occur, which is indicated as a decrease of the 477 emission signal with a simultaneous increase of the 528 emission signal. When the target mRNA is degraded, the free diffusing oligo probes would have a reduced rate of FRET occurrence, which is indicated as an increase of the 477 nm emission signal with a simultaneous decrease of the 528 nm emission signal. In addition, as shown in FIG. 16, drugs that interfere with the target mRNA expression can also trigger the 477 nm and 528 nm emission signal response during drug treatment. Immediately following the recording, the live cells can be washed and perfused (or added by pipetting) with fixatives (e.g., 2% paraformaldehyde). Alternatively, snap-shots of the live cells after drug treatments can be obtained by perfusing (or adding) the fixatives at different time points with proper controls (e.g., no treatment controls). Following fixation, the cover and gasket are disassembled. The cell sample can then be subjected to a spatial analysis workflow as described herein.

Example 4

Drug Screening Using the Perfusion Chamber or the Multi-Well Plate

Figure 19:
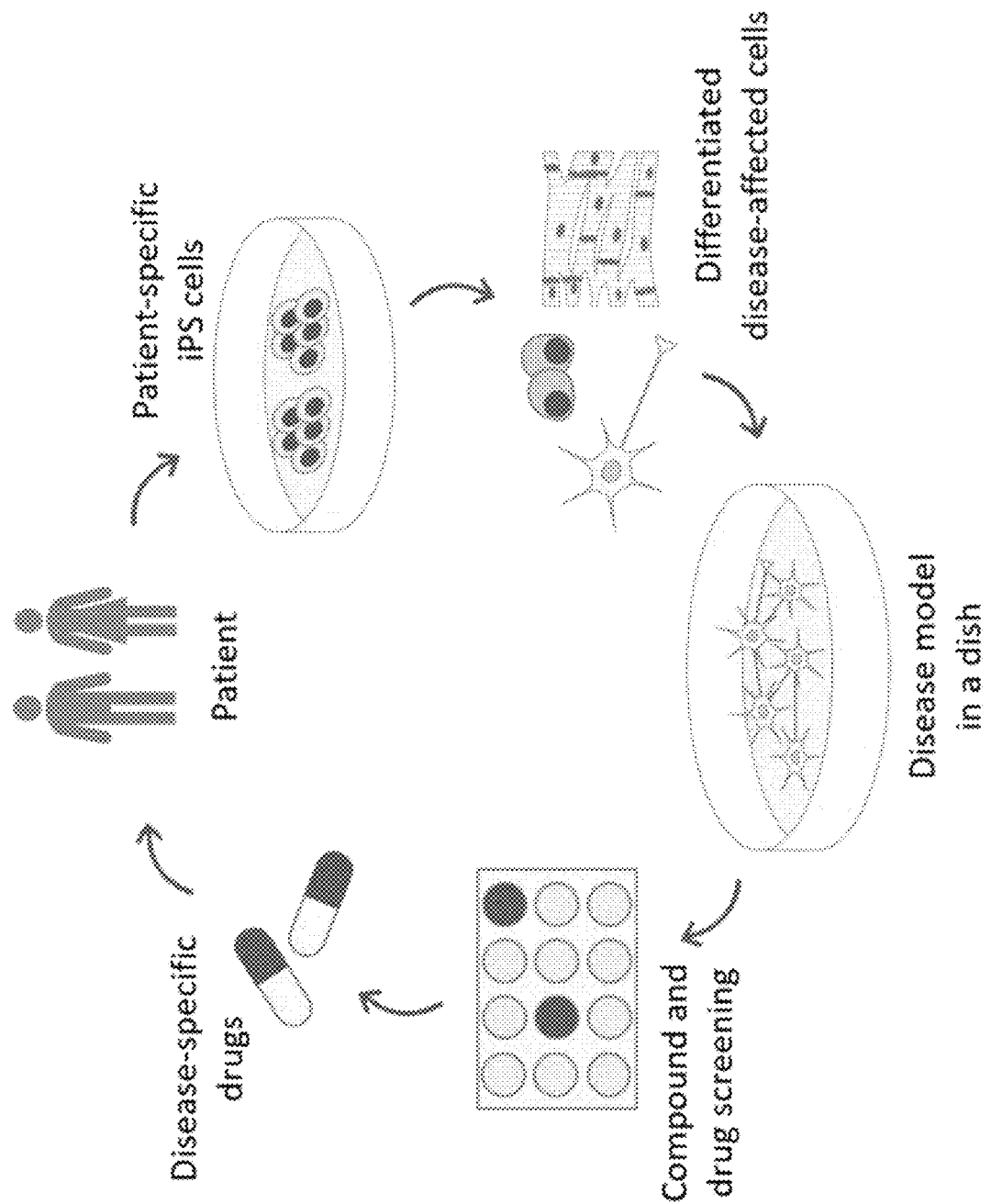
FIG. 19 shows a schematic of drug screening using patient samples. iPS cells: induced pluripotent stem cells.

As a non-limiting example, the perfusion chamber or the multi-well plate described herein can be used for drug screening. As shown in FIG. 19, skin or blood cells from human patients having a specific disease can be collected to generate patient-specific induced pluripotent stem cells (iPS cells). The iPS cells can be cultured in a dish to mimic disease-affected cells. Alternatively, the iPS cells can be stimulated to differentiate into an organoid sample, which can be used as a disease model. The organoid sample can be dissected and transferred into the perfusion chamber or the multi-well plate as described herein. Afterwards, the test compounds (e.g., drugs) can be diluted and used to treat the organoid sample in each chamber (or well) with proper controls. Cellular activities and/or intracellular gene expressions can be detected (e.g., recorded) in response to test compounds (e.g., drugs) treatment. The organoid sample can then be subjected to a spatial analysis workflow as described herein. Based on changes of the detected cellular activities and/or the intracellular gene expressions, together with the spatial analysis results, disease-specific drugs can be determined and used to treat the specific disease in the human patients.

Example 5

Tissue Culture on Spatial Arrays

Feasibility of cell culture on spatial arrays was assessed, according to the Visium Tissue Optimization Protocol. Specifically, A549 (ATCC® CCL-185™) human epithelial lung carcinoma cells were cultured in a T75 flask using F-12K media (ATCC® 30-2004) supplemented with 10% fetal bovine serum (FBS; ATCC® 30-2020). The cells were harvested when confluence reached 80-90%. Specifically, the cells were washed 1× with phosphate buffered saline (PBS; no $Mg^{2+}$, no $Ca^{2+}$), and dissociated in 3 ml of 0.25% (w/v) trypsin supplemented with 0.53 mM ethylenediaminetetraacetic acid (EDTA) for 5 minutes at 37° C. After dissociation, 3 ml of warmed complete media (F-12K, 10% FBS) was added and the cells were gently mixed by pipetting. The cells were transferred to a 15 ml Falcon tube, followed by centrifugation at 300 g for 15 minutes. After centrifugation, the supernatant was discarded and the cell pellet was resuspended with 1 ml of complete media. The total number of cells was counted using a Countess™ II automated cell counter (Thermo Fisher Scientific) after staining with 0.04% trypan blue dye. After determination of cell concentration, the cells were diluted to 20,000 cells per 200 µl, and 200 µl of the diluted cell suspension was added to each well of an assembled cassette. The assembled cassette included a spatial array slide that was assembled into a slide cassette via a removable gasket (details can be found in the Visium Spatial Tissue Optimization Reagent Kits User Guide (e.g., Rev D, dated October 2020), which is available at the 10x Genomics Support Documentation website). The assembled cassette was placed in a secondary container, and the cells were cultured until confluence reached 80-90%. The culture media was aspirated, and the cells were fixed in 4% paraformaldehyde (PFA). The fixed cells were stained and imaged. Analysis was performed according to the Visium Tissue Optimization Protocol. In particular, cDNA footprint images were obtained following tissue removal, with the cell outlines representing the collected mRNA from the A549 cells.

Figure 20A:
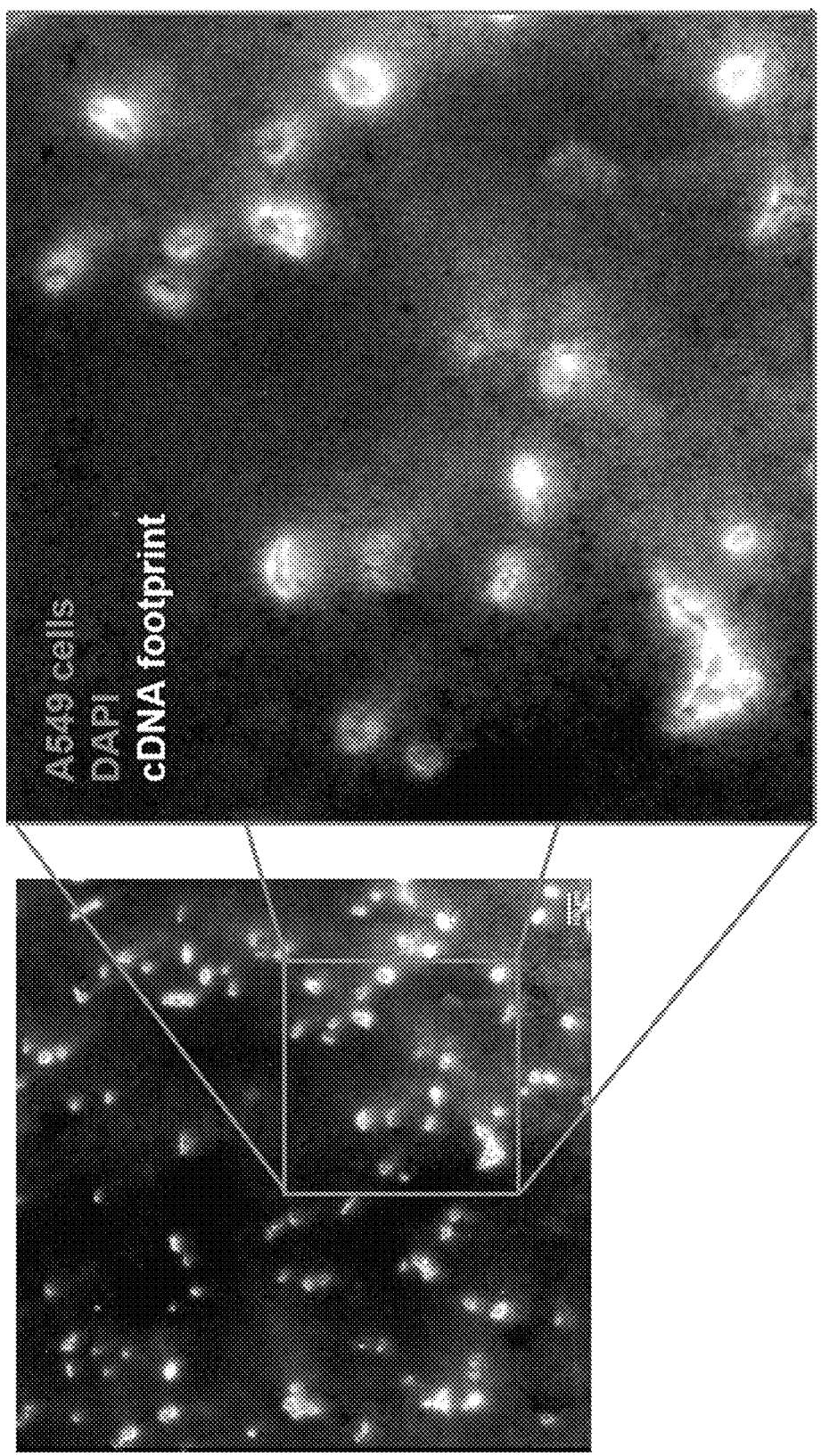
FIG. 20A shows a merged image of stained cells, stained cell nuclei (by DAPI), and cDNA footprint of A549 cells that were grown on top of a spatial array slide. An enlarged image of the merged image is shown on the right.
Figure 20B:
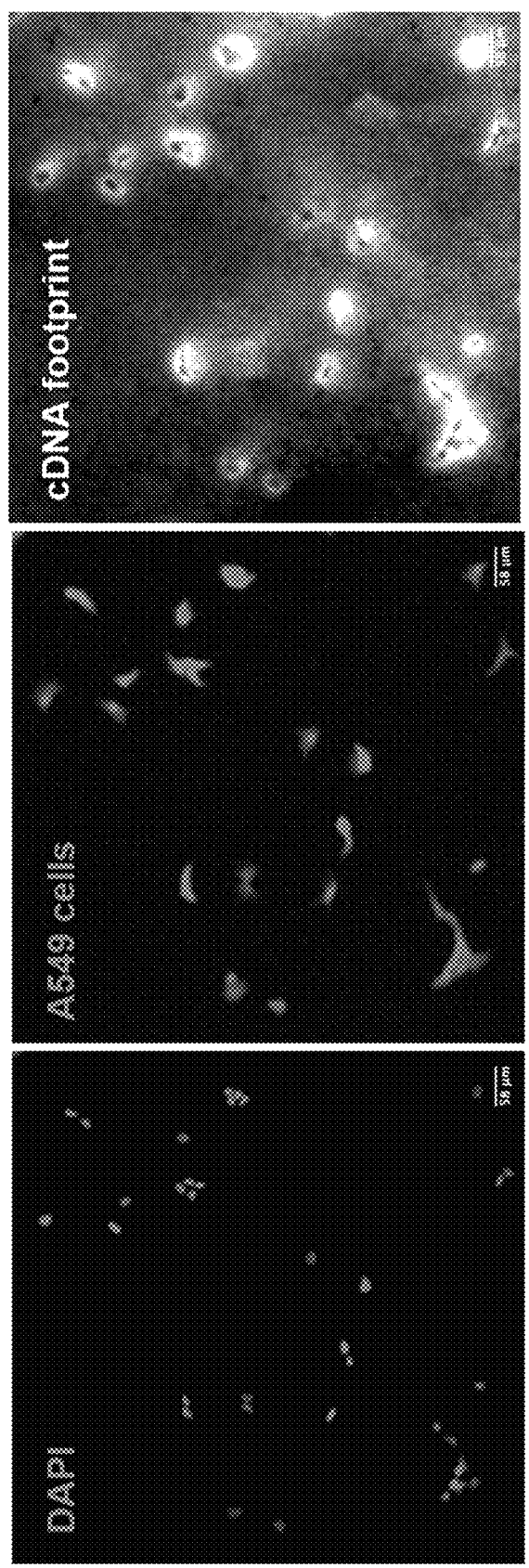
FIG. 20B shows breakout images of individual channels in FIG. 20A. Single-channel images of stained cell nuclei by DAPI, stained cells, cDNA footprint are shown from left to right, respectively.
Figure 20C:
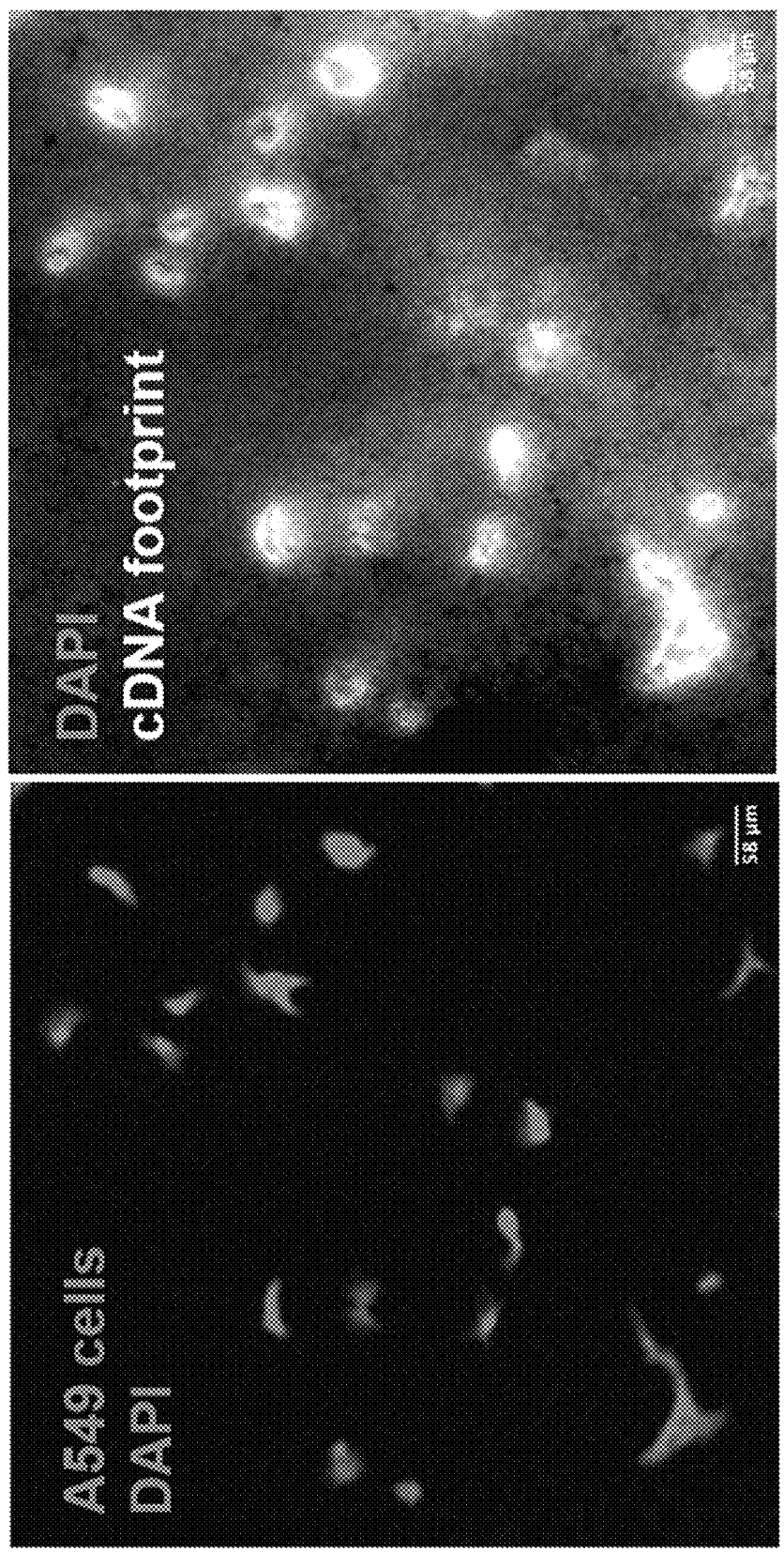
FIG. 20C shows a merged image of stained cells and stained cell nuclei (by DAPI) of the single-channel images shown in FIG. 20B (left); and a merged image of stained cell nuclei (by DAPI) and cDNA footprint of the single-channel images shown in FIG. 20B (right).

FIGS. 20A-20C, show the merged cell image and cDNA footprint image. The cDNA footprint image overlaid and aligned with the stained A549 cell image on the array slide. In general, the cDNA footprint followed the shape and morphology of the individual cells. However, transcript mislocalization (or transcript diffusion) was also observed, which led to a visible halo of transcripts surrounding the individual cells. It is contemplated that the addition of agents, such as crowding agents, would minimize the transcripts diffusing from the cells.

Feasibility of cell culture on spatial arrays was assessed, according to the Visium Gene Expression Protocol. The cells were treated with small molecule drugs (i.e., Osimertinib or Linsitinib) before harvesting. Specifically, A549 cells were prepared and added to each well of an assembled cassette as described above. The assembled cassette included a spatial array slide that was assembled into a slide cassette via a removable gasket (details can be found in the Visium Spatial Gene Expression Reagent Kits User Guide (e.g., Rev D, dated October 2020), which is available at the 10x Genomics Support Documentation website). The assembled cassette was placed in a secondary container, and the cells were cultured until confluence reached 80-90% (approx. 3 days). About 24 hours prior to harvesting, the cells were left untreated (as a control); treated with Osimertinib; treated with Linsitinib; or treated with both Osimertinib and Linsitinib. After harvesting, the culture media was aspirated, and the cells were fixed in 4% PFA. The fixed cells were imaged by brightfield microscopy, and spatial gene expression analysis was performed according to the Visium Gene Expression Protocol, which included steps of library preparation, sequencing, and data analysis. Following treatment and processing, experimental data was obtained from one replicate of untreated cultures, one replicate of Linsitinib-treated cultures, and two replicates of Osimertinib-treated cultures.

Figure 21A:
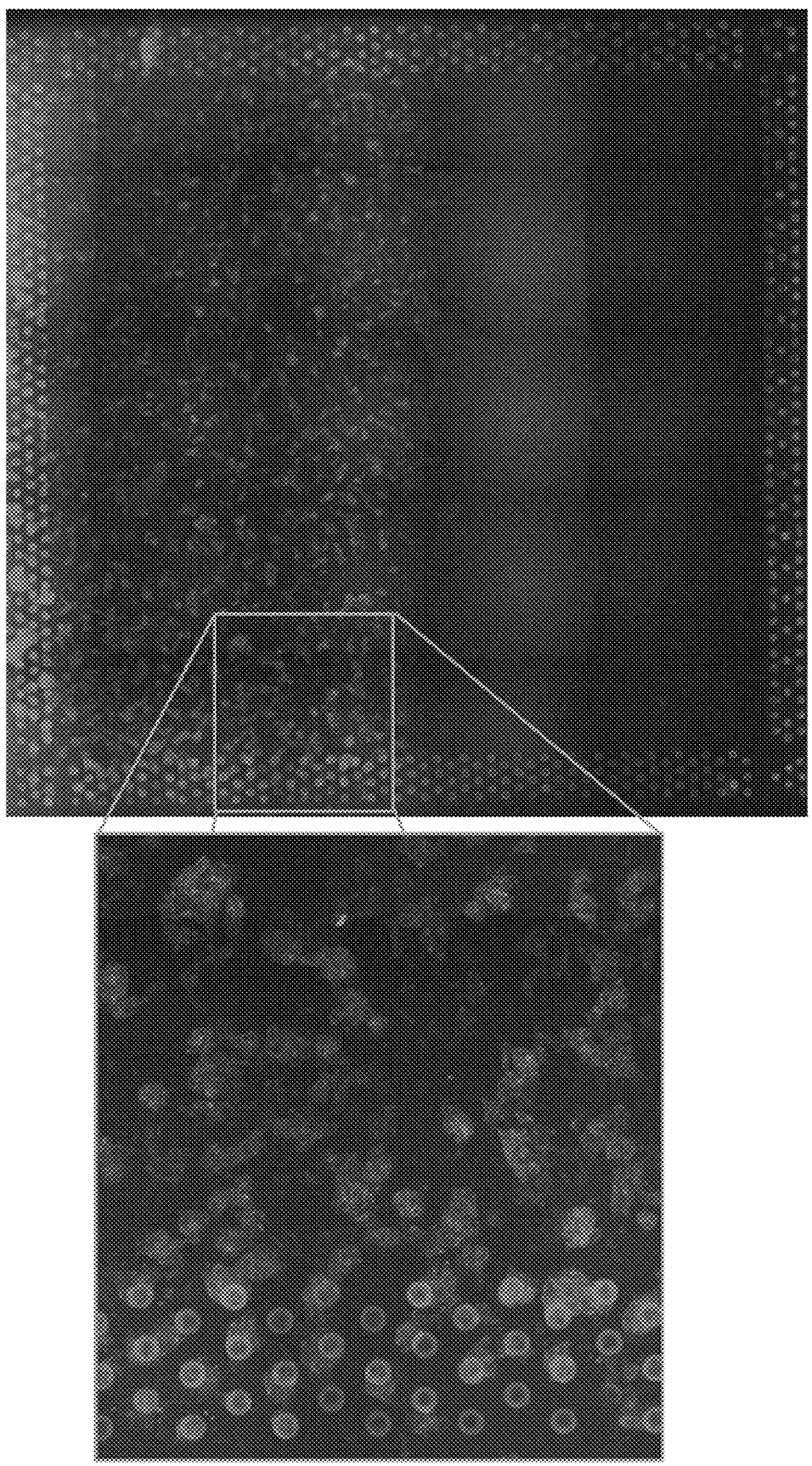
FIG. 21A shows a brightfield image of A549 cells that were grown on top of a spatial array slide. An enlarged image is shown on the left. The round dots on the edges are fiducial markers.
Figure 21B:
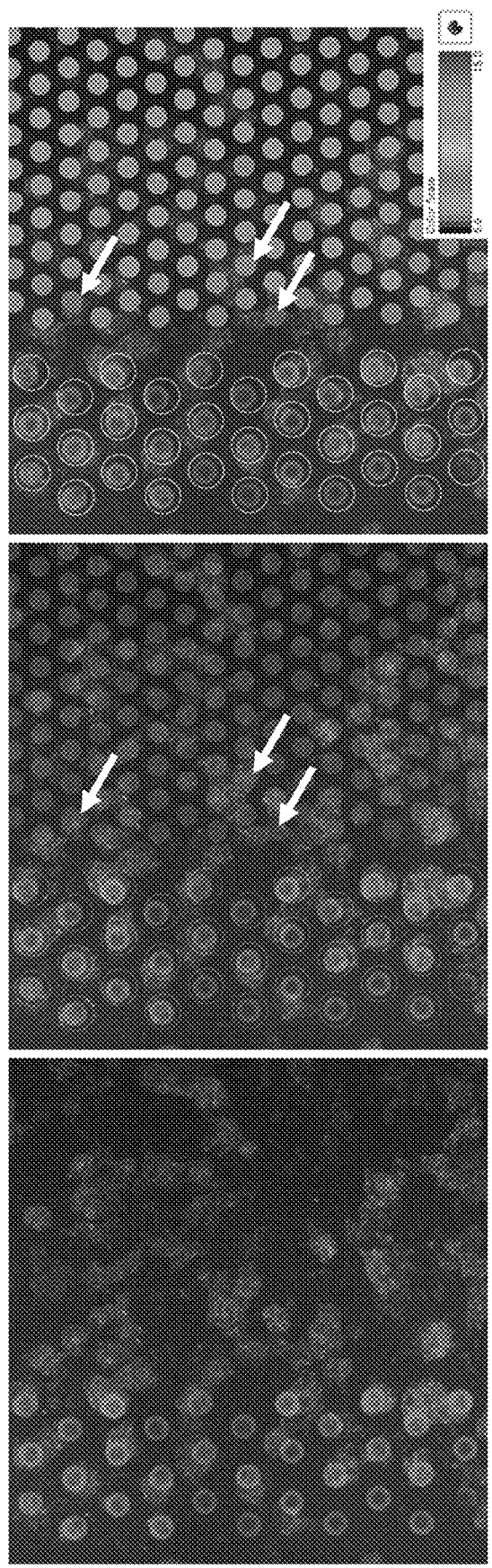
FIG. 21B shows merged images of the enlarged brightfield image in FIG. 21A overlaid with spots on the spatial array slide showing relative unique molecular identifier (UMI) counts. Regions of higher cell density are indicated by arrows.
Figure 22A:
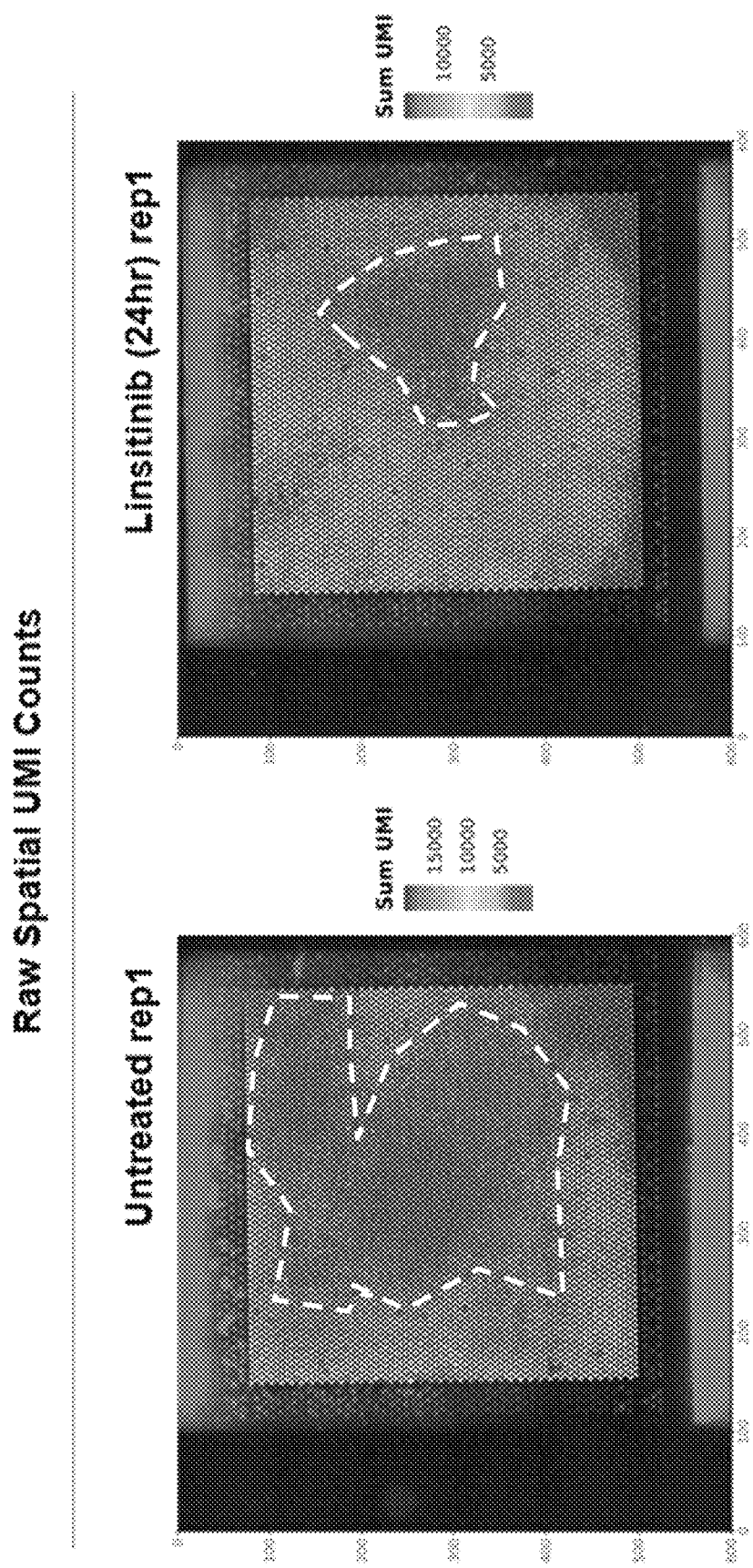
FIG. 22A shows raw spatial UMI plots. A549 cells grown on top of the spatial arrays were untreated (left), or treated with Linsitinib for 24 hours before harvesting (right). One replicate (rep1) for each culture was obtained for detecting UMI counts. Approximate boundaries of the plots are indicated by dashed lines.
Figure 22B:
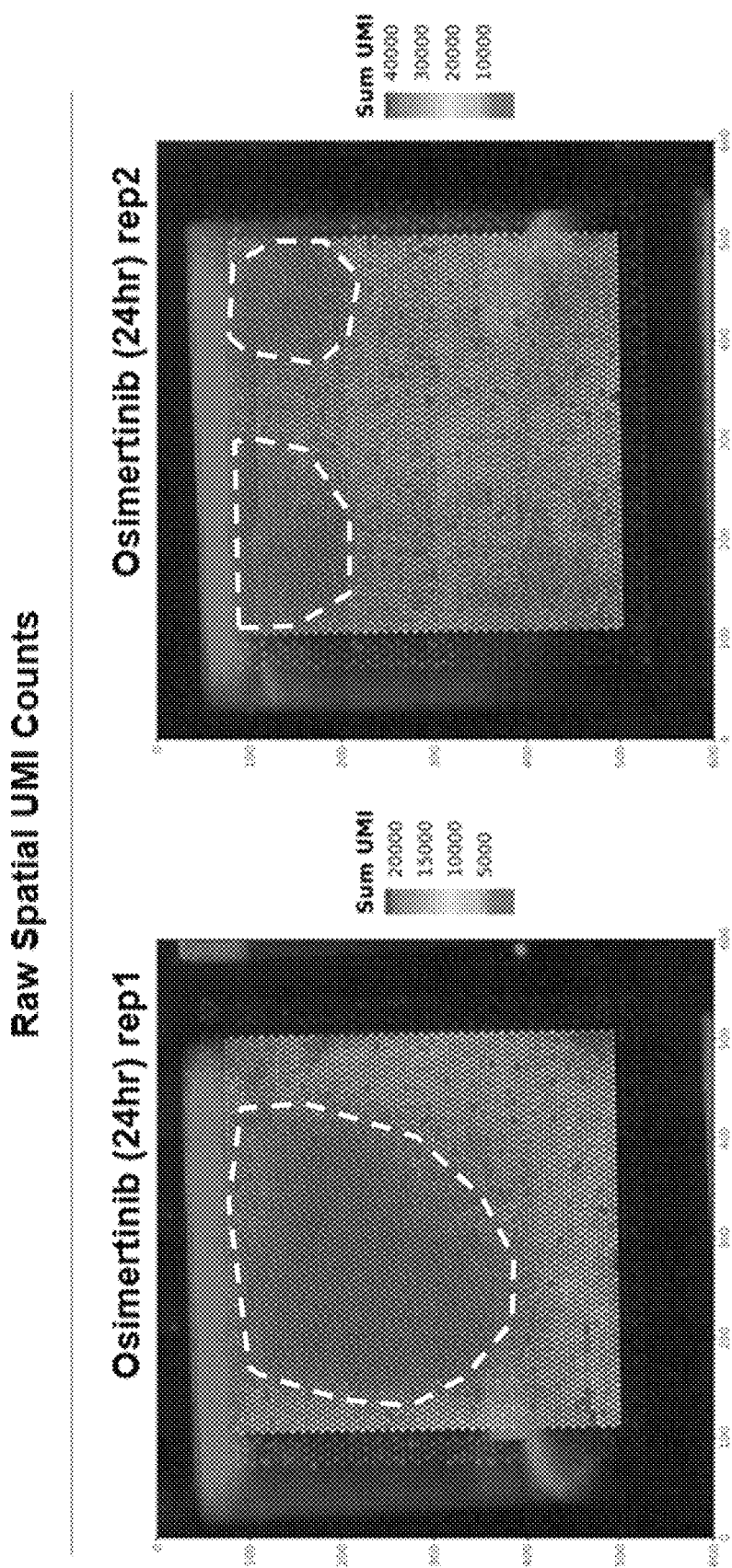
FIG. 22B shows raw spatial UMI plots. A549 cells grown on top of the spatial arrays were treated with Osimertinib for 24 hours before harvesting. Two replicates (rep1 and rep2) of Osimertinib-treated cultures were obtained for detecting UMI counts. Approximate boundaries of the plots are indicated by dashed lines.
Figure 22C:
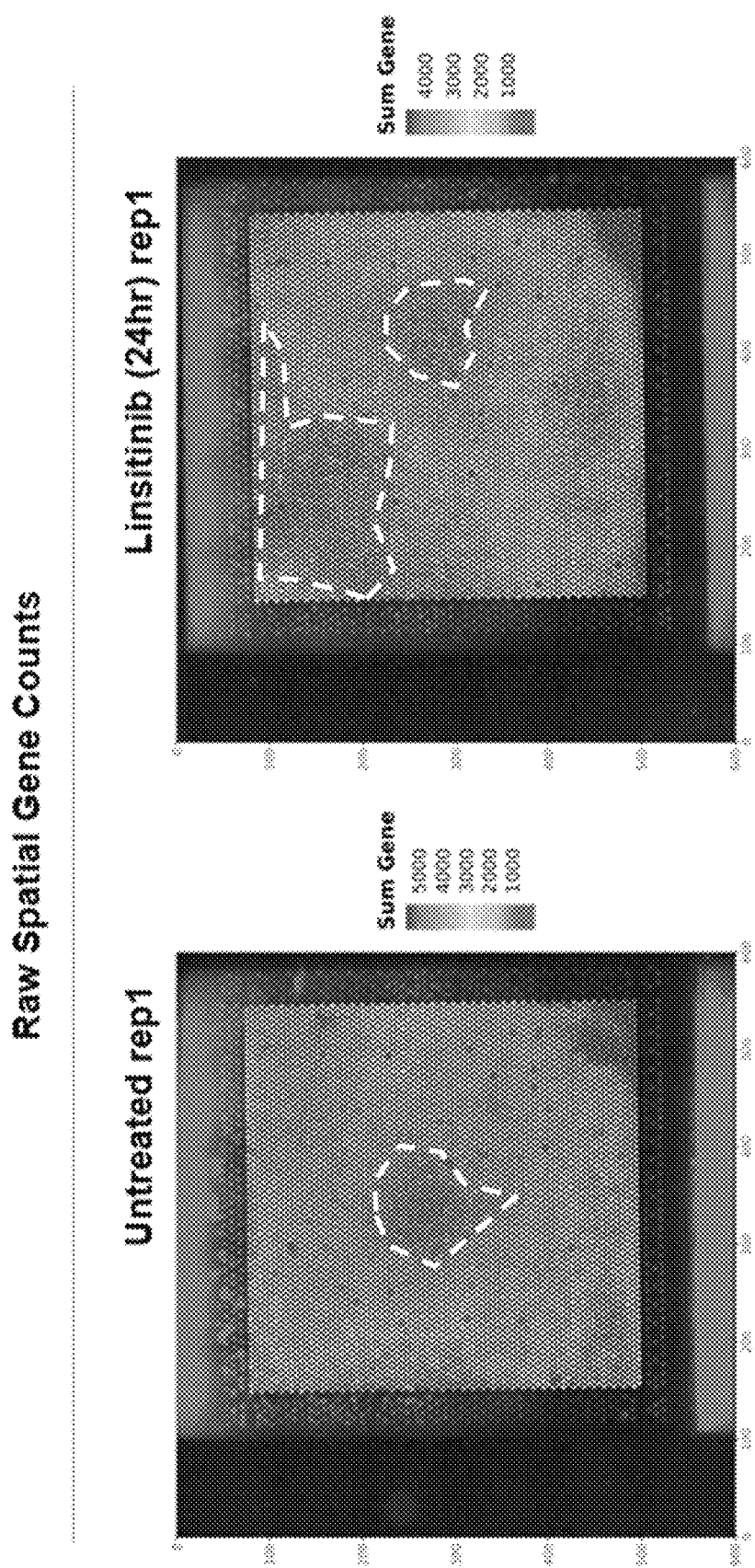
FIG. 22C shows raw spatial Gene plots. A549 cells grown on top of the spatial arrays were untreated (left), or treated with Linsitinib for 24 hours before harvesting (right). One replicate (rep1) for each culture was obtained for detecting gene counts. Approximate boundaries of the plots are indicated by dashed lines.
Figure 22D:
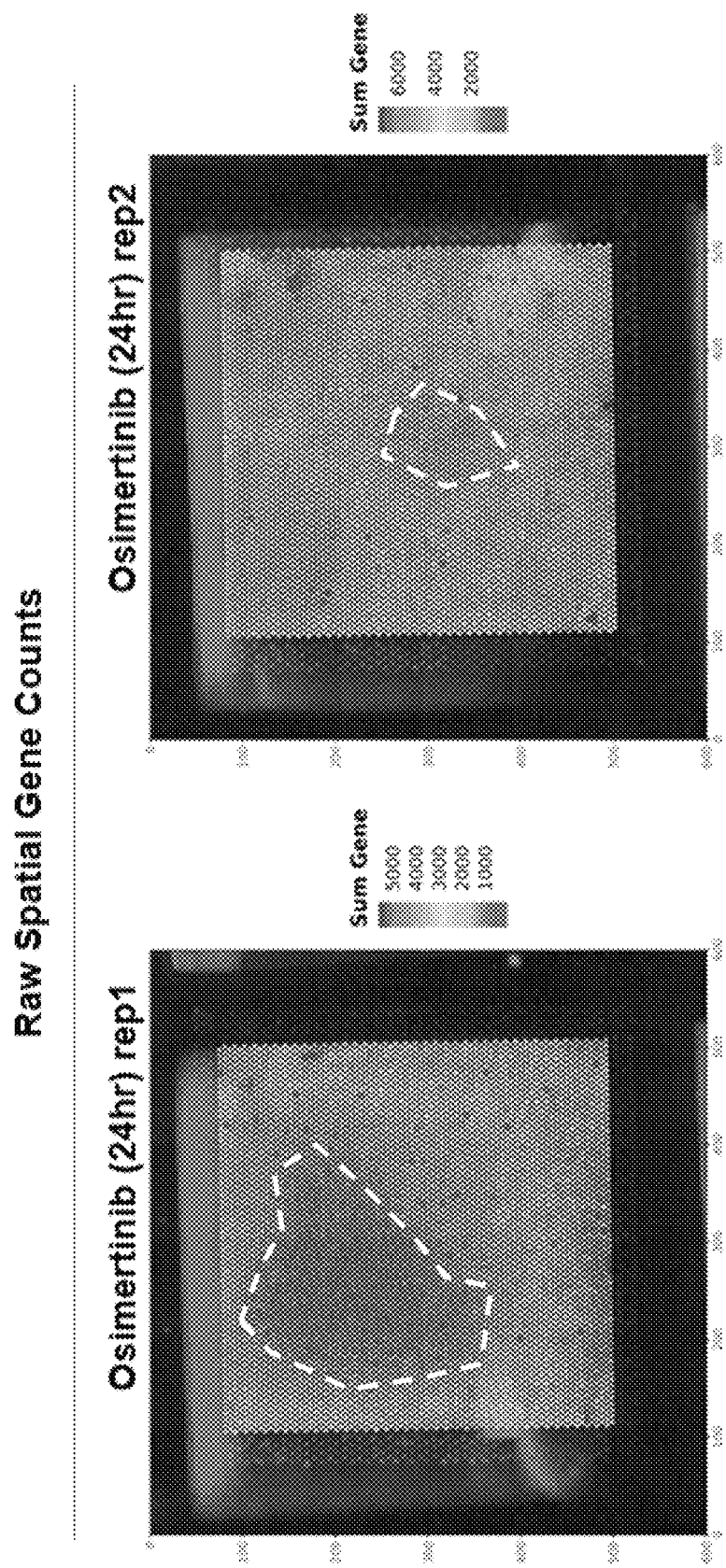
FIG. 22D shows raw spatial Gene plots. A549 cells grown on top of the spatial arrays were treated with Osimertinib for 24 hours before harvesting. Two replicates (rep1 and rep2) of Osimertinib-treated cultures were obtained for detecting gene counts. Approximate boundaries of the plots are indicated by dashed lines.

As shown in FIG. 21A, A549 cells were viable and proliferated on top of the spatial array slide. Cell images were taken by capturing the autofluorescence emitted from the cells, and the viable cells appeared morphologically normal. Growth on or surrounding the printed fiducials were also observed. FIG. 21B indicates that regions of higher cell density coincided with higher relative UMI counts.

Spatial UMI counts and gene detection counts were determined in untreated and drug-treated cultures. As shown in FIGS. 22A-22D, transcript capture was detected as indicated by spatial UMI and gene plots, indicating that culturing cells on top of the spatial array slide did not affect data quality of the spatial analysis. However, it is contemplated that one or both of non-uniform cell growth pattern and cell detachment during processing may have resulted in areas of low UMI and gene counts.

Figure 23A:
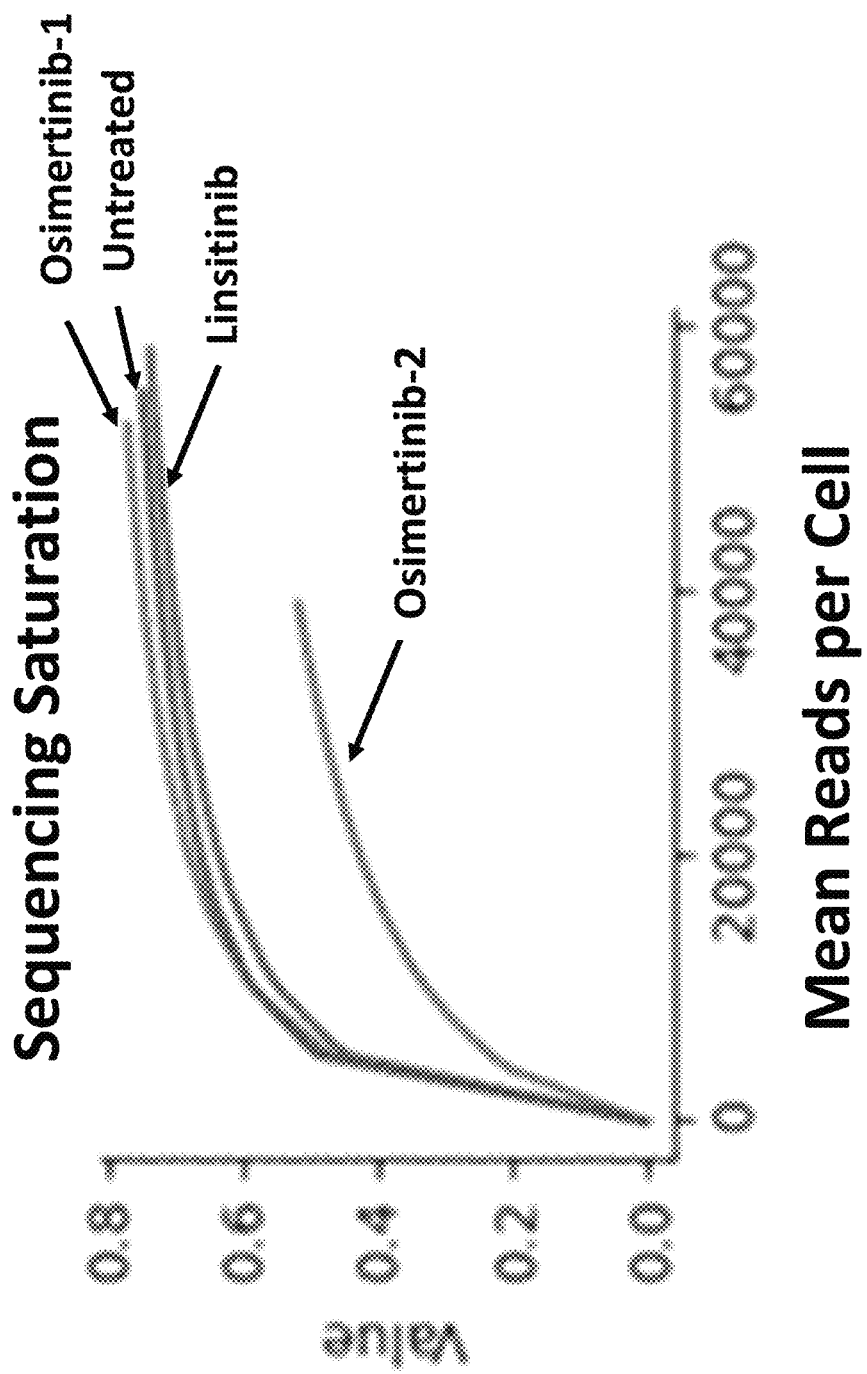
FIGS. 23A-23C show saturation curves by drug treatment. Osimertinib-1 and Osimertinib-2 are two replicates of Osimertinib-treated cells.
Figure 23B:
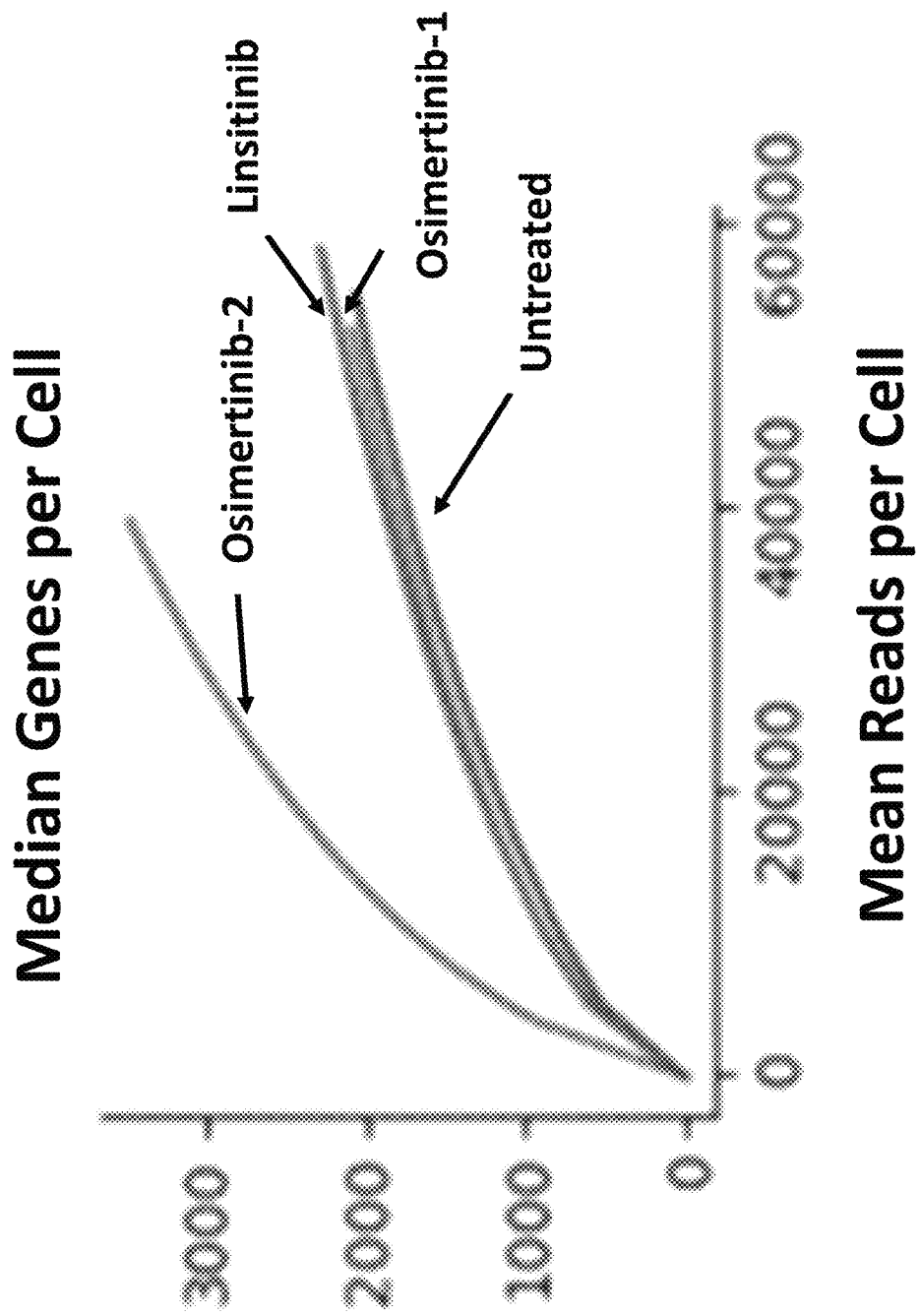
Figure 23C:
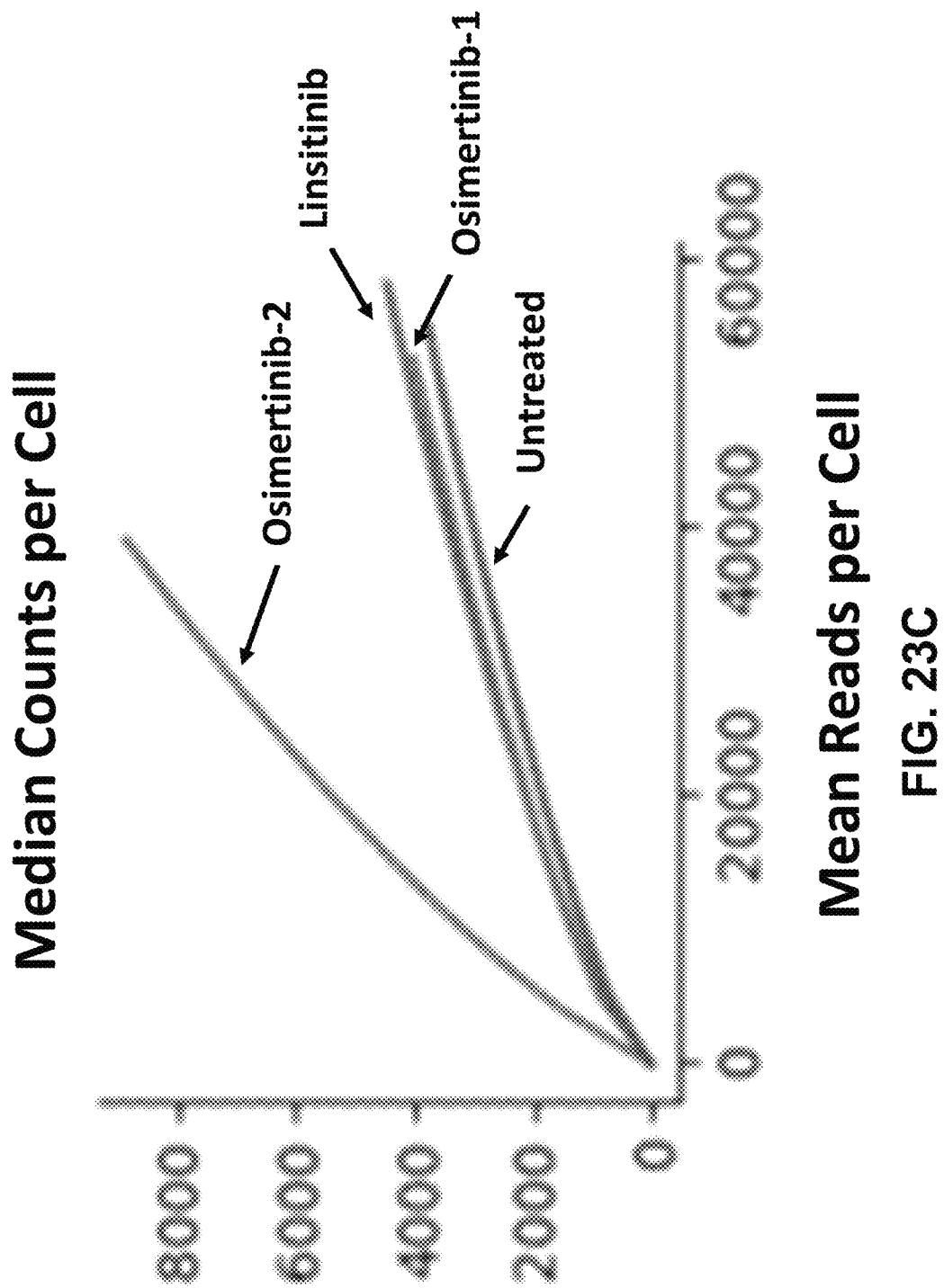
Figure 23D:
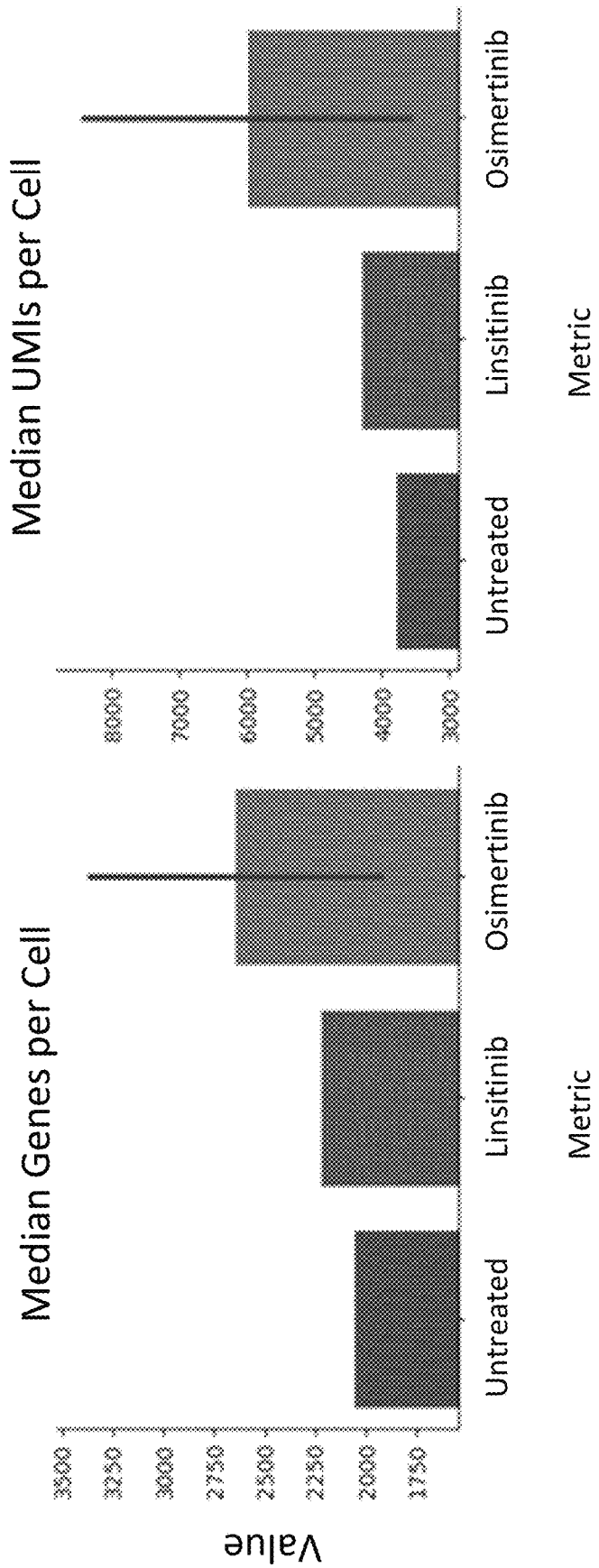
FIG. 23D shows complexity metrics based on the aggregated matrix by drug treatment.
Figure 23E:
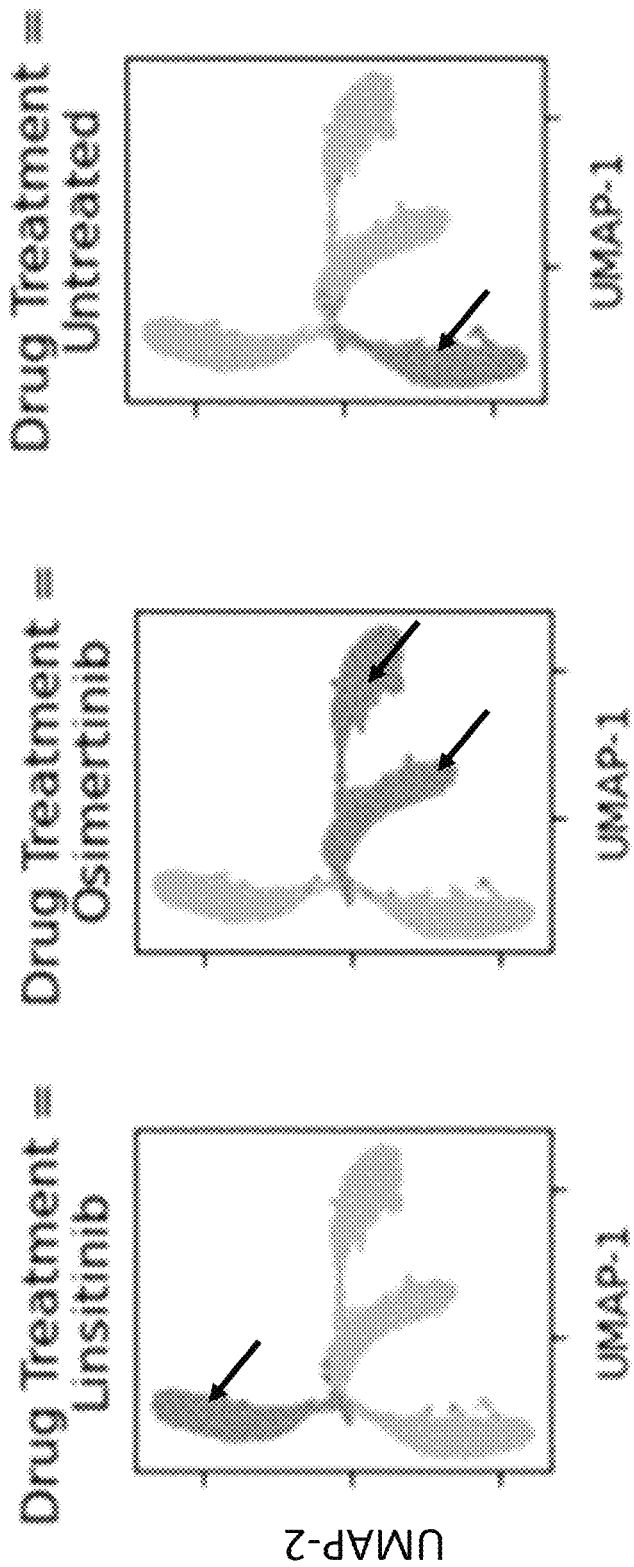
FIG. 23E shows column-wise grey UMAP (uniform manifold approximation and projection) plot by drug treatment. Different treatment clusters are indicated by arrows.

The spatial analysis results of the untreated and drug-treated cultures were also compared. FIGS. 23A-23E showed that the sequencing metrics derived from each of cultured capture areas exhibited comparable results. Because two replicates of Osimertinib-treated cells were used in the analysis, it was contemplated that the Osimertinib-treated areas would have an increased variation of sequencing saturation, median genes per cells, median counts per cell, and median UMIs per cell as compared to untreated areas or Linsitinib-treated areas (FIGS. 23A-23D). In addition, the two replicates of Osimertinib-treated cells also accounted for the clustering variation observed within the UMAP plot (FIG. 23E). Nevertheless, distinct clustering patterns were detected between the untreated, Osimertinib-treated, and Linsitinib-treated cultures.

Figure 24A:
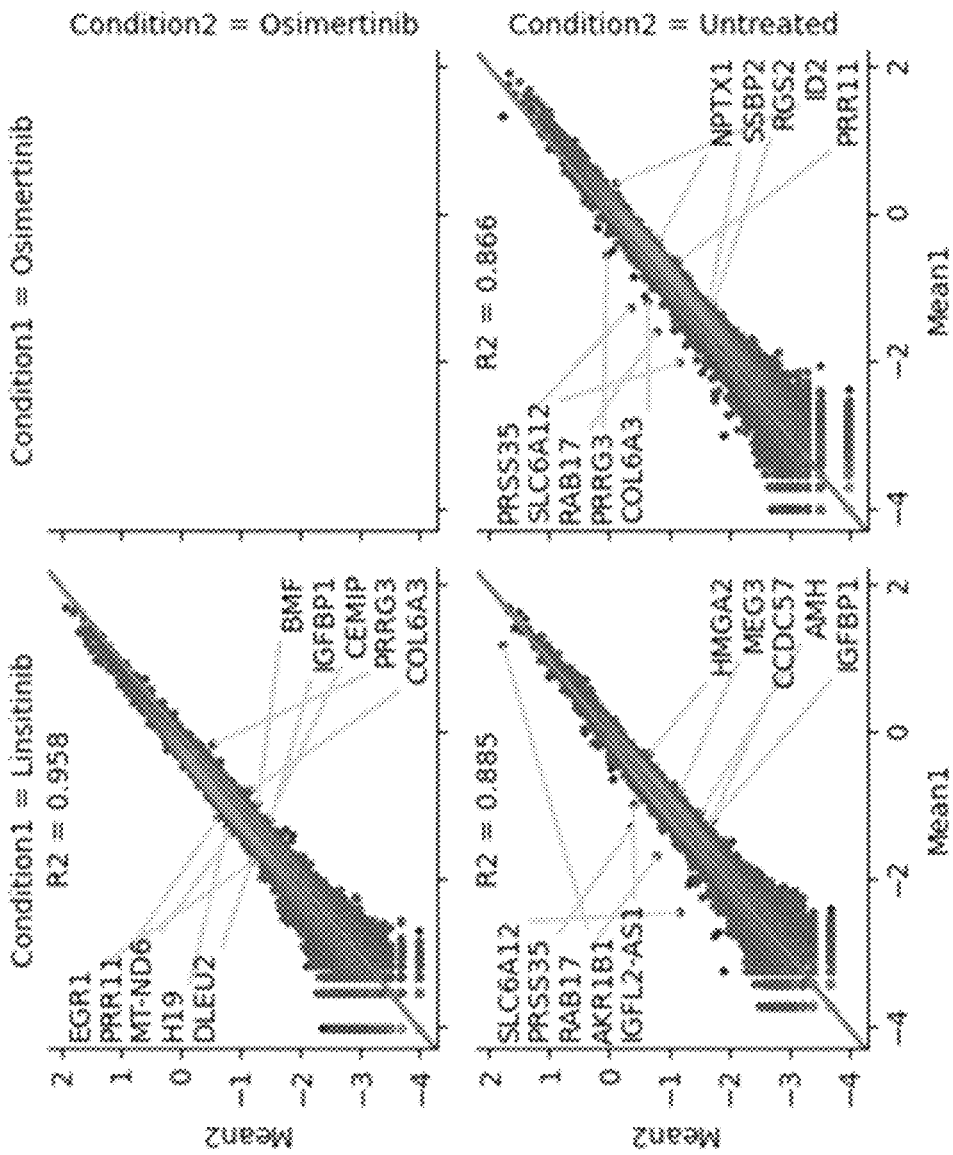
FIG. 24A shows scatter plots of genes across drug treatment. Differentially expressed genes are indicated in the plots.

In addition, a differential analysis on gene expression based on the untreated and drug-treated cultures were determined and the results are shown in FIGS. 24A-24B. The results showed that multiple genes were differentially expressed (e.g., either upregulated or downregulated) after treatment of Osimertinib or Linsitinib to the live cells. For example, as compared to the Linsitinib-treated cells, Osimertinib-treated cells exhibited increased expression of BMF, IGFBP1, CEMIP, PRRG3, and COL6A3; as compared to the untreated cells, Linsitinib-treated cells exhibited increased expression of SLC6A12, PRSS35, RAB17, AKR1B1, and IGFL2-AS1 (FIG. 24A). The top differentially expressed genes were also detected. For example, as compared to the Linsitinib-treated cells, the top 5 genes with increased expression level in Osimertinib-treated cells were PRRG3, CITED4, AHNAK2, NPDC1, and ITGA3; as compared to untreated cells, the top 5 genes with increased expression level in Linsitinib-treated cells were PRSS35, AKR1B1, IGFL2-AS1, CCL2, and CRYAB (FIG. 24B).

Figure 25:
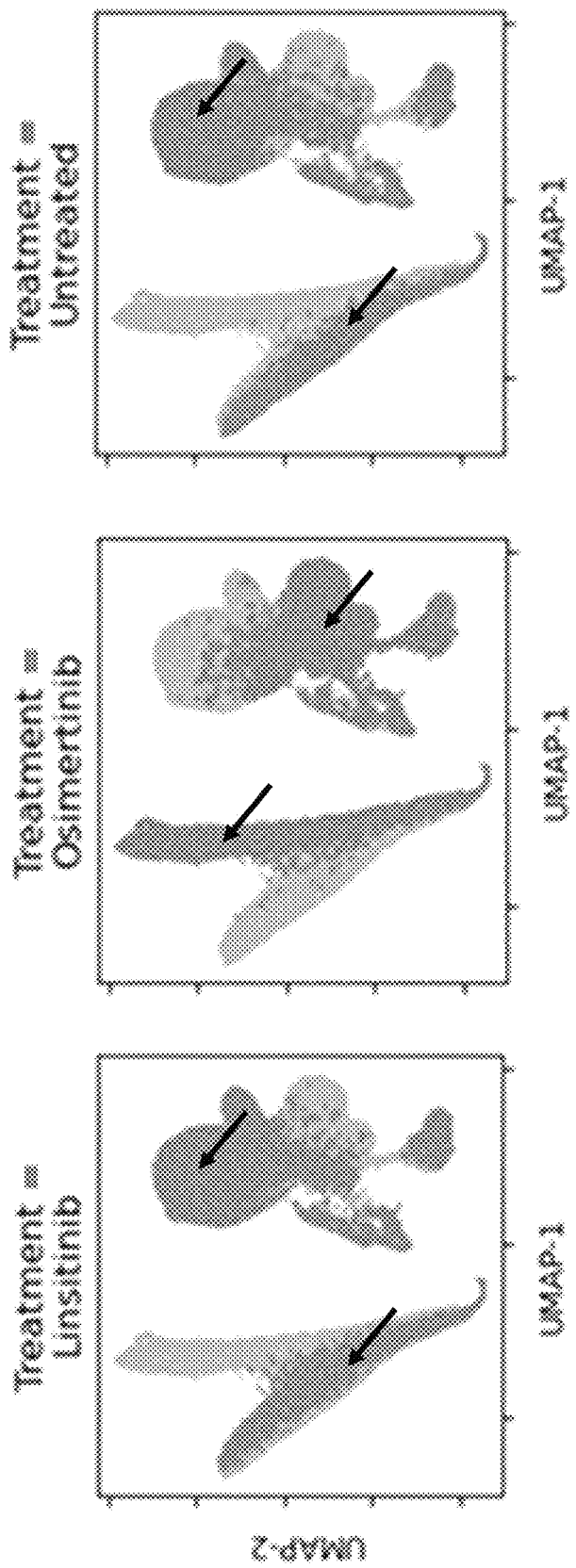
FIG. 25 shows column-wise grey UMAP plots by treatment. Different treatment clusters are indicated by arrows.

Further, a meta-analysis was performed on the samples using the Single-Cell Consensus Clustering Prime (SC3' or SC3P) (details can be found in the Chromium Next GEM Single Cell 3' Reagent Kits v3.1 (Dual Index) (e.g., Rev B, dated March 2021), which is available at the 10x Genomics Support Documentation website) or Visium pipelines, as shown in FIG. 25. Within the clustering results obtained by each tool, observable separation of the clustering pattern of Osimertinib-treated cultures was detected from those of the untreated or Linsitinib-treated cultures. Thus, differential gene expression induced by drug treatment was demonstrated by treating living cells with different drugs and evaluating their effect on gene expression using either single cell or spatial analysis pipelines.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying location and abundance of an analyte in a plurality of live cells, the method comprising:
   (a) contacting the plurality of live cells with a substrate comprising a plurality of capture probes, wherein a capture probe of the plurality of capture probes comprises (i) a spatial barcode and (ii) a capture domain that binds to a sequence present in the analyte;
   (b) recording a cellular activity or an intracellular gene expression of a nucleic acid in the plurality of live cells, wherein the plurality of live cells is located within a perfusion chamber comprising a gasket and the substrate, wherein the gasket comprises (i) a plurality of apertures, (ii) a plurality of input channels being fluidly connected to the plurality of apertures, respectively, and (iii) a plurality of output channels being fluidly connected to the plurality of apertures, respectively;
   (c) hybridizing the analyte to the capture domain of the capture probe;
   (d) extending the capture probe using the analyte as a template, thereby generating an extended capture probe;
   (e) amplifying the extended capture probe to produce a plurality of extended capture probes; and
   (f) sequencing (i) the spatial barcode, or a complement thereof, and (ii) all or part of the sequence of the analyte, or a complement thereof, and using the determined sequences of (i) and (ii) to identify the location and abundance of the analyte in the plurality of live cells,
   wherein step (b) occurs before steps (c), (d), (e), and (f).

2. The method of claim 1, further comprising mounting the gasket onto the substrate,
   wherein the substrate comprises a plurality of substrate regions, wherein a substrate region of the plurality of substrate regions comprises the capture probe comprising (i) the spatial barcode and (ii) the capture domain that binds to the sequence present in the analyte, and
   wherein the plurality of apertures of the gasket are aligned with the plurality of substrate regions of the substrate when the gasket is mounted onto the substrate.

3. The method of claim 2, further comprising mounting a cover onto the gasket,
   wherein the cover comprises an inlet and an outlet, the inlet being fluidly connected to the plurality of input channels when the cover is mounted onto the gasket, the outlet being fluidly connected to the plurality of output channels when the cover is mounted onto the gasket, and
   wherein the perfusion chamber further comprises the cover that is mounted onto the gasket.

4. The method of claim 1, further comprising perfusing a test compound through the perfusion chamber.

5. The method of claim 4, wherein the test compound is a drug.

6. The method of claim 4, wherein the perfusing step occurs prior to the recording step, or wherein the perfusing step and the recording step occur at substantially the same time.

7. The method of claim 1, further comprising culturing the plurality of live cells in the perfusion chamber before the recording step.

8. The method of claim 7, wherein the plurality of live cells is cultured in a culture medium in the perfusion chamber.

9. The method of claim 8, wherein the culture medium is supplemented with oxygen.

10. The method of claim 8, wherein the culture medium further comprises a blocking reagent, or wherein the plurality of live cells is treated with the blocking reagent.

11. The method of claim 1, wherein the recording step comprises optical recording.

12. The method of claim 11, wherein the optical recording comprises contacting the plurality of live cells with a chemical dye or an indicator.

13. The method of claim 12, wherein the chemical dye or the indicator comprises a fluorophore.

14. The method of claim 11, wherein the optical recording is achieved by in situ hybridization or fluorescence resonance energy transfer.

15. The method of claim 11, wherein the optical recording comprises hybridization of a plurality of optically-labelled probes to (a) a protein, a lipid, a nucleic acid, or a combination thereof associated with the cellular activity; or (b) the nucleic acid associated with the intracellular gene expression.

16. The method of claim 15, wherein an optically-labelled probe of the plurality of optically-labelled probes is a peptide nucleic acid probe labelled with a fluorophore.

17. The method of claim 1, wherein the plurality of live cells is a cell culture sample or a tissue sample.

18. The method of claim 17, wherein the tissue sample is a live tissue section, an organoid sample, or a spheroid culture sample.

19. The method of claim 17, wherein the cell culture sample is a primary cell culture sample comprising cells from a fresh tissue.

20. The method of claim 1, wherein the substrate is a coverslip comprising plastic, metal, or glass.

21. The method of claim 1, wherein the plurality of live cells is stained by immunohistochemistry or immunofluorescence before the recording step.

22. The method of claim 1, wherein the plurality of live cells is stained using a detectable label, wherein the detectable label is Can-Grunwald, Giemsa, hematoxylin and eosin (H&E), Jenner's, Leishman, Masson's trichrome, Papanicolaou, Romanowsky, silver, Sudan, Wright's, or Periodic Acid Schiff (PAS).

23. The method of claim 1, wherein the plurality of live cells is imaged using bright field imaging.

24. The method of claim 1, wherein the plurality of live cells is permeabilized with a permeabilization agent selected from an organic solvent, a cross-linking agent, a detergent, and an enzyme, or a combination thereof, wherein the plurality of live cells is permeabilized after step (b) and before step (c).

25. The method of claim 1, wherein the extending step comprises extending the capture probe at the 3' end.

26. The method of claim 1, wherein the plurality of live cells is removed after the amplifying step.

27. The method of claim 1, wherein the amplifying step comprises amplifying (i) all or part of the sequence of the analyte bound to the capture domain, or a complement thereof, and (ii) the spatial barcode, or a complement thereof.

28. The method of claim 1, wherein the identifying further comprises correlating the recording of the intracellular gene expression of the nucleic acid in the plurality of live cells to the location and abundance of the analyte in the plurality of live cells.

* * * * *